(12) United States Patent
Kienman et al.

(10) Patent No.: US 8,078,333 B2
(45) Date of Patent: Dec. 13, 2011

(54) DIALYSIS FLUID HEATING ALGORITHMS

(75) Inventors: Richard Kienman, Tampa, FL (US); Jennifer Lindsay, Clearwater, FL (US); Gideon Hecht, Seminole, FL (US); Rodolfo Roger, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 580 days.

(21) Appl. No.: 11/773,897

(22) Filed: Jul. 5, 2007

(65) Prior Publication Data

US 2009/0012655 A1    Jan. 8, 2009

(51) Int. Cl.
    *G05D 23/00*      (2006.01)

(52) U.S. Cl. .................... 700/300; 700/299; 604/29

(58) Field of Classification Search .......... 700/299, 700/300; 604/4, 6.13, 29; 392/470–490; 607/108, 113, 114; 210/196; 237/12.3 R; 62/235.1; 126/588, 651

See application file for complete search history.

(56) References Cited

U.S. PATENT DOCUMENTS

| | | | |
|---|---|---|---|
| 2,713,459 A | 7/1955 | Phillips | |
| 3,118,600 A | 1/1964 | Miller | |
| 3,460,459 A | 8/1969 | Austin | |
| 3,485,245 A | 12/1969 | Lahr et al. | |
| 3,809,241 A | 5/1974 | Alvine | |
| 3,909,588 A | 9/1975 | Walker et al. | |
| 4,093,847 A | 6/1978 | Walker et al. | |
| 4,180,460 A | 12/1979 | Calari | |
| 4,191,646 A | 3/1980 | Larsson et al. | |
| 4,194,536 A | 3/1980 | Stine et al. | |
| 4,245,665 A | 1/1981 | Anderson et al. | |
| 4,276,175 A | 6/1981 | Bower | |
| 4,293,762 A | 10/1981 | Ogawa | |
| 4,396,382 A | 8/1983 | Goldhaber | |
| 4,464,563 A | 8/1984 | Jewett | |
| 4,488,961 A | 12/1984 | Spencer | |
| 4,501,952 A | 2/1985 | Lehrke | |
| 4,532,414 A | 7/1985 | Shah et al. | |
| 4,558,207 A | 12/1985 | Litterst | |
| 4,574,876 A | 3/1986 | Aid | |
| RE32,303 E | 12/1986 | Lasker et al. | |
| 4,655,753 A | 4/1987 | Bellotti et al. | |
| 4,678,460 A | 7/1987 | Rosner | |
| 4,680,445 A | 7/1987 | Ogawa | |
| 4,735,609 A | 4/1988 | Comeau et al. | |
| 4,742,870 A | 5/1988 | Darone et al. | |
| 4,765,888 A * | 8/1988 | Barthe et al. | .................... 210/86 |
| 4,769,151 A | 9/1988 | Shouldice | |
| 4,804,474 A | 2/1989 | Blum | |
| 4,844,074 A | 7/1989 | Kurucz | |
| 4,847,470 A | 7/1989 | Bakke | |
| 4,906,816 A | 3/1990 | Van Leerdam | |
| 5,043,201 A | 8/1991 | Cote | |
| 5,073,167 A | 12/1991 | Carr et al. | |
| 5,125,069 A | 6/1992 | O'Boyle | |
| 5,180,896 A | 1/1993 | Gibby et al. | |
| 5,245,693 A | 9/1993 | Ford et al. | |

(Continued)

*Primary Examiner* — Dave Robertson
(74) *Attorney, Agent, or Firm* — K&L Gates LLP

(57) ABSTRACT

A dialysis fluid heating system includes a dialysis fluid heater; a dialysis fluid carrying element in operable communication with the dialysis fluid heater to heat a dialysis fluid; and a logic implementer configured to control the heater using (i) a heater input determined from a dialysis fluid temperature delta and a dialysis fluid flowrate, and (ii) a potential adjustment of the temperature delta using a measured dialysis fluid outlet temperature.

20 Claims, 52 Drawing Sheets

U.S. PATENT DOCUMENTS

| | | | |
|---|---|---|---|
| 5,295,964 | A | 3/1994 | Gauthier |
| 5,334,139 | A | 8/1994 | Jeppsson et al. |
| 5,338,293 | A | 8/1994 | Jeppsson et al. |
| 5,370,674 | A | 12/1994 | Farrell |
| 5,381,510 | A | 1/1995 | Ford et al. |
| 5,408,576 | A | 4/1995 | Bishop |
| 5,420,962 | A | 5/1995 | Bakke |
| 5,474,683 | A | 12/1995 | Bryant et al. |
| 5,485,542 | A | 1/1996 | Ericson |
| 5,588,959 | A * | 12/1996 | Ahmad et al. ............... 604/6.13 |
| 5,628,929 | A | 5/1997 | Klosterman |
| 5,647,231 | A | 7/1997 | Payne et al. |
| 5,655,710 | A | 8/1997 | Kayahara et al. |
| 5,683,381 | A | 11/1997 | Carr et al. |
| 5,683,605 | A | 11/1997 | Matsuoka |
| 5,690,160 | A | 11/1997 | Sutton et al. |
| 5,690,614 | A | 11/1997 | Carr et al. |
| 5,722,947 | A | 3/1998 | Jeppsson et al. |
| 5,724,478 | A | 3/1998 | Thweatt |
| 5,729,653 | A | 3/1998 | Magliochetti et al. |
| 5,731,485 | A | 3/1998 | Crowe et al. |
| 5,790,752 | A | 8/1998 | Anglin et al. |
| 5,822,740 | A | 10/1998 | Haissig et al. |
| 5,836,908 | A | 11/1998 | Beden et al. |
| 5,875,282 | A | 2/1999 | Jordan et al. |
| 5,960,160 | A | 9/1999 | Clark et al. |
| 5,981,916 | A | 11/1999 | Griffiths et al. |
| 5,989,238 | A | 11/1999 | Ginsburg |
| 5,989,423 | A | 11/1999 | Kamen et al. |
| 6,014,498 | A | 1/2000 | Ikeda et al. |
| 6,043,469 | A | 3/2000 | Fink et al. |
| 6,069,343 | A | 5/2000 | Kolowich |
| 6,109,254 | A | 8/2000 | Reinke et al. |
| 6,133,547 | A | 10/2000 | Maynard |
| 6,139,528 | A | 10/2000 | Kistner et al. |
| 6,142,974 | A | 11/2000 | Kistner et al. |
| 6,146,359 | A | 11/2000 | Carr et al. |
| 6,175,688 | B1 | 1/2001 | Cassidy et al. |
| 6,178,291 | B1 | 1/2001 | Zenios et al. |
| 6,228,047 | B1 | 5/2001 | Dadson |
| 6,229,957 | B1 | 5/2001 | Baker |
| 6,236,809 | B1 | 5/2001 | Cassidy et al. |
| 6,245,218 | B1 | 6/2001 | Gibson et al. |
| 6,246,831 | B1 | 6/2001 | Seitz et al. |
| 6,254,265 | B1 | 7/2001 | MacDonald |
| 6,257,265 | B1 | 7/2001 | Brunner et al. |
| 6,259,074 | B1 | 7/2001 | Brunner et al. |
| 6,261,261 | B1 | 7/2001 | Gordon |
| 6,278,084 | B1 | 8/2001 | Maynard |
| 6,293,921 | B1 | 9/2001 | Shinmoto et al. |
| 6,348,146 | B1 | 2/2002 | Gibson et al. |
| 6,839,509 | B2 | 1/2005 | Kuebler et al. |
| 6,850,699 | B2 | 2/2005 | Kuebler et al. |
| 6,869,538 | B2 | 3/2005 | Yu et al. |
| 6,894,254 | B2 * | 5/2005 | Hauschulz ................ 219/506 |
| 7,057,141 | B1 | 6/2006 | Moy |
| 7,158,719 | B2 * | 1/2007 | Cassidy ................ 392/494 |
| 7,175,606 | B2 * | 2/2007 | Bowman et al. ............ 604/29 |
| 7,193,187 | B2 | 3/2007 | Chen et al. |
| 7,261,557 | B2 * | 8/2007 | Gill et al. ................ 431/328 |
| 2002/0045851 | A1 | 4/2002 | Suzuki et al. |
| 2002/0081109 | A1 | 6/2002 | Mitsunaga et al. |
| 2003/0000939 | A1 | 1/2003 | Faries et al. |
| 2003/0114795 | A1 | 6/2003 | Faries et al. |
| 2004/0082903 | A1 * | 4/2004 | Micheli ................ 604/29 |

* cited by examiner

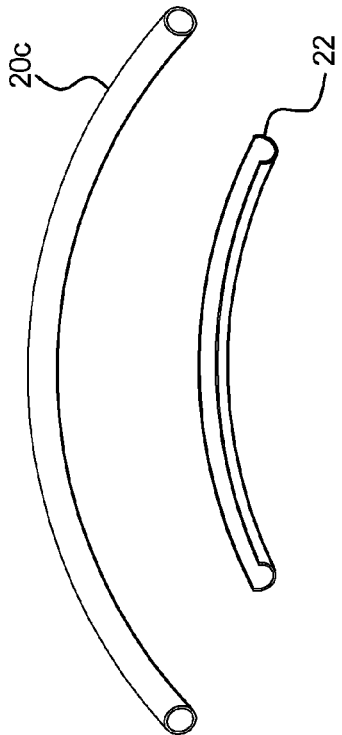
FIG. 3
FIG. 2
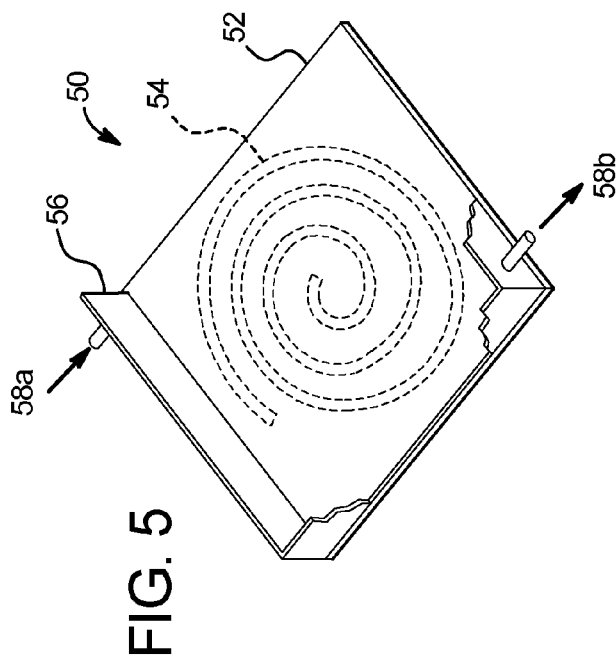
FIG. 5
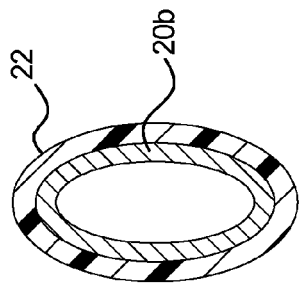
FIG. 4
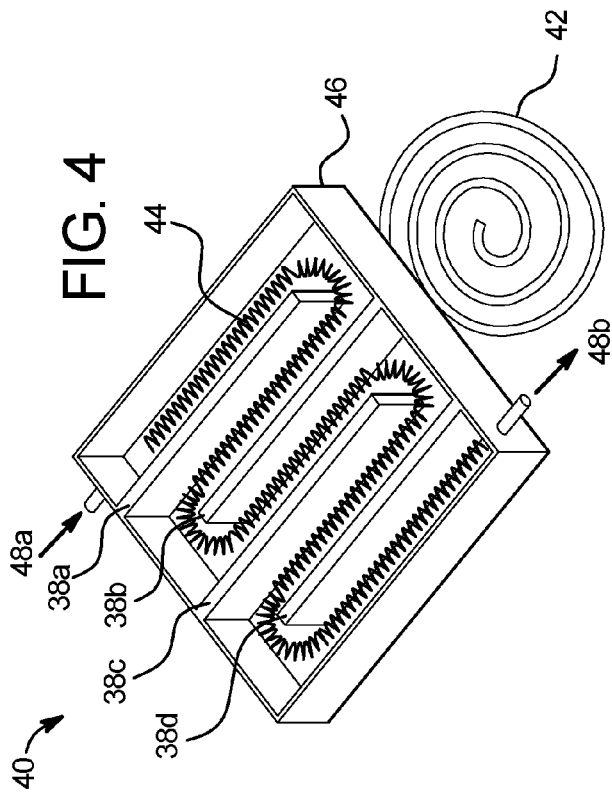

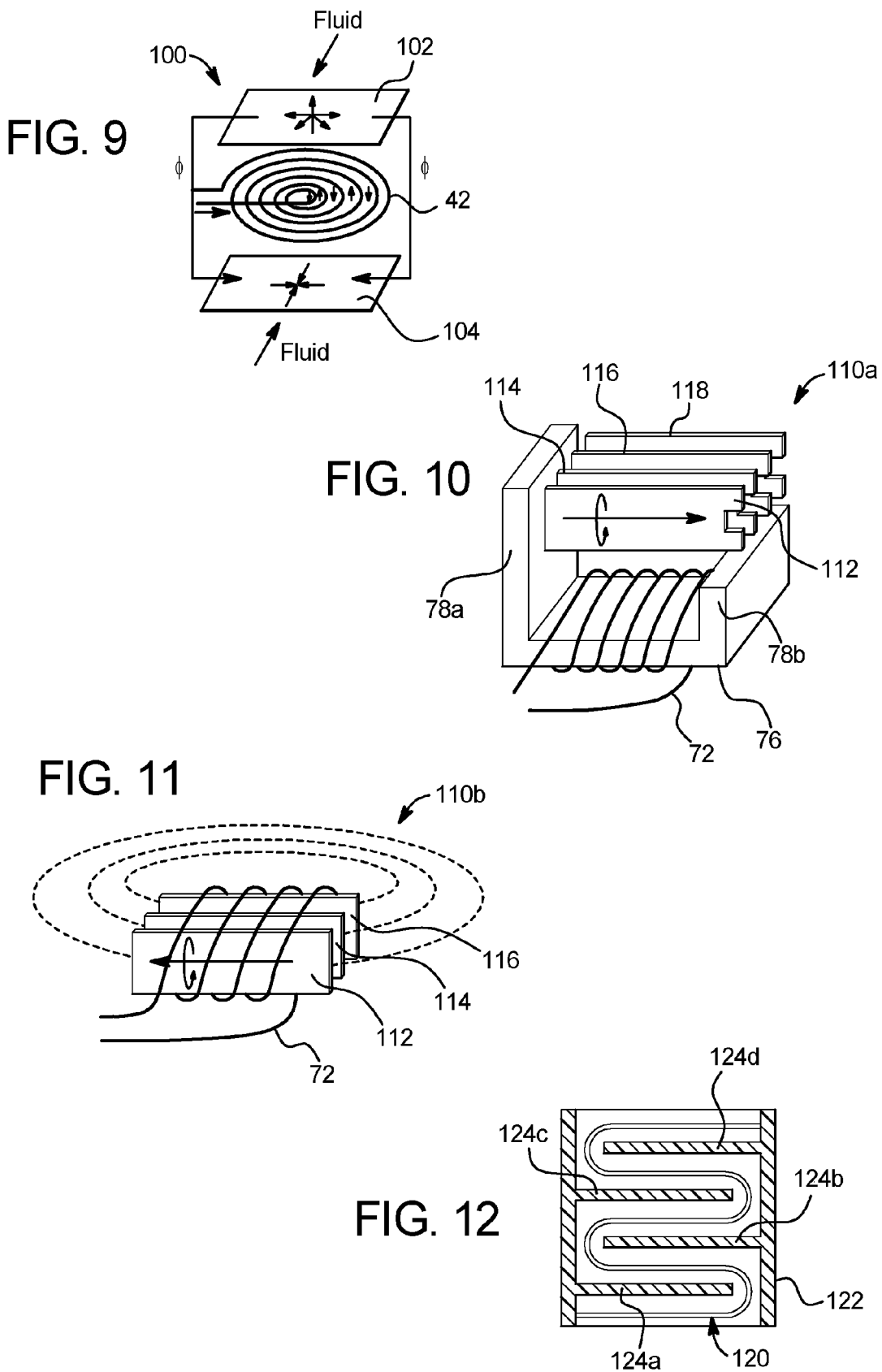

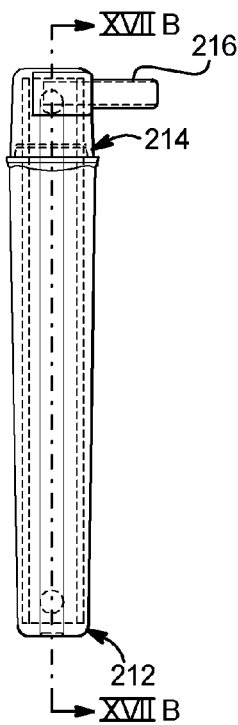
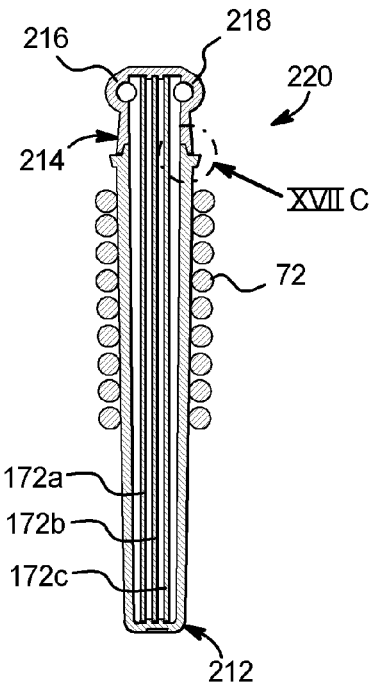
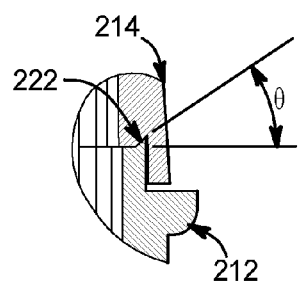
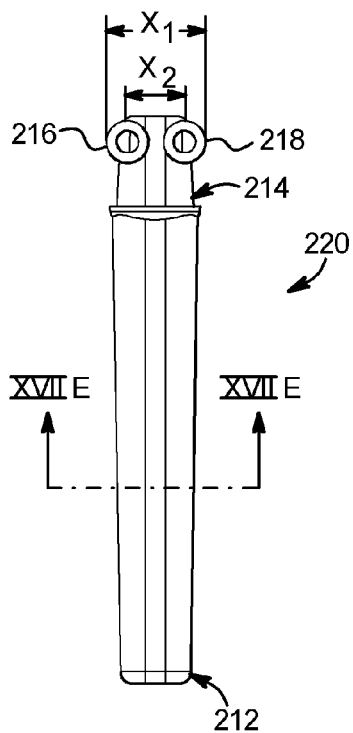
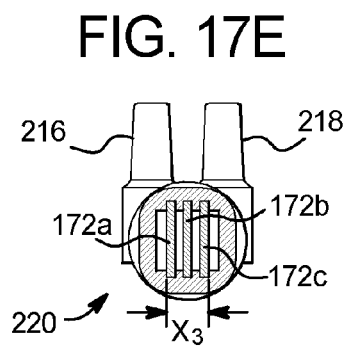
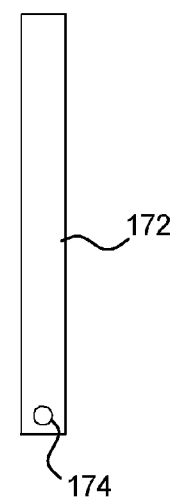

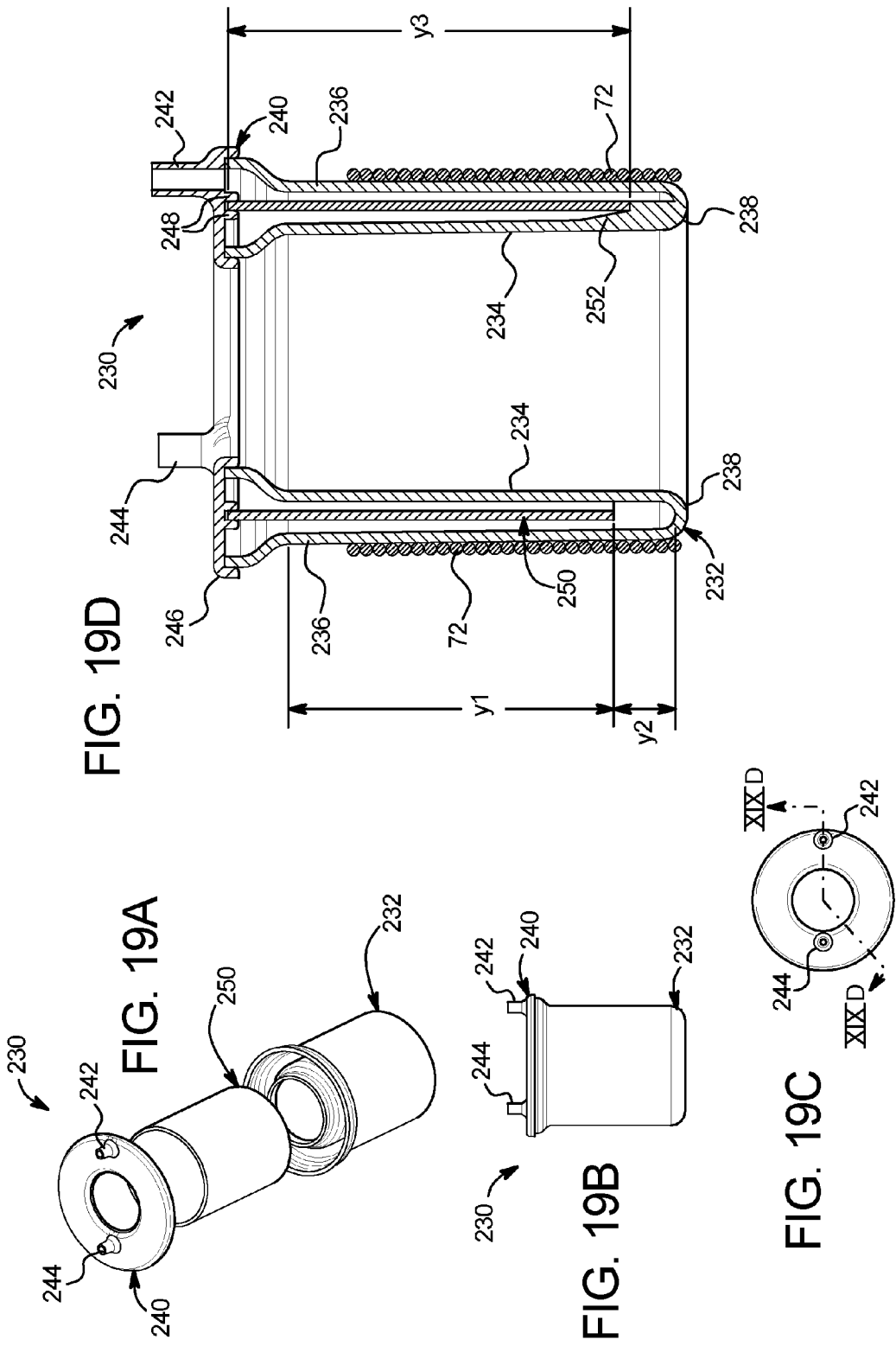

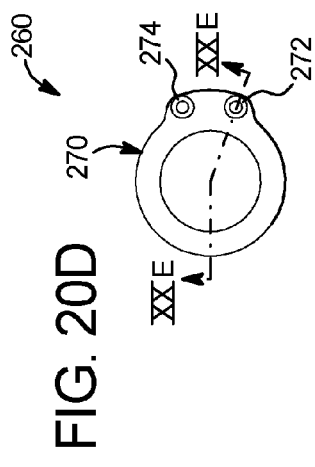
FIG. 20D
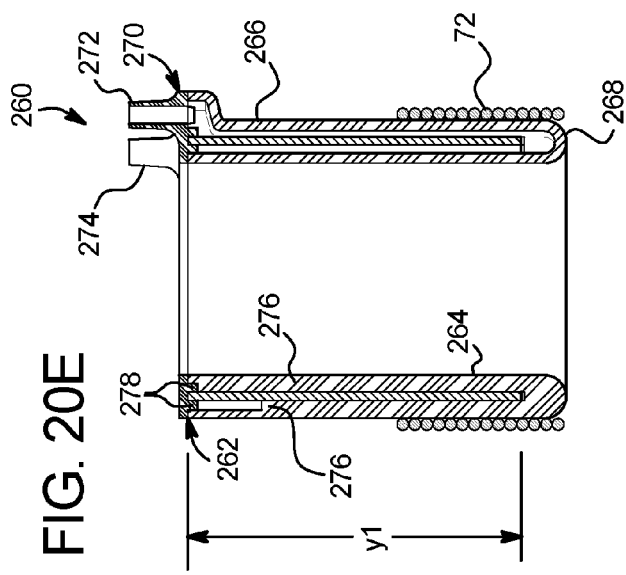
FIG. 20E
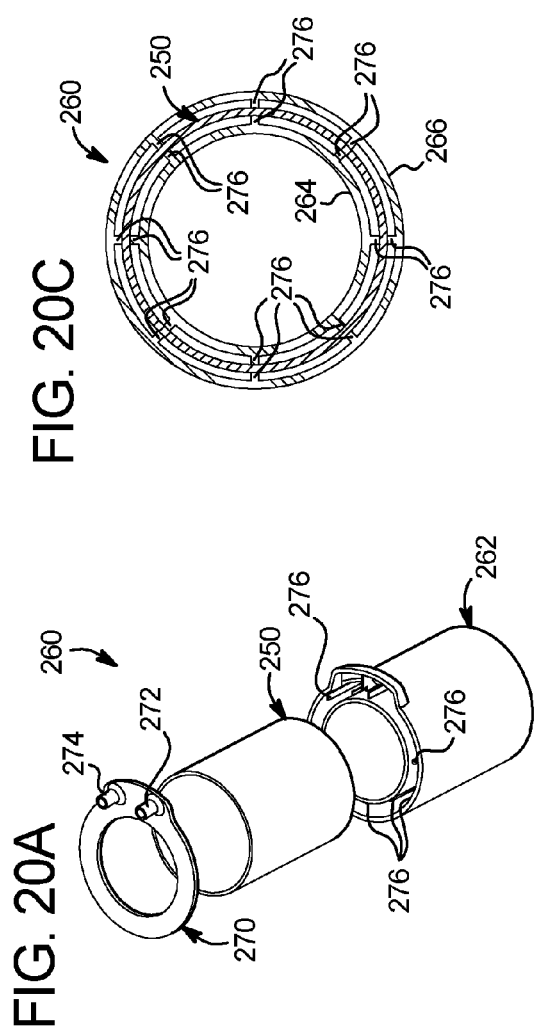
FIG. 20C
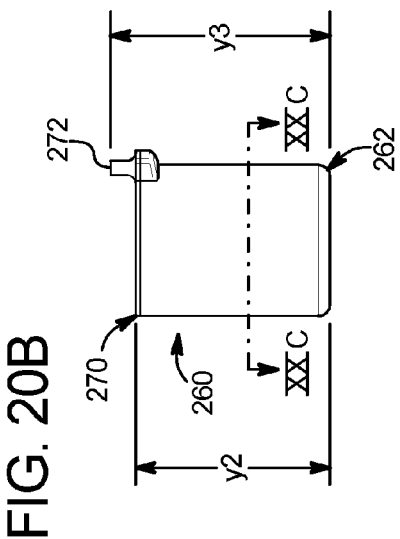
FIG. 20B
FIG. 20A

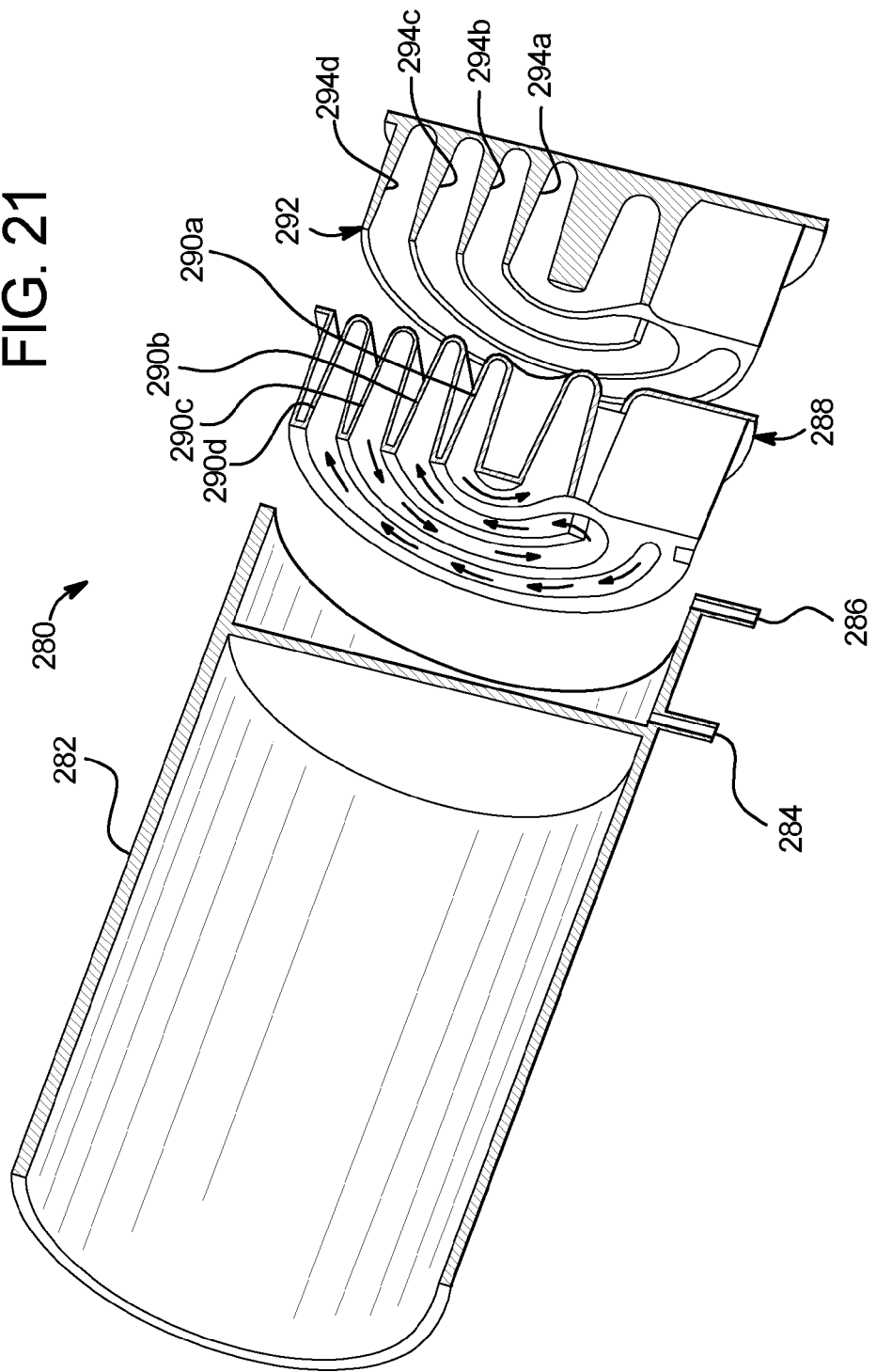

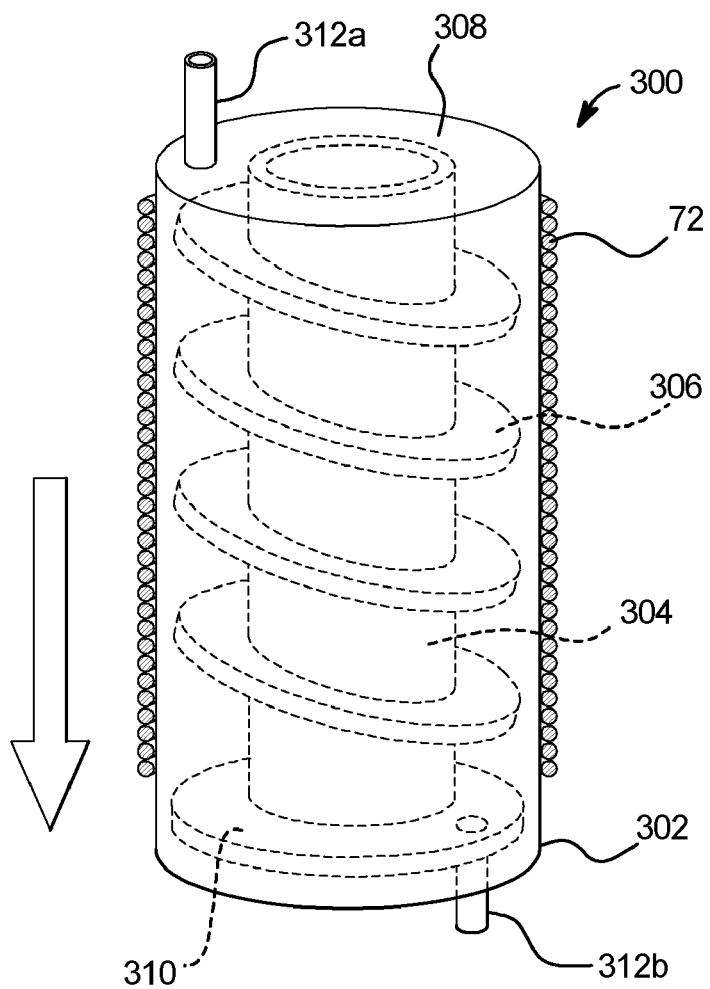
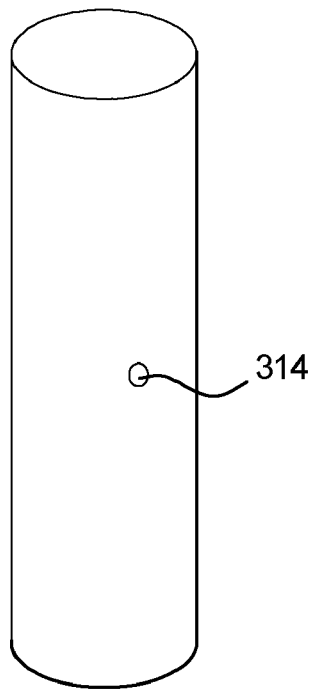
FIG. 22

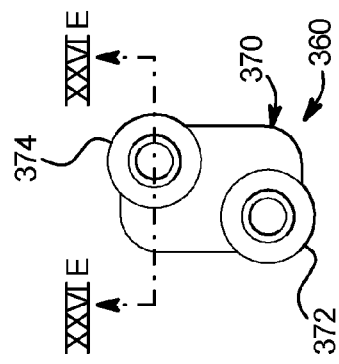
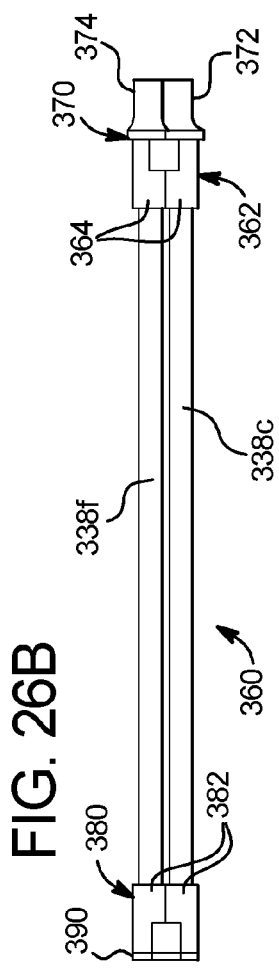
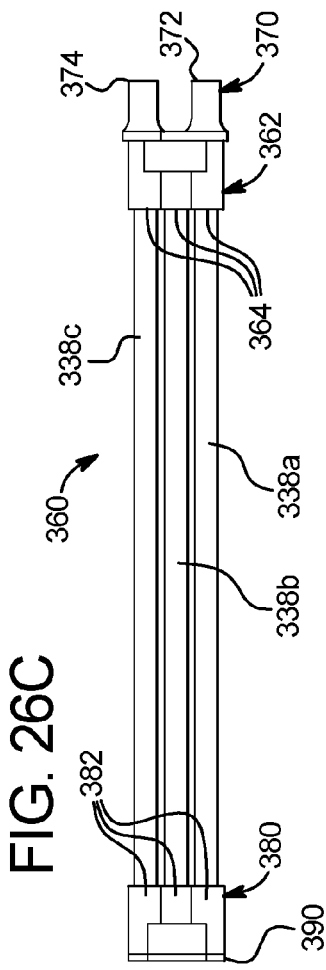
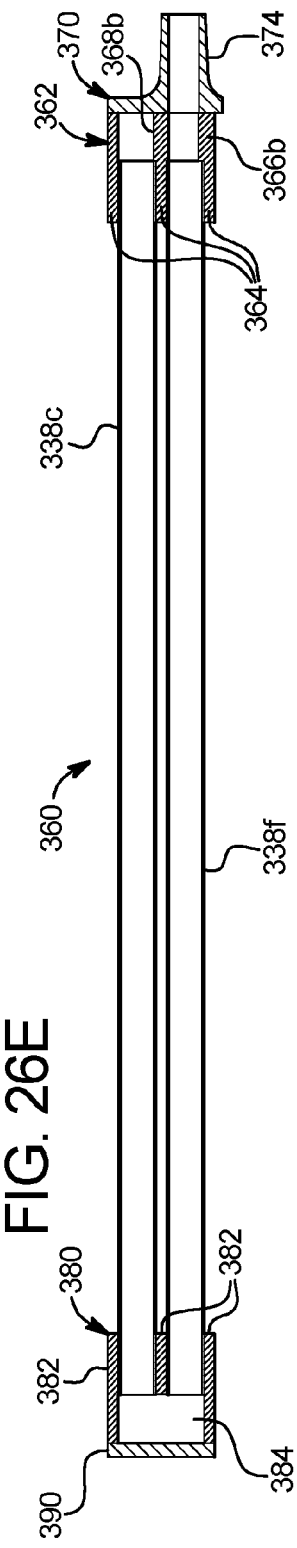

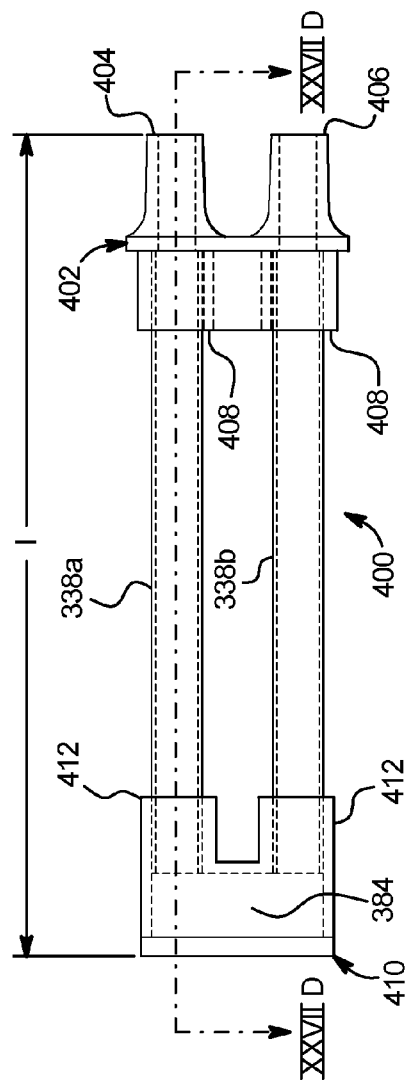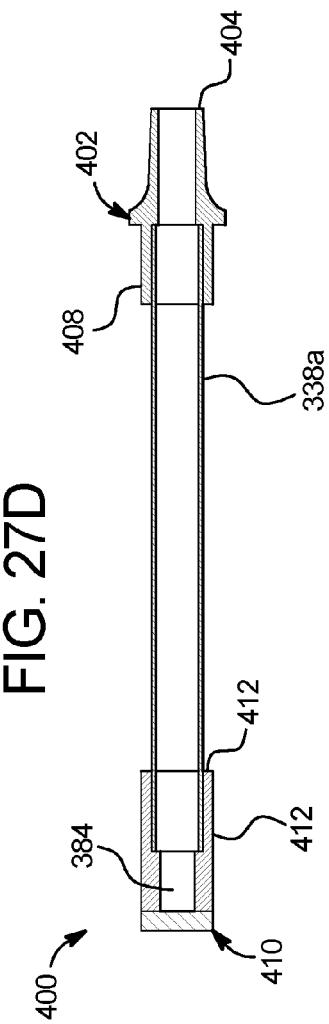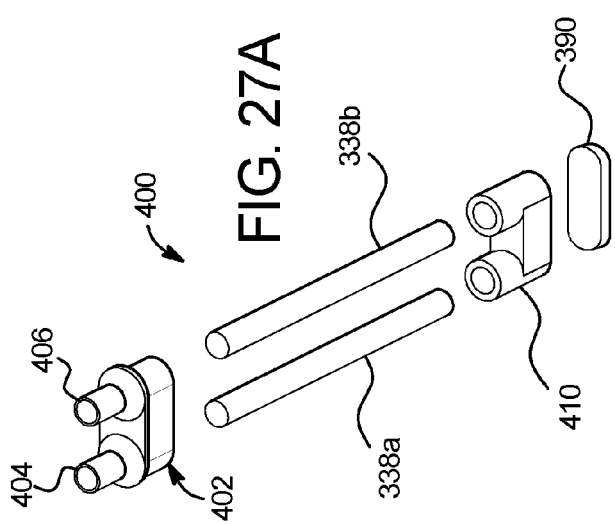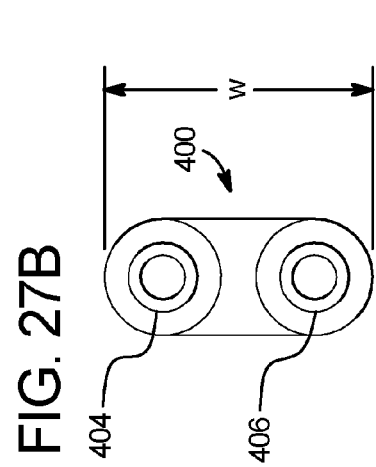

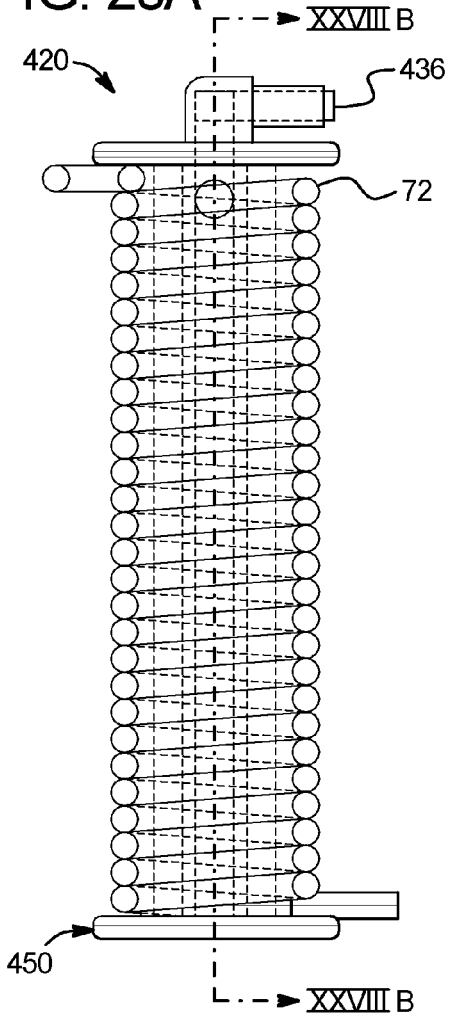
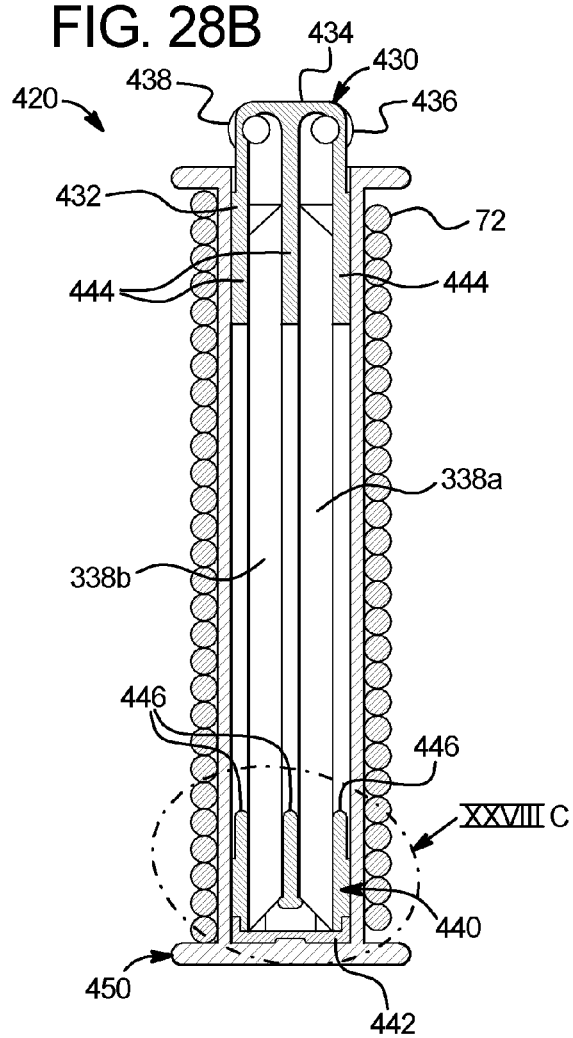
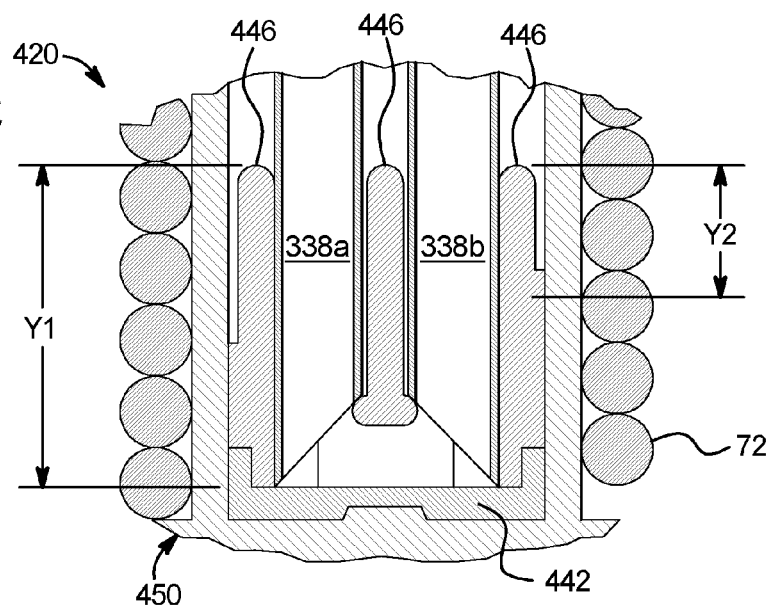
FIG. 28A
FIG. 28B
FIG. 28C

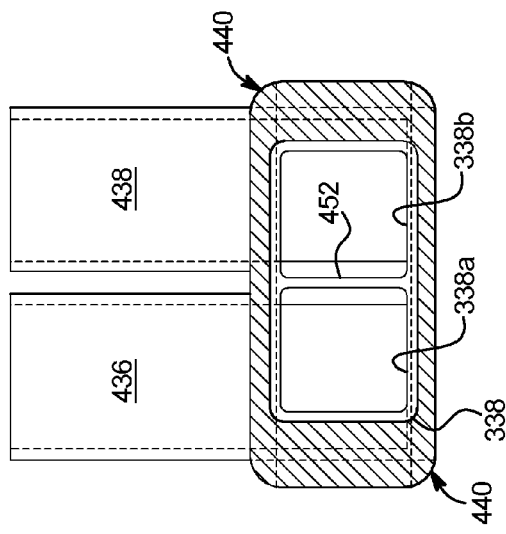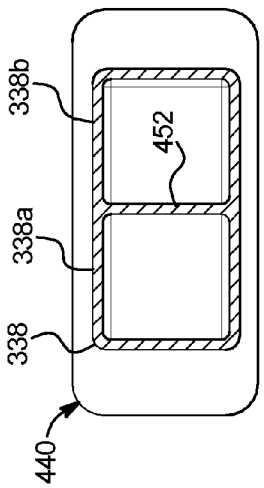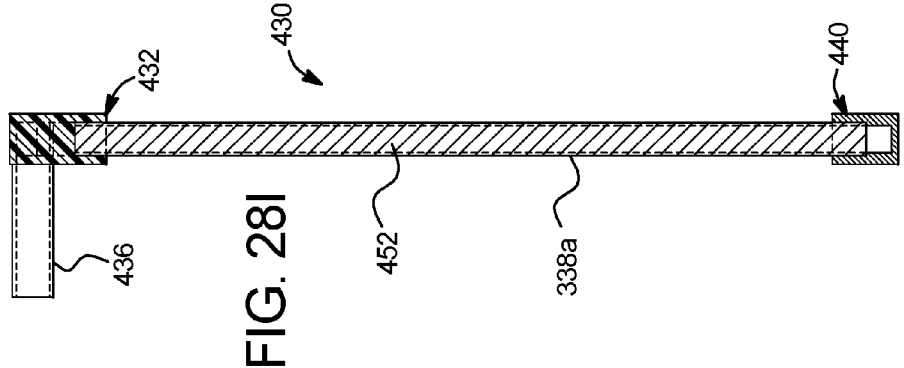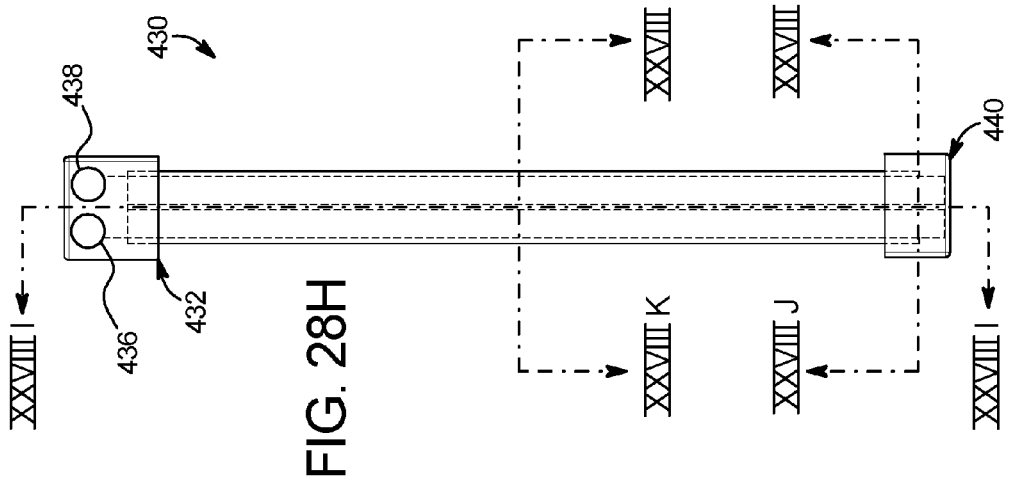

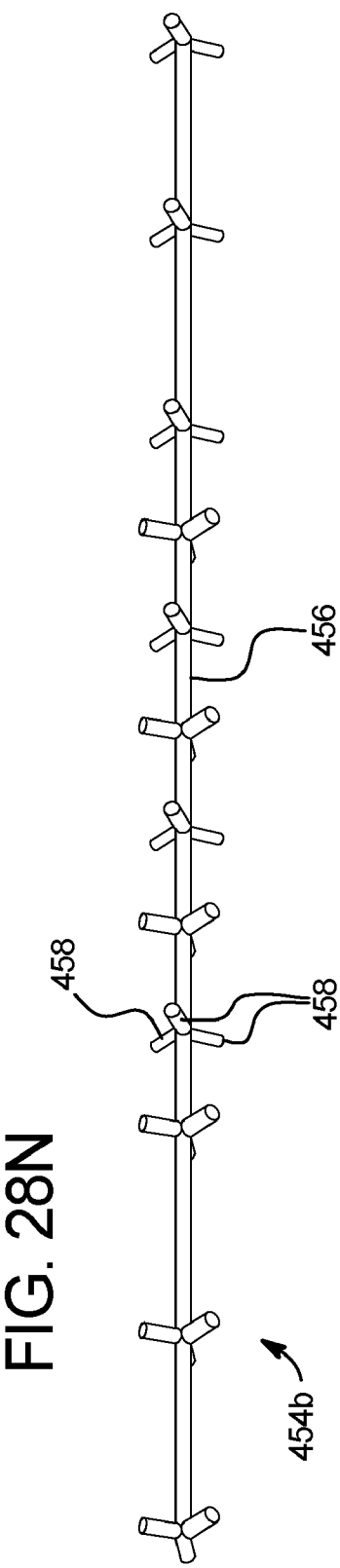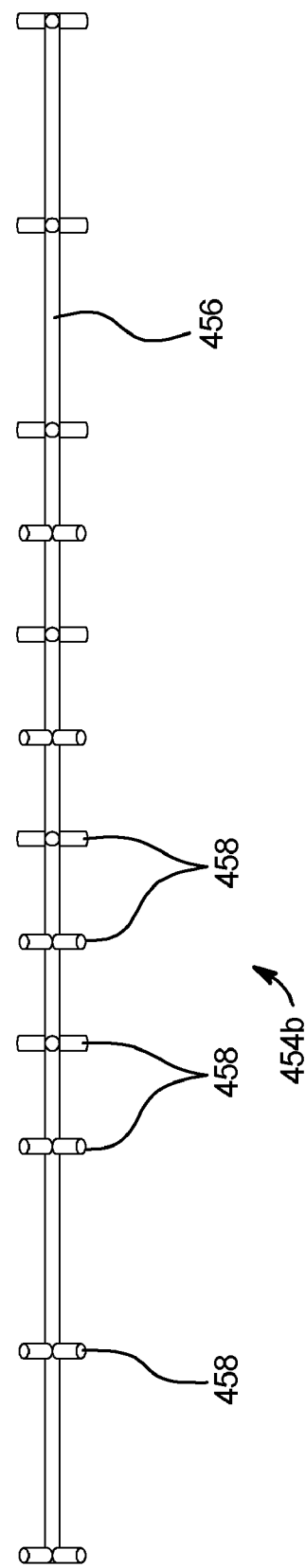

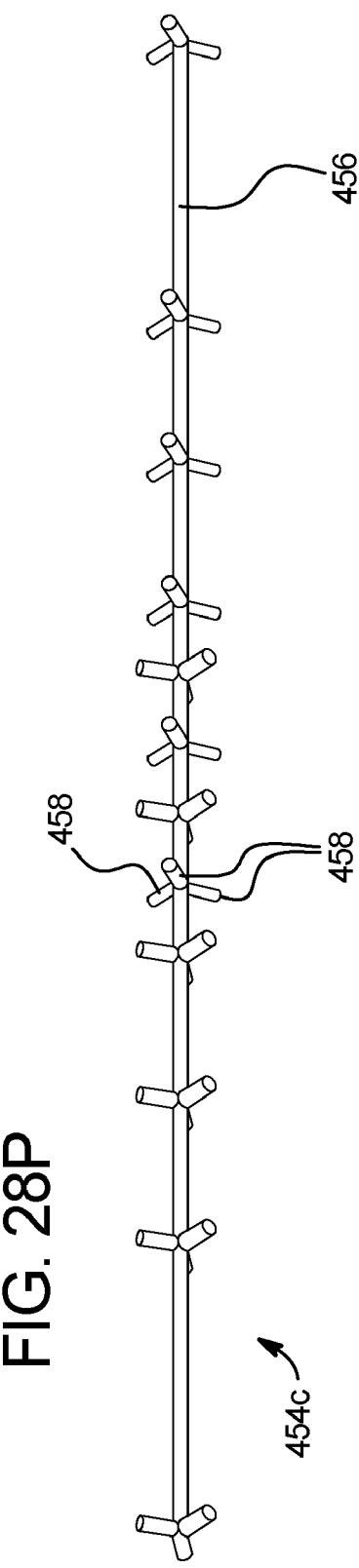
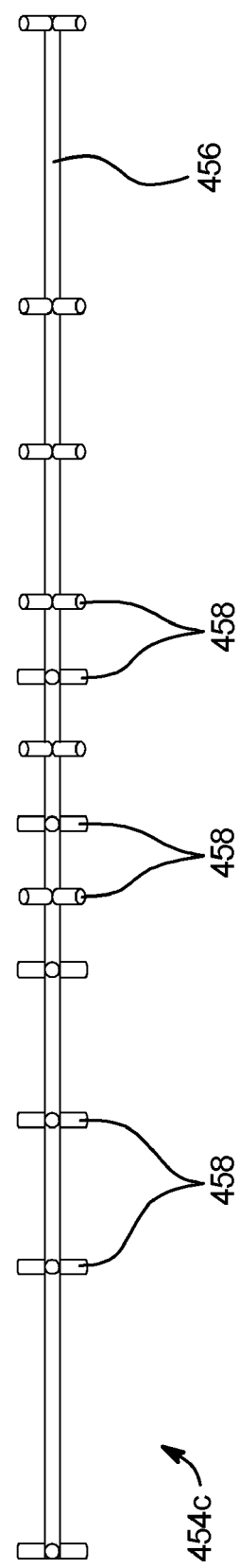
FIG. 28P
FIG. 28Q

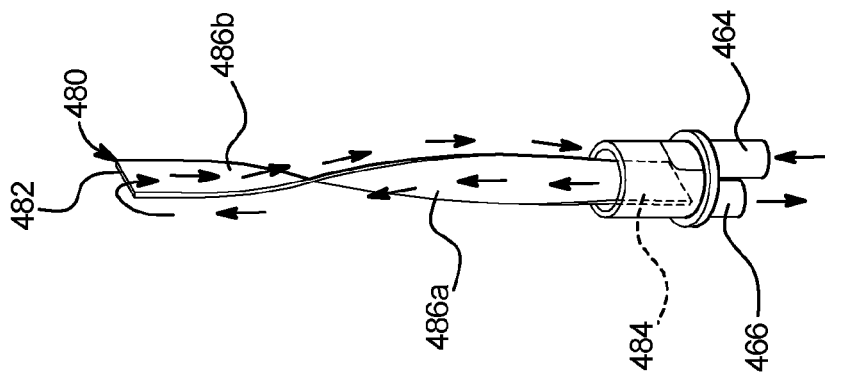
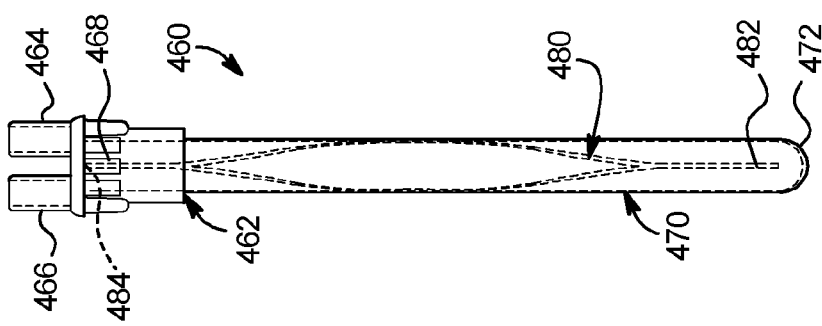
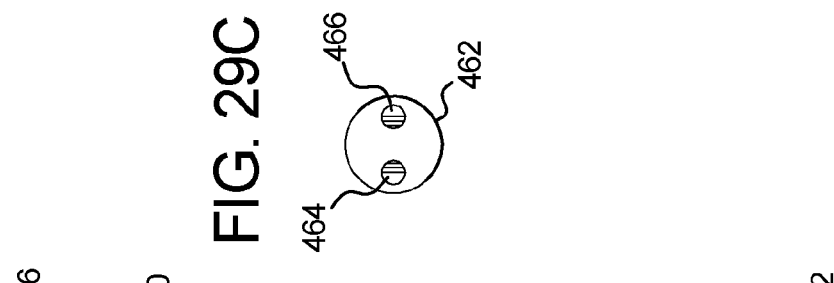
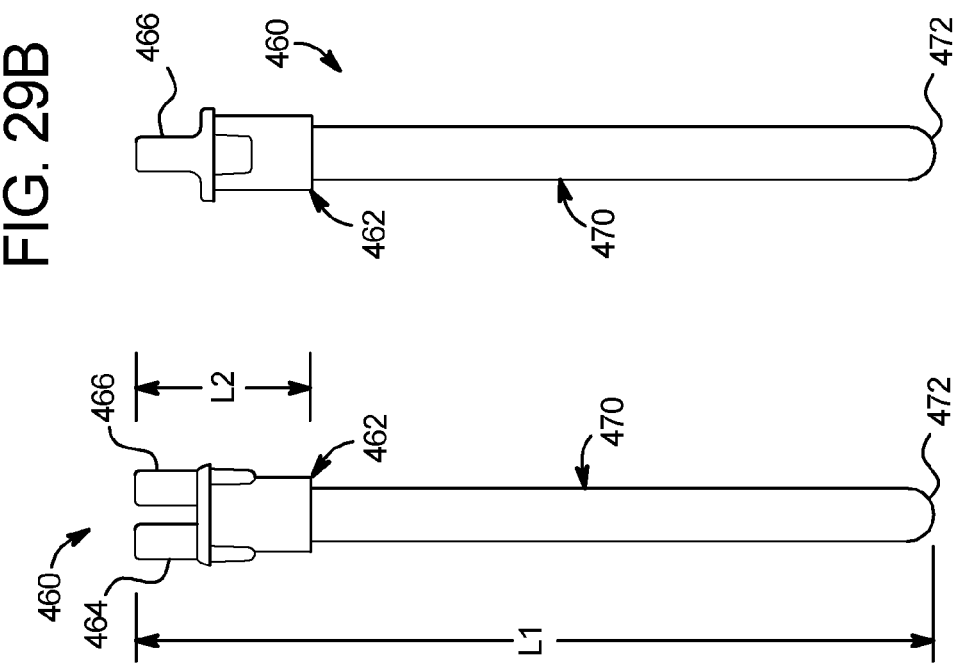

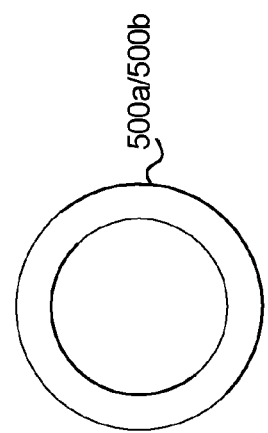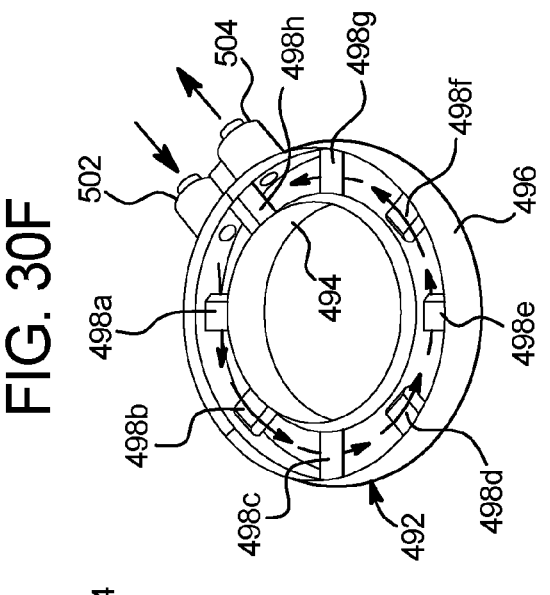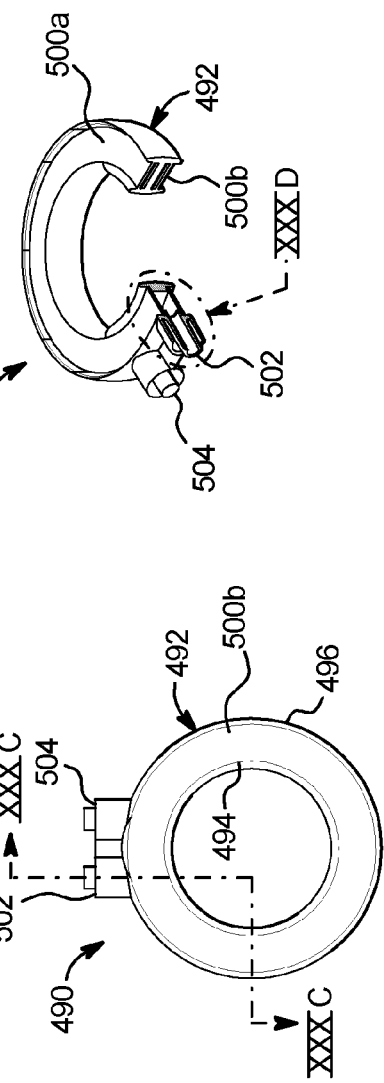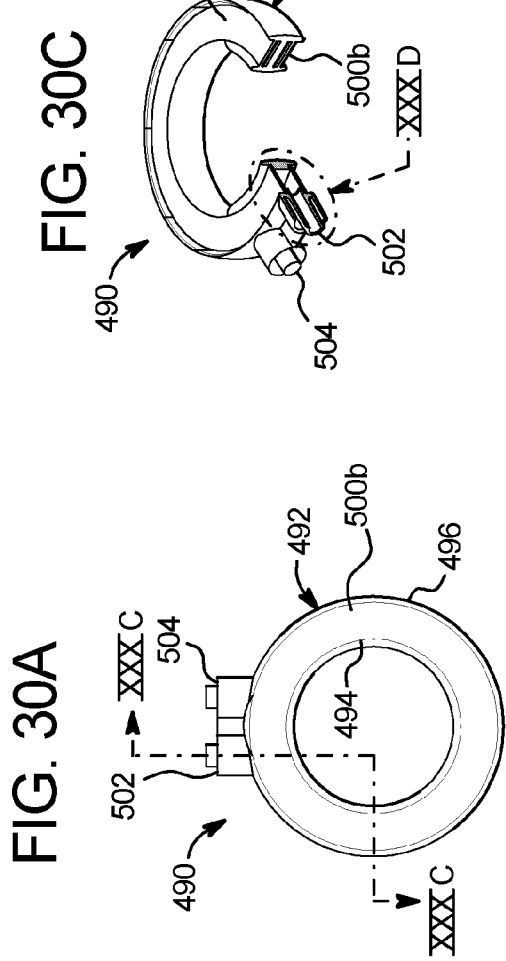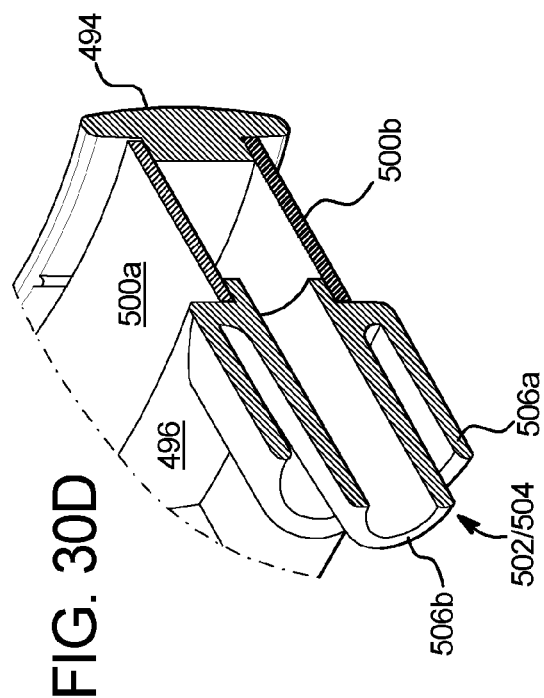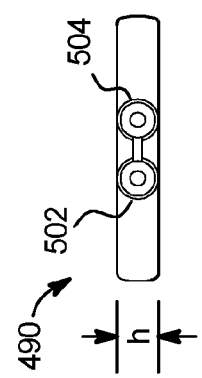

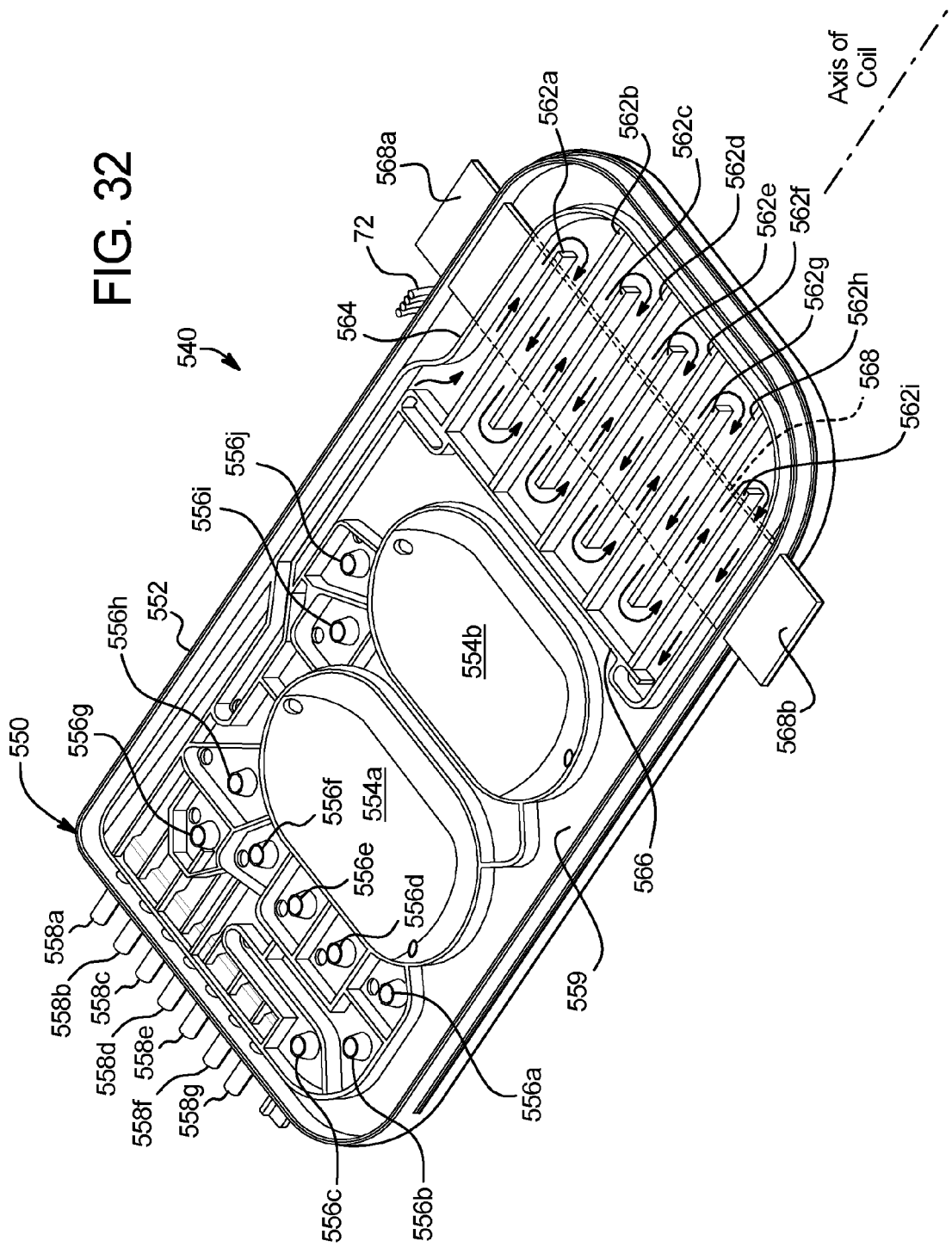

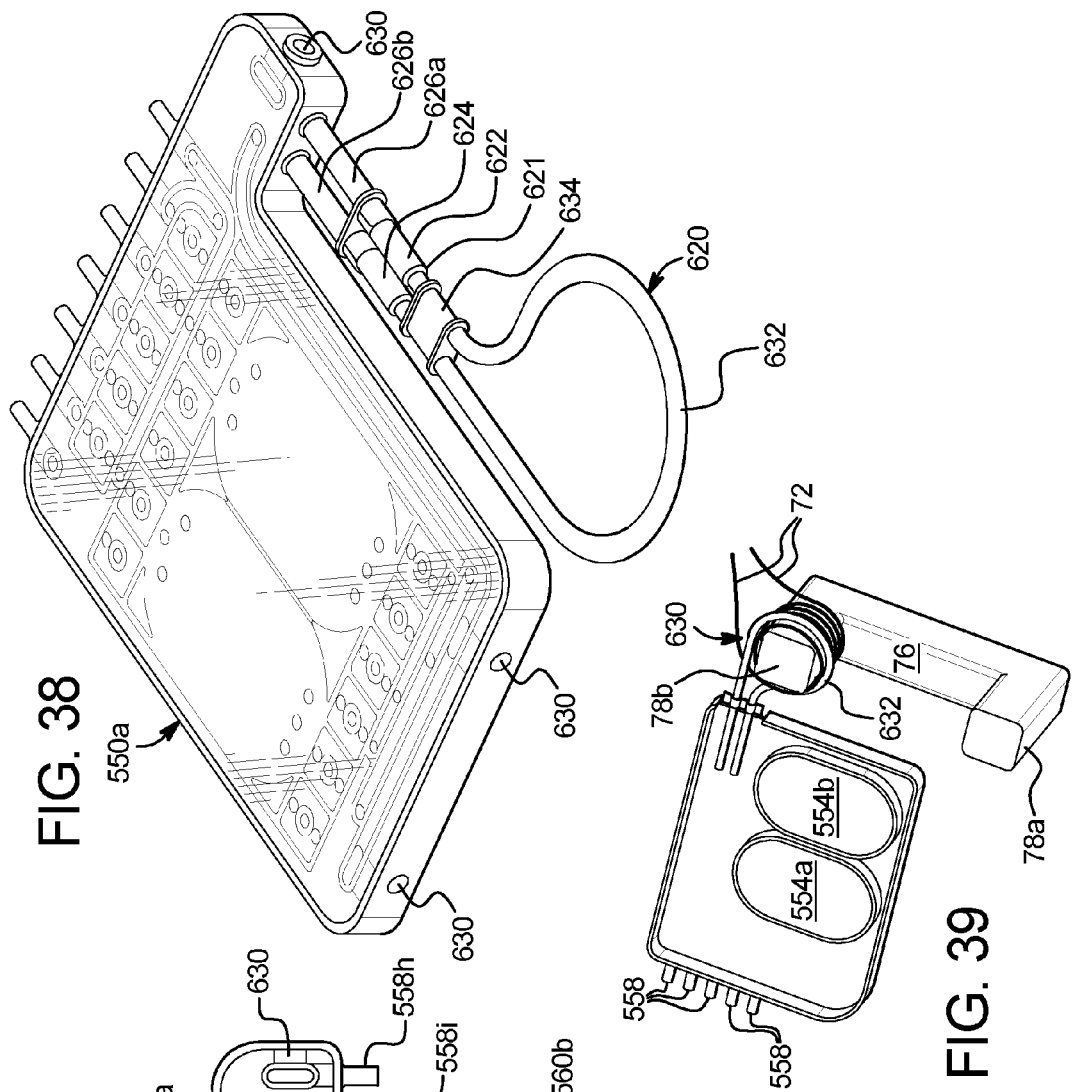
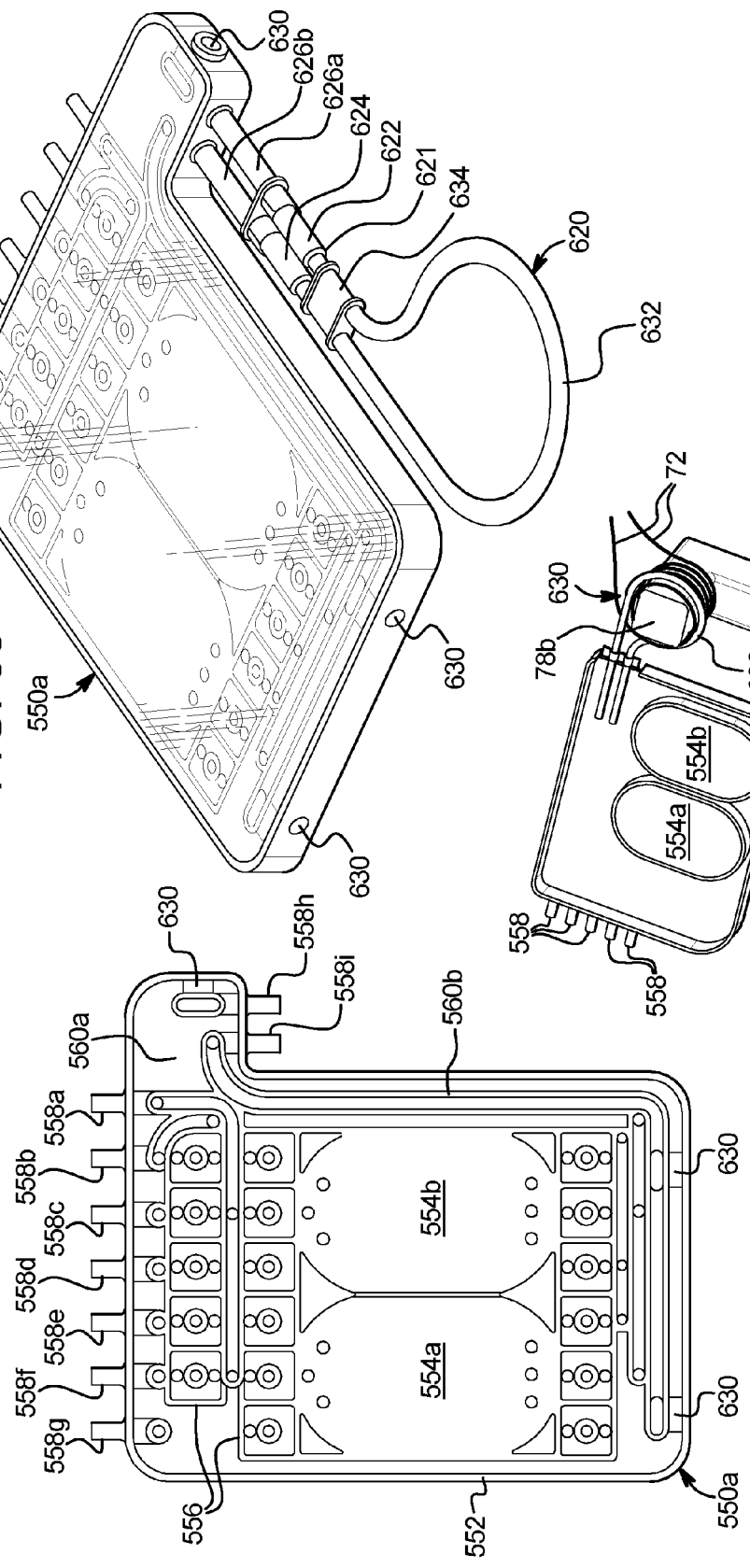
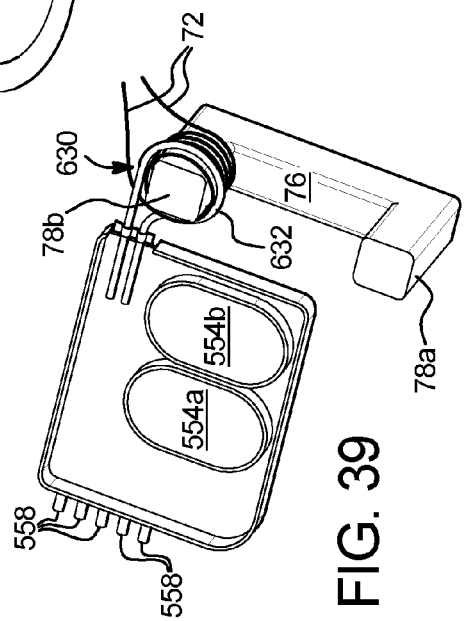

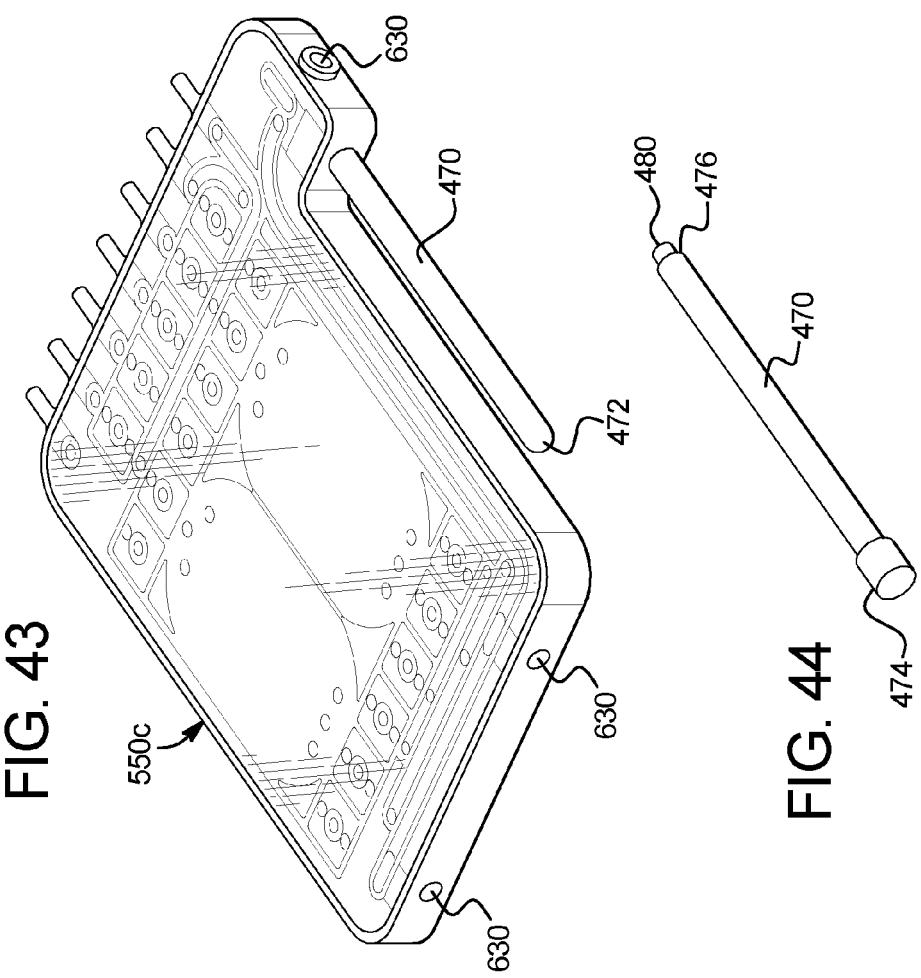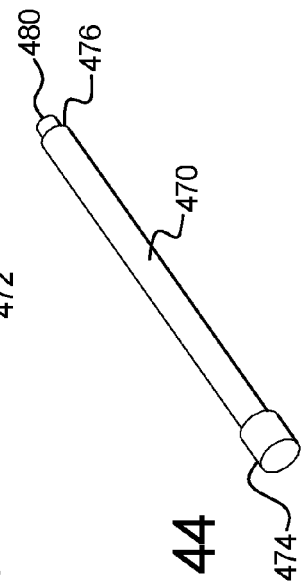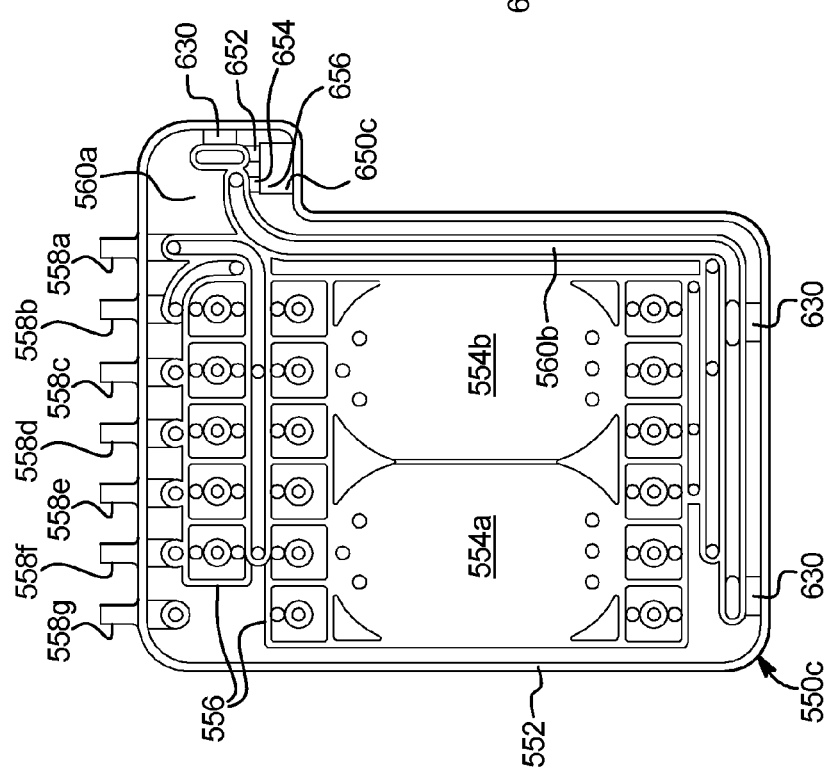

DIALYSIS FLUID HEATING ALGORITHMS

BACKGROUND

The present disclosure relates generally to medical fluid systems and more specifically to fluid heating for dialysis systems.

Due to various causes, a person's renal system can fail. Renal failure produces several physiological derangements. It is no longer possible to balance water and minerals or to excrete daily metabolic load. Also, toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normally functioning kidneys would otherwise remove. Dialysis treatment for kidney function replacement is critical to many people because the treatment is life saving.

One type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including automated peritoneal dialysis ("APD"), tidal flow dialysis and continuous flow peritoneal dialysis ("CFPD").

Automated peritoneal dialysis ("APD") is generally a batch therapy, which includes drain, fill, and dwell cycles. APD machines or "cyclers", however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity and for the transfer of waste, toxins and excess water to take place. The source can be multiple sterile dialysate solution bags.

APD machines pump spent dialysate from the peritoneal cavity, though the catheter, and to the drain. As with the manual process, several drain, fill and dwell cycles occur during dialysis. A "last fill" occurs at the end of CAPD and APD, which remains in the peritoneal cavity of the patient until the next treatment.

With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity, through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroducing the dialysate into the peritoneal cavity. Additional sensors are employed to monitor the removal of ammonia. CFPD systems are typically more complicated than batch systems.

All of the above systems require the dialysate to be heated to a desired temperature, e.g., body temperature. Known systems for heating dialysis fluid have been less than ideal for a number of reasons. Some systems require large amounts of energy and higher temperatures, which can overheat the dialysate if flow of the dialysate is stopped. Also, some heating systems force a dialysate pump to be located upstream of the heater. This can be disadvantageous for some pumps that measure fluid volume and generate a volume measurement error related to fluid temperature. Further, measuring the temperature of the dialysate in some heating systems is difficult due to a high thermal resistance of a plastic film through which the fluid temperature is measured.

SUMMARY

The heating systems and methods described herein are described in connection with dialysis and in particular peritoneal dialysis. It should be appreciated however that the systems and methods are also applicable to any type of dialysis, such as hemodialysis ("HD"), hemofiltration ("HF"), hemodiafiltration ("HDF"), a continuous renal replacement therapy ("CRRT") and to other medical fluid heating systems.

In one primary embodiment, the heating systems are inductive heating systems. The inductive systems and methods described herein generally use a relatively small disposable heating module, which can be heated to lower temperatures than with previous heaters due to its improved efficiency. The inductive systems and methods can use a metal tube or baffle (e.g., straight or cylindrical) or multiple tubes or baffles that are relatively rigid and that will not collapse under negative fluid pressure, allowing an associated medical fluid pump to be located either upstream or downstream from the heating section.

Also, the heating elements are in direct thermal contact with the fluid, allowing the outlet temperature of the fluid to be very closely approximated via a measurement of the tubing temperature near the fluid outlet. This measurement along with an inlet fluid temperature and the fluid flowrate allow the power supplied to the heater to be controlled to generate a desired temperature as described below.

Further, because induction heating systems transfer energy from a primary coil of a transformer to a secondary coil of a transformer with a magnetic field, and the primary coil of the transformer does not have to contact the secondary coil of the transformer, the secondary coil can be placed inside the disposable and in direct contact with the dialysis fluid being heated. Here, the secondary coil is termed a susceptor because it is a part of what is heated to in turn heat the fluid. The susceptor is in direct thermal contact with the fluid. The susceptor does not have to be heated to as high a temperature say as would a resistive plate in contact with the outside of the disposable heating pathway sheeting, which has a high thermal resistance. With this type of plate heating, a higher temperature differential is required to drive the same energy across the higher thermal resistance material. The thermal gradient across the metal is lower than that of plastic to drive the same amount of power into the fluid.

In the inductive systems described herein a magnetic field is generated using an electric circuit. The magnetic field is directed to a metal structure (called a susceptor) contained in the fluid path of the dialysis system disposable. The magnetic field generates an electric field in the metal structure, which in turn creates an electric current in the metal structure. The current flow is resisted by the bulk resistance of the metal structure, which creates heat in the metal structure due to the $i^2R$ power loss in the metal apparatus. Because in one embodiment an alternating electric current is created in the metal apparatus, the current flows mostly on the surface of the metal apparatus. Higher frequencies and the use of magnetic metal apparatuses tend to force the flow of current towards the surface of the metal part. Some of the inductive heating modules discussed herein have been configured to attempt to maximize surface area contact of the susceptor and fluid.

In various embodiments discussed below, the primary coil is a helical coil wound around the secondary coil, referred to herein as a susceptor. This configuration can have a coil length to coil diameter ratio of about two and a half to three, which has been found to result in an efficient coil. The helical coil in an embodiment is wound without spaces between turns to minimize unlinked magnetic flux. Smaller length to diameter ratio coils should be avoided to avoid end losses and low overall power efficiency. The coils shown below are also wound as close as feasible to the susceptor to maximize the area inside the coil filled by the susceptor and to reduce magnetic flux gap.

In one embodiment, the coil wire is Litz wire, which optimizes the alternating current resistance of the coil, especially in the relatively high frequency electric circuits used herein. Litz wire includes multiple strands of wire wound in parallel to reduce the increased resistance of a single (larger) diameter conductor coil due to the skin effect. In essence, multi-stranded coil wire increases the surface area of the wire used to produce the coil without increasing the outside diameter of the wire coil, reducing the amount of the coil conducting little current.

Various embodiments discussed herein also provide a structure (e.g., a magnetic core) configured to contain and direct the magnetic field toward the susceptor, which also improves the performance of the heating subsystem. The directing structure can be a ferrite material, which displays low magnetic field losses at high frequencies, at which the induction heaters operate typically. A helical coil is wound around the ferrite directing structure in various embodiments discussed below, providing flexibility in the loading of the disposable heating modules, as shown and discussed in detail below.

In most of the embodiments described herein, the secondary coil contacts the dialysis fluid directly (here secondary coil is a susceptor and part of the disposable). In one alternative embodiment, the secondary coil does not contact the fluid directly (here secondary coil is not a susceptor or part of the instrument). Instead, a current is induced in the secondary coil outside of the fluid heating module. The secondary coil is in turn connected electrically to a conductive module in contact with the fluid. The current from the secondary coil heats the separate module due to the $i^2R$ power loss in the separate module. This embodiment is broken out below as a resistive type heating using the secondary coil of a transformer to heat a conductive structure in the fluid heating pathway resistively.

In a further alternative embodiment, a separate metal heating module, e.g., tube, is placed in direct contact with an instrument heater, such as a resistive heater, and is heated primarily through conduction.

The tubing is modified in various embodiments to enhance the overall heat transfer efficiency of the system. For example, the tubing can have a texture on its surface, which increases the surface area of the tubing contacting the fluid. Alternatively, the tubing is flattened or bent, e.g., from round to elliptical, so that the fluid travels through a wider and thinner cross section of the tubing to increase the surface area to fluid volume ratio of the tubing. The fluid pathway of the flattened tubing is made thinner so that a distance and corresponding temperature gradient between the fluid at the inner wall of the tubing and the middle of the tubing (where the fluid is the coolest) is lessened.

The heating system also contemplates filling the cross section of the tubing with conductive particles, e.g., metal spheres, which can be sintered to each other and to the inside surface of the tubing, to form a high surface area to fluid volume section of tubing to increase the surface area to fluid ratio. For example, preliminary calculations of a four mm inside diameter tube section by 8.1 cm long, holding 0.4 mm spheres, would produce a contact surface area of about 100 mm square, and provide a fluid volume of only about 0.345 ml. The advantages of the metal filler heating system include ease of heating a smaller tube section, forming a smaller disposable heating section and providing a heating section that is easier to assemble to other portions of the dialysis system disposable.

In inductive systems that induce an electric current through the susceptor, the system can measure the voltage drop across the susceptor and current running through the susceptor to determine the electrical resistance of the susceptor. Knowing the initial resistance, temperature and temperature coefficient of the metal susceptor, the system can calculate the average temperature of the susceptor by measuring its resistance using this method quicker than measuring its temperature through a typically slow responding contact temperature sensor. This method of temperature measurement can also be used in the resistive heating system described above, which uses the secondary coil to drive current through the metal heater located in the disposable.

The initial susceptor temperature is determined in one embodiment by measuring the susceptor temperature using another calibrated temperature sensor (such as a diode, thermistor, integrated circuit sensor, infrared sensor, or resistance temperature device ("RTD") in thermal contact with the susceptor (possibly using the fluid in the system to insure thermal contact between the susceptor and the calibrated temperature sensor). The initial susceptor resistance is made when fluid is not being heated. The initial resistance is dependent on susceptor configuration, e.g., tube wall thickness, which can vary slightly from module to module. Accordingly, a set-up calibration procedure is performed at the beginning of each treatment to match a temperature with a resistance for a given disposable.

The temperature coefficient of the metal susceptor is a function of the metal and not the configuration of the metal. For example, the coefficient for a particular type of stainless steel can be 0.001 Ohm/° C. regardless of the configuration of the module using the metal. Knowing one data point and the temperature coefficient provides enough information for determining different susceptor temperatures for different measured resistances.

The system can use the average temperature (i) as a benchmark to prevent overheating of the tube or (ii) to calculate the average temperature of the fluid in contact with the tube. Even if the average temperature of the tube does not deliver the exact or instantaneous outlet temperature of dialysis fluid temperature, the system can use the average temperature of the tube in the safety control of the heating system. For example, if the susceptor or tube temperature jumps dramatically, it can be assumed that air has entered the heating module or that fluid flow has stopped. The heating system can be programmed to react in such a case to bypass the normal control of the module, remove power from the coil, and for example perform an air purge or flow occlusion routine, thereby preventing (i) air from reaching the patient or the flow occlusion and (ii) the module from overheating.

The teachings discussed herein are not limited to the use of tubing. For example, a current could be induced into metal baffles or plates to produce $i^2R$ heating. Such a structure is produced for example by folding a single sheet of metal into the proposed shape similar to a cross-section of an accordion or bellows. The baffles can alternatively be separate structures with apertures formed in the separate plates to allow fluid to flow from one baffle section to the next. The metal baffles are bonded to a plastic housing in one embodiment.

Further alternatively, a cylindrical susceptor is provided. Other susceptors are shown below. A plastic housing can be provided for any of the examples discussed herein, e.g., overmolded around the sheet metal portion forming the fluid path.

In one embodiment, the tube, baffle or cylinder type susceptor is provided in a heating module. The heating module can be connected to a disposable cassette as shown in many examples below. Alternatively, the module is connected to a different part of the system disposable, e.g., in-line in a tube such as the patient tube or a supply tube. Further alternatively, the susceptor is integrated directly into a cassette, for example, and provided as a conductive baffles within the cassette.

As discussed above, average tubing or surface temperature can be used for safety control, e.g., to prevent overheating. Instantaneous fluid temperature can also be monitored and controlled closely because the metal heating surface of the tubing or baffles is in close thermal contact with the fluid. The external surface temperature of the metal heating plates or tubing allows for accurate determination of actual fluid temperature, which is in turn used to control the heater efficiently, e.g., reducing overshoot, as discussed in detail below.

While inductive fluid heating is discussed prominently in this application, many concepts disclosed herein apply to other types of fluid heating, such as resistive heating. In any case, the heating subsystem of the dialysis instrument is intended to be efficient. The heating subsystem is insulated to prevent heat from being transferred from the heater to the dialysis instrument. This reduces the inside ambient air temperature of the instrument, and reduces the amount of heat that the instrument has to remove from the inside of the instrument. Reducing the inside temperature of the instrument increases its reliability and reduces the operating temperature of components housed in the instrument. Such a configuration also yields lower energy costs for the user and a more environmentally friendly instrument.

The above-described advantages of increasing energy efficiency of the heater subsystem apply to all types of fluid heating including inductive, resistive using transformers, and pure resistive using direct contact between the resistive heater and heating pathway sheeting. The heating system, regardless of which type, is capable of heating dialysis fluid from about 22° C. to about 37° C. at a flowrate of about 250 milliliters/minute. Applicants strive to make the heating subsystem greater than 80% energy efficient and to limit wasted power to below 100 Watts.

Also discussed herein is a system for applying negative or positive pressure between a heating pathway or heating portion of a disposable dialysis fluid set and a corresponding heater to achieve a desired effect. For example, negative pressure can be applied during heating to help increase surface contact between the fluid heating pathway and one or more heating plates. Positive pressure can be applied at a time in which it is desirable to purge the fluid from the fluid heating pathway, e.g., when air is detected in the fluid and the fluid needs to be discarded, or if a new type of fluid is to be introduced into the system and the old fluid needs to be flushed as much as possible. While the pressurized heating system may lend itself more to resistive plate heating, the system can be used in inductive heating for example when a fluid heating module housing the susceptor of the inductive system is flexible, e.g., has a flexible sheet, or has such a flexible component.

Further discussed herein is a control scheme or algorithm applicable to any of the types of fluid heaters discussed herein. The control scheme has a feedforward portion and a feedback portion. The feedforward portion produces a course determination of a power setpoint (heater is controlled via adjusting power to the heater in one embodiment) The course setting of the feedforward portion of the control scheme attempts to allow the outlet fluid temperature of the fluid to reach a desired temperature without the use of feedback. This in turn allows traditional feedback loop limitations, such as temperature overshoot and delay in reaching the desired temperature, to be minimized. The feedforward determination can be made using a table correlating power setpoint to initial fluid temperature, final fluid temperature and flowrate. Alternatively, the feedforward determination is made using the underlying equations used to generate the table.

After the setpoint is determined initially via the feedforward portion of the heating control scheme, a feedback loop is employed to fine tune the initial power setpoint to eliminate any error between desired fluid outlet temperature and the actual fluid outlet temperature. The feedback loop can apply one or more gain to the power setpoint, such as a proportional gain, integral gain or derivative gain ("PID") to adjust the power setpoint. Alternatively, the feedback loop modifies the feedforward determination, for example, increases a delta T used in the feedforward determination of power setpoint if the actual outlet fluid temperature is too low or decreases the delta T if the actual outlet fluid temperature is too high.

Based on the embodiments discussed herein, it is accordingly an advantage of the present disclosure to provide improved medical fluid heating systems and methods.

It is another advantage of the present disclosure to provide a fluid heating system that can use less energy and lower temperatures to achieve a desired fluid temperature.

It is a further advantage of the present disclosure to provide a fluid heating system that can be located upstream or downstream of an associated one or more medical fluid pump.

Still another advantage of the present disclosure is to provide a fluid heating system that can accurately detect outlet fluid temperature.

Yet a further advantage of the present disclosure is to provide a fluid heating system that reduces overheating.

Still a further advantage of the present disclosure is to provide a fluid heating system having an efficient heating control.

A still further advantage of the present disclosure is to provide a fluid heating system having a pressurized interface between a heating energy supply (resistive or inductive) and a dialysis fluid carrying portion in contact with the supply.

Moreover, it is an advantage of the present disclosure to provide a fluid heating system useable in any type of dialysis or renal failure therapy system, such as a peritoneal dialysis system or a hemodialysis system.

Additional features and advantages are described herein, and will be apparent from, the following Detailed Description and the figures.

BRIEF DESCRIPTION OF THE FIGURES

FIG. 2 is a side sectional view illustrating one embodiment for mating a conductive inductor coil with an electrically insulating housing.

FIG. 3 is a perspective view illustrating another embodiment for mating a conductive inductor coil with a thermally insulating housing.

FIG. 4 is a perspective view illustrating another embodiment for an inductive dialysis fluid heating system of the present disclosure using at least one pancake primary coil and a baffled secondary coil.

FIG. 5 is a perspective view illustrating a further embodiment for an inductive dialysis fluid heating system of the present disclosure using at least one embedded secondary coil.

FIG. 9 is a perspective view illustrating an embodiment for an inductive dialysis fluid heating system of the present disclosure using a pancake type primary coil and secondary coil plates.

FIG. 10 is a perspective view illustrating an embodiment for an inductive dialysis fluid heating system of the present disclosure using a spirally or helically wound primary coil, a flux directing core and a plurality of secondary coil plates.

FIG. 11 is a perspective view illustrating another embodiment for an inductive dialysis fluid heating system of the present disclosure using a spirally or helically wound primary coil and a plurality of secondary coil plates.

FIG. 12 is a plan view illustrating an embodiment for a secondary coil, which uses a single metal sheet folded to produce multiple baffles or turns with intervening insulating baffles.

FIG. 17A is a side elevation view of a yet another secondary coil fluid heating module of the present disclosure using multiple separate baffle plates.

FIG. 17B is a front-sectioned view of the heating module of FIG. 17A taken along line XVII B-XVII B of FIG. 17A.

FIG. 17C is a sectioned view of Detail XVII C of FIG. 17B.

FIG. 17D is a front elevation view of the heating module of FIG. 17A.

FIG. 17E is a bottom-sectioned view of the heating module of FIG. 17A taken along line XVII E-XVII E of FIG. 17D.

FIG. 17F is a side elevation view of one embodiment of a baffle plate of the module of FIG. 17A.

FIG. 19A is an exploded perspective view of various parts of one embodiment of an inductive cylindrical fluid heating module.

FIG. 19B is an elevation view of the inductive cylindrical fluid heating module of FIG. 19A.

FIG. 19C is a top plan view of the inductive cylindrical fluid heating module of FIG. 19A.

FIG. 19D is an elevation-sectioned view taken along line XIX D-XIX D of FIG. 19C.

FIGS. 20A is an exploded perspective view of various parts of another embodiment of an inductive cylindrical fluid heating module.

FIG. 20B is an elevation view of the inductive cylindrical fluid heating module of FIG. 20A.

FIG. 20C is a top-sectioned view of the inductive cylindrical fluid heating module of FIG. 20A taken along line XX C-XX C of FIG. 20B.

FIG. 20D is a top plan view of the inductive cylindrical fluid heating module of FIG. 20A.

FIG. 20E is an elevation-sectioned view taken along line XX E-XX E of FIG. 20D.

FIG. 21 is a perspective view of a further embodiment of an inductive cylindrical fluid heating module.

FIG. 22 is an elevation view of yet another embodiment of an inductive cylindrical fluid heating module.

FIGS. 26B and 26C are side views of the assembled fluid heating module of FIG. 26A.

FIG. 26D is an end view of the assembled fluid heating module of FIG. 26A.

FIG. 26E is a side-sectioned view of the assembled fluid heating module of FIG. 26A taken along line XXVI E-XXVI E of FIG. 26D.

FIG. 27A illustrates various parts of a further embodiment of a secondary coil fluid heating module of the present disclosure using multiple heating tubes.

FIG. 27B is a bottom end view of the assembled fluid heating module of FIG. 27A.

FIG. 27C is a side view of the assembled fluid heating module of FIG. 27A.

FIG. 27D is a side-sectioned view of the assembled fluid heating module of FIG. 27A taken along line XXVII D-XXVII D of FIG. 27C.

FIG. 28A is a side elevation view of yet another secondary coil fluid heating heater of the present disclosure using multiple heating tubes and a wound primary coil.

FIG. 28B is a front-sectioned view of the heater of FIG. 28A taken along line XXVIII B-XXVIII B of FIG. 28A.

FIG. 28C is a sectioned view of Detail XXVIII C of FIG. 28B.

FIG. 28H is a front elevation view of an alternative fluid heating module very similar to that of FIGS. 28A to 28G but instead employing a rectangular tube divided into first and second tube sections.

FIG. 28I is a side-sectioned view of the heating module of FIG. 28H taken along line XXVIII I-XXVIII I of FIG. 28H.

FIG. 28J is a bottom-sectioned view of the heating module of FIG. 28H taken along line XXVIII J-XXVIII J of FIG. 28H.

FIG. 28K is a top-sectioned view of the heating module of FIG. 28H taken along line XXVIII K-XXVIII K of FIG. 28H.

FIGS. 28N and 28O are perspective and side views of a second embodiment of a static mixer used in any of the tube fluid heating modules described herein.

FIGS. 28P and 28Q are perspective and side views of a third embodiment of a static mixer used in any of the tube fluid heating modules described herein.

FIG. 29A is a front elevation view of one embodiment of a secondary coil fluid heating module of the present disclosure using a single tube and twisted conductive baffle.

FIG. 29B is a side elevation view of the secondary coil fluid heating module of FIG. 29A.

FIG. 29C is a top plan view of the secondary coil fluid heating module of FIG. 29A.

FIG. 29D is a rear elevation view of the secondary coil fluid heating module of FIG. 29A showing the twisted baffle in hidden line.

FIG. 29E is a perspective view of a twisted baffle assembly of the fluid heating module of FIG. 29A.

FIG. 30A is a top plan view of one embodiment of a secondary coil fluid heating module of the present disclosure using conductive washers.

FIG. 30B is a front elevation view of the secondary coil fluid heating module of FIG. 30A.

FIG. 30C is a perspective view of the secondary coil fluid heating module taken along line XXX C-XXX C of FIG. 30A.

FIG. 30D is a perspective view of the Detail XXX D of FIG. 30C.

FIG. 30E is a top plan view of one embodiment of a washer heating plate used with the secondary coil fluid heating module of FIG. 30A.

FIG. 30F is a perspective view of one embodiment of an insulating housing portion of the secondary coil of FIG. 30A.

FIG. 32 is a perspective view of one embodiment of a fluid heating module integrated into a disposable pumping cassette.

FIG. 37 is a top plan view of one embodiment of a disposable pumping cassette having port connections for connecting to the fluid heating modules described herein.

FIG. 38 is a perspective view of the disposable cassette of FIG. 37 showing a further alternative fluid heating module connected to the cassette.

FIG. 39 is a perspective view of the disposable cassette and alternative fluid heating module of FIG. 38 showing the cassette and heating module in operable position with a magnetic core and primary coil of the dialysis instrument.

FIG. 42 is a top plan view of a further alternative embodiment of a disposable pumping cassette having a single embedded port connection for connecting to a single tube fluid heating module.

FIG. 43 is a perspective view of the disposable cassette of FIG. 42 showing a further alternative single tube fluid heating module connected to the cassette.

FIG. 44 is a perspective view of yet another alternative embodiment of a single tube fluid heating module, which is operable with the disposable cassette of FIG. 43.

DETAILED DESCRIPTION

As shown in many examples below, the present heating systems can operate with a fluid heating path of a disposable unit for use with a medical fluid system requiring heating, such as any type of renal failure therapy system, e.g., any type of peritoneal dialysis ("PD"), or any type of blood therapy including hemodialysis ("HD"), hemofiltration ("HF") and hemodiafiltration ("HDF").

Resistive Systems Using Transformer

Figure 1:
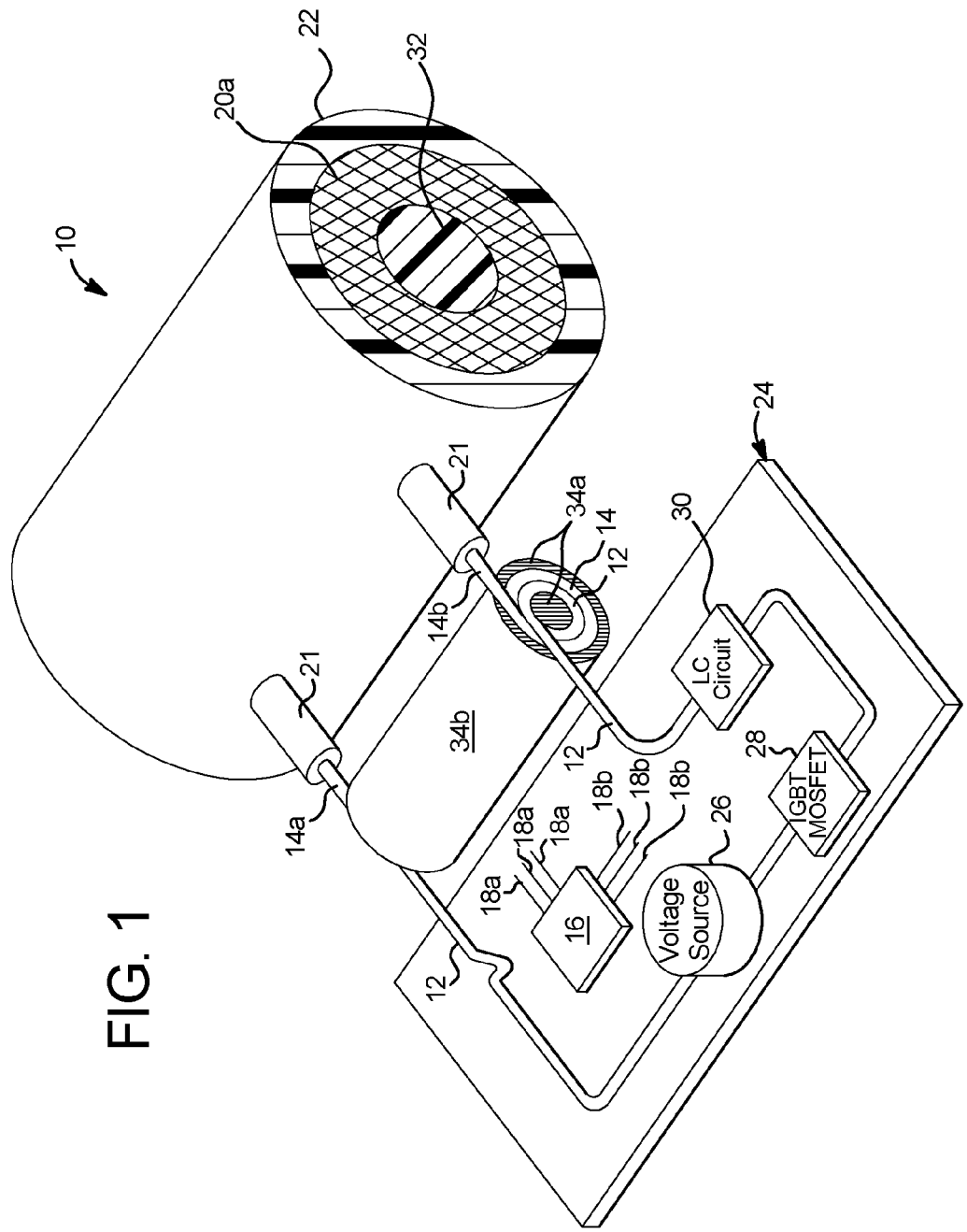
FIG. 1 is a perspective view illustrating one embodiment for an inductive dialysis fluid heating system of the present disclosure.

Referring now to the drawings and in particular to FIG. 1, system 10 illustrates another possible resistive embodiment using a transformer. Here, a piece of metal 20a is placed in the disposable, which is heated by passing a current through it. The current supplied by the transformer secondary winding is isolated electrically from the AC mains power source, which is connected to the primary winding. The instrument makes electrical contact with the disposable to allow the current from the transformer to pass though the metal contained in the disposable. Primary coil 12 and secondary coil 14 are located in the instrument. The secondary coil of the transformer is connected to the disposable via electrical contacts and the heated metal part is located in the disposable.

In system 10, primary coil 12 of the transformer creates a magnetic field directed towards secondary coil 14 of the transformer, inducing a current in the secondary coil 14. The current in the secondary coil 14 is passed to a metal structure 20c, which has a high electrical resistance compared to the transformer secondary coil and is in thermal contact with the fluid to be heated, which can be part of a disposable set, e.g., disposable dialysis set.

Heater housing 22 can be coupled to tubing (not shown) via, e.g., luer fittings, barbed fittings, press-fitting over portion 22, press-fitting portion 22 over rigid tube sections. Heater housing 22 can connect to or be part of loose tubing (for example tubing connected to a disposable cassette) or be incorporated directly into the disposable cassette. Heating housing 22 and metal structure 20a can have a cross-sectional shape suited for their application, e.g., square or rectangular for a rigid pathway of a disposable cassette, or circular for a tubing connection. Suitable materials for heater housing 22 include polycarbonate, polysulfone, urethane or potentially other high temperature plastics.

It is advantageous for primary and secondary coils 12 and 14 to be made of a wire that does not generate too much heat due to i2R power losses relative to that of metal structure 20a. Suitable materials for primary and secondary coils 12 and 14 include: (i) Cooner Wire (coonerwire.com) Litz wire, P/N=1650/44 SPSN, 1650 strands of 44 AWG Litz wire, each strand insulated, the bundle wound in nylon, which is believed to be well-suited for higher coil currents and (ii) New England Wire Technologies, P/N=NELD1050/44, SPSD Type 2 Litz wire, which is believed to be well-suited for lower coil currents, allowing for more turns in a given space.

In system 10 the electronics for powering primary coil 12 can be a circuit 24 such as a printed circuit, application specific integrated circuit ("ASIC") and the like. Circuit 24 shown in FIG. 1 includes a logic implementer 16, which includes processing and memory storage. Logic implementer receives inputs 18a (e.g., analog or digital inputs from sensors or other logic devices) and generates outputs 18b (e.g., analog or digital outputs to a heater power supply or other instrument device). Circuit 24 in the illustrated embodiment includes a power source 26 and zero-crossing switching electronics operating a transistor such as an insulated gate bipolar transistor ("IGBT") type switching device 28, or a metal oxide field effect transistor ("MOSFET"). The switch device 28 in one embodiment is an IGBT 60 amp, 1 kV device, which has zero voltage across the associated transistor or zero current through the transistor when transitioned between the on and off state to reduce the power losses in the transistor switching element 28 as it transitions from its on to off state or off to on state.

Switching device 28 in turn controls a quasi-resonant LC circuit 30, which energizes the primary coil 12 of system 10. Primary coil 12 can range from about 0.5 to about 50 uH in inductance. Coil 12 can be energized to ten amperes or more to deliver maximum power depending on power losses in the wire. LC Circuit 30 can have a resonant frequency of about 20 to 1000 kHz. The power requirement from source 26 is for example from about 300 W to about 1000 W for maximum power delivery into the fluid depending on inlet fluid temperature, outlet fluid temperature, and flow rate. A bridge rectifier (not illustrated) can also be connected between power source 26 and quasi-resonant LC circuit 30.

Typical operating frequencies for system 10 and the systems described herein are about twenty kHz to about one MHz, which are generally considered high frequencies. Audible noise limits the low frequency end of the frequency range, emitted by the electronics, primary coil 12 and secondary coil 14. Power losses in the switching circuit used to drive the inductive coil limit the high end of the frequency range. Faster electronic components will likely increase the above specified high end in the future.

In the illustrated embodiment, circuit 24, primary coil 12 and secondary coil 14 are part of the instrument and are not disposable. Heated fluid contacting metal structure 20a and housing 22 are part of a disposable set. Accordingly, the patient or caregiver needs to load metal structure 20a/housing 22 onto secondary coil 14 for operation. In the illustrated embodiment, metal structure 20a includes (integrally formed or connected) conductive legs or extensions 21 and 21 that are spaced apart and configured, e.g., hollowed, to accept secondary coil leads 14a and 14b, respectively. Conductive legs or extensions 21 can be formed with inner diameters that seal about the outside diameter of coil leads 14a and 14b. The inner diameters form blind bores that prevent coil leads 14a and 14b from actually touching the sterile medical fluid contacting structure 20a. However, conductive legs or extensions 21 enable coil leads 14a and 14b to make electrical contact with metal structure 20a. Insulating housing 22 seals about legs or extensions 21 to prevent dialysis fluid from leaking between legs 21 and housing 22.

To capture the magnetic flux and direct it towards secondary coil 14, system 10 provides a magnetic core (here inner solid cylinder 34a and outer hollow cylinder 34b) that surrounds the windings of primary coil 12 and secondary coil 14. System 10 shows that coils 12 and 14 each include a single winding, with primary coil 12 wound around the inner portion 34a of the core and secondary coil 14 wound around primary coil 12. It should be appreciated that this pattern can be repeated, that is, a second primary coil winding around first secondary coil winding, and so on, adding as many primary/secondary coil layers as desired or reversing the order of primary and secondary coils. The outer portion 34b of the core is fitted around the outermost secondary coil layer.

In FIG. 1, the disposable metal structure 20a is a cylindrical sintered metal, e.g., stainless steel, structure, which can be solid if ease of manufacture and cost so dictates. Current induced to secondary coil 14 and traveling to structure 20a via primary coil 12 tends to flow around the surface of the generally cylindrical structure 20a due to what is known in the art as a skin effect. To optimize the energy for a given amount of metal, a solid cylindrical sintered metal tube is formed or hollowed into the cylinder 20a made from porous metal or sintered metal spheres. An insulating member 32 can be filled into the opening formed by hollow cylinder 20a. Or, the sintered cylinder 20a can be formed, e.g., compressed together, around insulating member 32. Either way, the resulting structure forces fluid flowing through heating portion 22 towards the outer wall structure where most of the current resides.

System 10 can instead be converted to an inductive system by instead winding primary coil 12 around the insulating housing 22 of the disposable set, eliminating secondary coil 14 and associated contacts, and allowing metal structure 20a to operate as the secondary coil or susceptor of the inductive heating system. Circuit 24 would operate as described above in the converted inductive system. It is likewise suitable for powering the inductive systems described below.

Inductive Systems Generally

With induction heating, the heating system passes an electric current through the metal susceptor in thermal contact with the fluid. To do so, the heating system in one embodiment places the metal susceptor in magnetic contact with the primary of the transformer which drives power into the secondary coil of the transformer, known as the susceptor. This configuration electrically isolates the metal susceptor structure within the disposable from the primary coil of the transformer. The heating system uses the metal structure within the disposable as the secondary coil of the electric transformer. The system directs the changing magnetic field of the primary coil of the transformer towards the metal structure in the disposable the changing magnetic field then induces a changing electric field in the metal structure, which in turn induces an electric current to flow through the conductive metal structure. The transformer primary coil can be coupled thermally to the heating area of the disposable set to direct heat due to power losses created in the transformer primary coil through the exterior of the disposable to improve efficiency.

The inductive heating systems can operate at high frequencies. High frequency currents used to induce the magnetic field into the susceptor have the ability to create electromagnetic interference outside the heater subsystem. The medical industry places strict limits on the amount of radiation that the medical instrument as a whole can emit. The present heating systems are configured to contain the amount of radiation emitted in one or a combination of the following ways: (i) configuring the susceptor to completely (or almost completely) absorb the magnetic fields from the coil; (ii) using a ferrite or other magnetic material to direct the magnetic field to the susceptor; and (iii) providing shielding to limit the emitted electromagnetic fields.

The systems described herein can accordingly surround the heating subsystem as much as possible with lightweight, inexpensive aluminum sheeting to contain the magnetic fields. The thickness of the sheeting needs to be sufficient such that the magnetic field created by the coil of the inductive heater cannot escape the sheeting. Other potentially suitable shielding materials include lossy ferrite material and magnetic steel.

FIG. 2 illustrates an alternative metal structure 20b, or a susceptor for an inductive system, including a metal, e.g., stainless steel, tube which has been bent and then fitted inside of an insulating tube 22. Bent tube 20b stretches insulating tube 22 causing tube 22 to conform to the shape of bent tube 20b. FIG. 3 illustrates a further alternative metal structure 20c or susceptor, wherein the conductive tube is bent along its longitudinal axis and fitted inside insulating tube 22, causing tube 22 to conform to the shape of bent tube 20c. Insulating tube 22 is further alternatively vacuum sealed to the metal tube or surface or vice versa. In yet another alternative embodiment, insulating tube 22 is heat shrunk around a metal structure.

Referring now to FIG. 4, system 40 illustrates an alternative inductive heater in which a secondary coil 44 of the transformer is placed in an insulating, e.g., plastic, housing 46 made of any of the materials discussed above for heating portion 22 of system 10. Plastic housing 46 is also incorporated into the disposable set, e.g., as part of a disposable cassette for a dialysis application. A primary coil 42 shown here as a pancake coil is placed above and/or below housing 46. Primary coil 42 in an embodiment can be connected to the same circuitry shown above with system 10 of FIG. 1.

Housing 46 includes a dialysis fluid (e.g., dialysate or dialysate component) inlet 48a and a dialysis fluid outlet 48b. Housing 46 further includes baffles 38a to 38d (referred to herein collectively as baffles 38 or individually, generally as baffle 38), which direct the dialysis fluid over secondary coil 44, which winds back and forth through baffles 38. Coil 44 in one embodiment is dense enough such that baffles 38 are not needed. Secondary coil 44 is alternatively a pancake coil like coil 42, which also serves a baffling function such that separate baffles 38 are not needed.

Secondary coil 44 can be made of an induction compatible metal, such as copper coated with a medical grade compatible material, such as stainless steel, e.g., stainless steel type 316. Secondary coil 44 is alternatively a stainless steel tube bent into a coil form and filled with an induction compatible metal, such as copper rod, copper particles or copper shavings. Secondary coil 44 is alternatively pure stainless steel.

Referring now to FIG. 5, system 50 illustrates a further alternative inductive heating embodiment. Here, secondary coil 54, for example, a pancake coil, made of an induction compatible material, e.g., copper, is incorporated into one or more walls, e.g., a bottom wall 52 of housing 56. Housing 56 can include baffles 38 as described above, e.g., made of stainless steel, or be filled with stainless steel mesh or other metal filler. A primary coil (e.g., pancake coil 42 of system 40), placed below wall 52, induces a current in secondary coil which becomes heated and in turn heats the baffles or filler and the fluid within housing 56. Housing 56 further includes an inlet 58a for receiving non-heated dialysis fluid and an outlet 58b for dispelling heated fluid.

Figure 6:
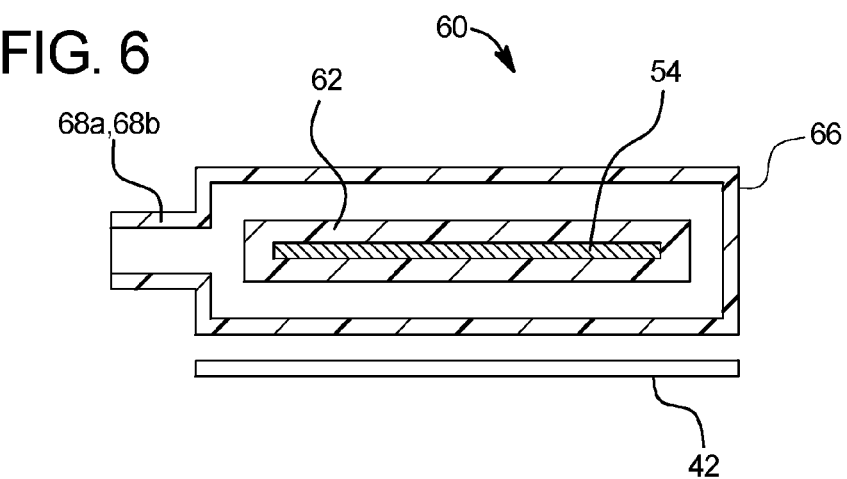
FIG. 6 is a sectioned elevation view illustrating another embodiment for an inductive dialysis fluid heating system of the present disclosure using at least one embedded secondary coil inside an insulating housing, which can be provided for the purpose of preserving the coil during storage.

Referring now to FIG. 6, system 60 illustrates yet another alternative inductive heating embodiment. Here, a primary coil, such as pancake coil 42, induces a current into one or more secondary coils 54, for example, a pancake coil, made of an induction compatible material, e.g., copper. One or more coil 54 is incorporated into one or more insulating sleeve 62 which is injection or insert molded. One or more sleeve 62 is in turn placed within housing 66. The one or sleeve 62 can additionally serve a baffling function, directing dialysis fluid from inlet 68a to outlet 68b. Housing 66 can additionally be filled with a stainless steel mesh or other medically compatible metal filler.

In any of the embodiments described herein, the inductive heating of dialysis fluid provides a good thermal transfer of energy from the electrically conductive heated element (e.g., sintered metal 20a, tubing 20b and 20c, coil 44, metal filler in FIG. 5, metal filled plastic 62 in FIG. 6, each of which can be termed generally as a "susceptor"), to the fluid. A low thermal mass of the susceptor results in little overheating of the fluid due to latent heat stored in the susceptor when the flow starts and stops, e.g., is stagnant. In combination with a fast responding fluid temperature sensor, such as an infrared sensor described below, the quick responding susceptor 20 achieves efficient control of output fluid temperature.

The present disclosure also contemplates using the dialysis fluid itself as a susceptor or more correctly in place of susceptor 20. Generally, a physical configuration that produces a magnetic field in a conductive material will produce a current in the material. Because the dialysis fluid is conductive, it can be used in place of the susceptor, that is, heat itself. One drawback of doing this is that the relatively low conductivity of the dialysis fluid would require a relatively high voltage to the primary coil to provide adequate heating.

As shown above, one possible primary coil design is the pancake design. However, certain research indicates that the most efficient primary coil design is a coil that is wrapped around the metal structure or susceptor 20, similar to a solenoid winding, which could limit use of the "pancake" design. Thus in FIG. 1, primary coil 12a can be wound around insulator 22, wherein metal apparatus 20a is the secondary coil to provide a more efficient heater. For FIGS. 4 and 6 above, coil 42 is alternatively wound around the respective housing. In FIG. 5, coil 54 is alternatively wound helically through housing 56.

Figure 7:
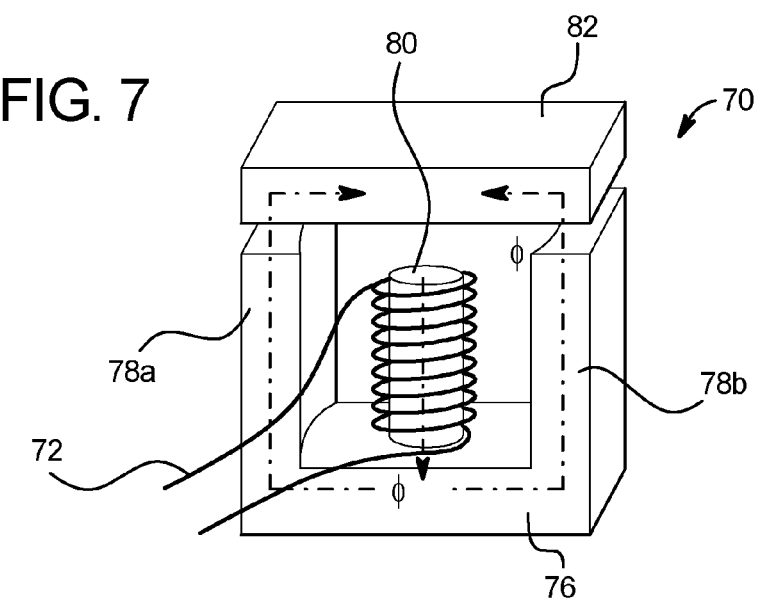
FIG. 7 is a perspective view illustrating an embodiment for an inductive dialysis fluid heating system of the present disclosure using a spirally or helically wound primary coil, a flux directing core including first and second pieces and a secondary coil tube.

Referring now to FIG. 7, system 70 illustrates a further solenoid-like coil embodiment. Here, coil 72 wraps around a metal core 76, which includes arms 78a and 78b cooperating with a second core body 82 to direct a magnetic flux $\Phi$ through to secondary coil, here a tube 80. Flux $\Phi$ travels up arms 78a and 78b and down tube 80 as shown by the arrows. Coil 72 in any of the embodiments shown herein can be powered via electronic circuit 24 shown in FIG. 1. Tube 80 can be stainless steel, e.g., a magnetically susceptible stainless steel 430. A magnetic heating tube or susceptor improves the energy efficiency of the fluid heating system. Metal core 76 and 82 in any of the embodiments herein can be of a magnetic substance, which tends to be stable even at high frequencies.

In the illustrated embodiment, dialysis fluid flows through the inside of tube 80. Tube 80 can be a single, wide tube as shown below or multiple narrow tubes as also shown below. Here, the outside of tube 80 can be coupled to a temperature sensor that measures the temperature of susceptor tube 80 to, for example, detect air or low flow in the system, enabling the system to react and prevent air from reaching the patient, to remove a line occlusion and/or to prevent overheating of tube 80.

Figure 8:
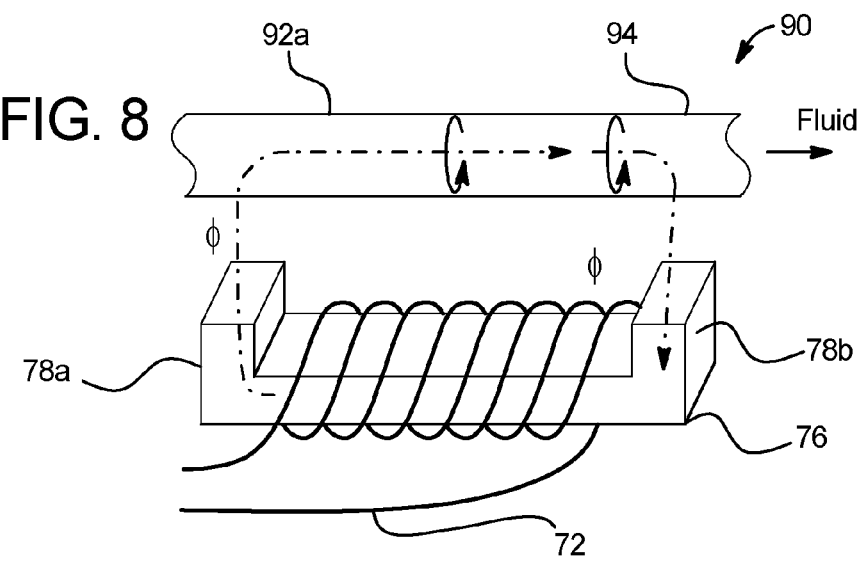
FIG. 8 is a perspective view illustrating an embodiment for an inductive dialysis fluid heating system of the present disclosure using a spirally or helically wound primary coil, a flux directing core and a secondary coil tube.

Referring now to FIG. 8, system 90 illustrates yet another solenoid-like coil embodiment. Here, coil 72 again wraps around a metal core 76, which includes arms 78a and 78b that direct a magnetic flux $\Phi$ through to secondary coil, here a tube 92a. Fluid flows through tube 92a as indicated by the associated arrow. Tube 92a can be stainless steel, e.g., magnetically susceptible stainless steel 430. A temperature sensor 94 is placed at the down stream end of tube 90, showing one preferred positioning of a temperature sensor for providing feedback to the heating system 90. Core 76 and arms 78a and 78b operate as described above.

Referring now to FIG. 9, system 100 illustrates a pancake coil embodiment. Here, pancake coil 42 directs a magnetic flux $\Phi$ perpendicular to the plane of its coil, through to secondary coils and heater plates 102 and 104. Coil 42 in any of the embodiments shown herein can be powered via electronics 24 shown in FIG. 1. Heater plates 102 and 104 can be stainless steel, e.g., magnetically susceptible stainless steel 430. Fluid can flow above and/or below plates 102 and 104 in the direction of the associated arrows, perpendicular to the arrows or diagonally to the arrows. The plates can be roughened or sintered to increase the turbulence of dialysis fluid flow here and in other flat plate embodiments discussed herein.

Referring now to FIG. 10, system 10a illustrates yet another solenoid-like coil embodiment. Here, coil 72 wraps around a metal core 76, which includes longer arm 78a and shorter arm 78b directing a magnetic flux $\Phi$ through to a plurality of secondary coils and heater plates 112, 114, 116 and 118. Heater plates 112, 114, 116 and 118 can be stainless steel, e.g., magnetically susceptible stainless steel 430. The sheets can be roughened or sintered to increase the turbulence of dialysis fluid flow. Fluid can flow meander up and down around plates 112, 114, 116 and 118 or side-to-side around plates 112, 114, 116 and 118. Arms 78a and 78b may also be the same length, either both long or both short to accommodate susceptor plates 112, 114, 116 and 118.

Referring now to FIG. 11, system 110b illustrates yet another solenoid-like or helical coil embodiment. Like system 110a of FIG. 10A, system 130 includes a plurality of heater plates 112, 114 and 116. Here, coil 72 wraps around a plurality of heater plates 112, 114, and 116, etc. Heater plates 112, 114 and 116 can be stainless steel, e.g., magnetically susceptible stainless steel 430. Fluid flow can meander up and down around plates 112, 114 and 116 or side-to-side around plates 112, 114 and 116. Plates 112, 114 and 116 can be separate sheets of metal or formed from a single sheet. The sheets can be roughened or sintered to increase the turbulence of dialysis fluid flow.

Referring now to FIG. 12, susceptor or secondary coil 120 illustrates an embodiment for a baffled susceptor. As opposed to separate baffles 38a to 38d discussed above, coil 120 is formed of a single sheet of stainless steel, e.g., magnetically susceptible stainless steel 430, which is bent multiple times to form a serpentine or baffled pathway. A plurality of insulating baffles 124a to 124d (referred to herein collectively as baffles 124 or individually as baffle 124) extend inwardly from the walls of housing 122 and between the folds of the single sheet 120. Baffles 124 partition flow of dialysis fluid around the folds of heated sheet 120. Flow of dialysis fluid can be from top to bottom, from bottom to top, into the page and out of the page with respect to the housing 120 as oriented in FIG. 12.

The primary coil operable with secondary coil 120 can be a pancake coil placed adjacent to any one or more sides of housing 122. Alternatively, the primary coil is spirally or helically wound around housing 122 and susceptor 120 in the solenoid fashion shown above. Any metal core 76 or body 82 and associated arms shown herein can be magnetic. In each of the above-described systems, coil 72, core 76, body 82 are each part of the dialysis instrument, while the secondary coil or susceptor is part of a sterile dialysis fluid disposable.

Figure 13A:
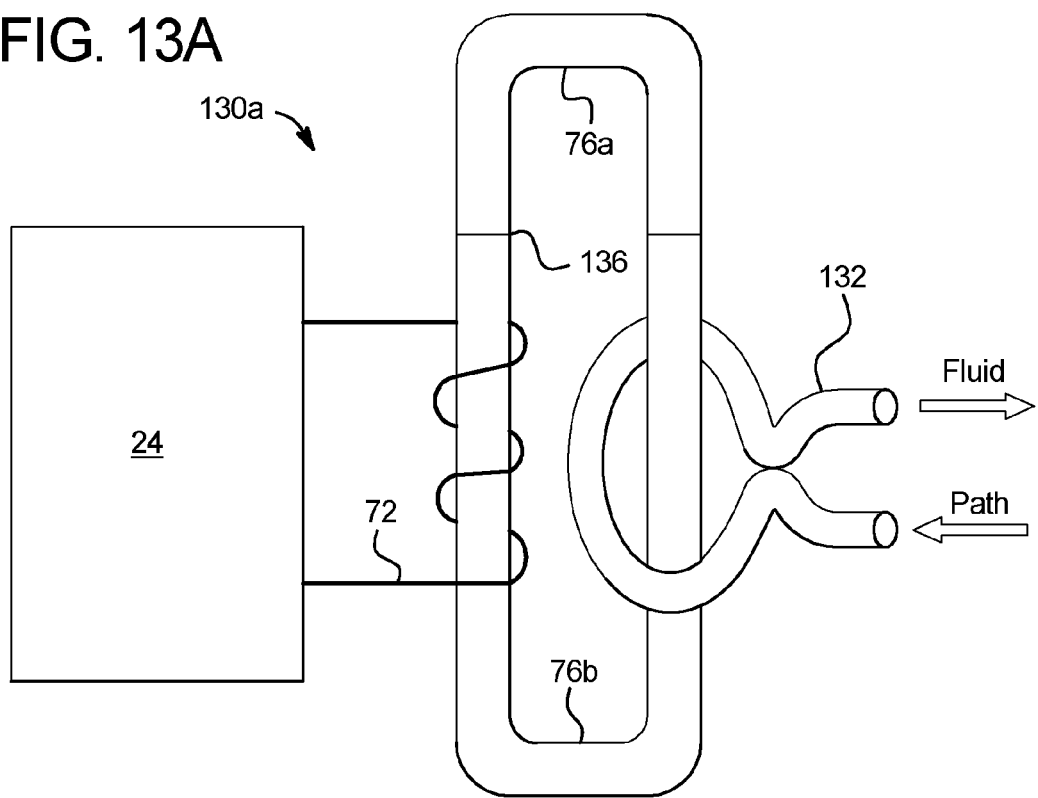
FIG. 13A is a schematic view illustrating one embodiment for an inductive dialysis fluid heating system of the present disclosure using a split magnetic core.
Figure 13B:
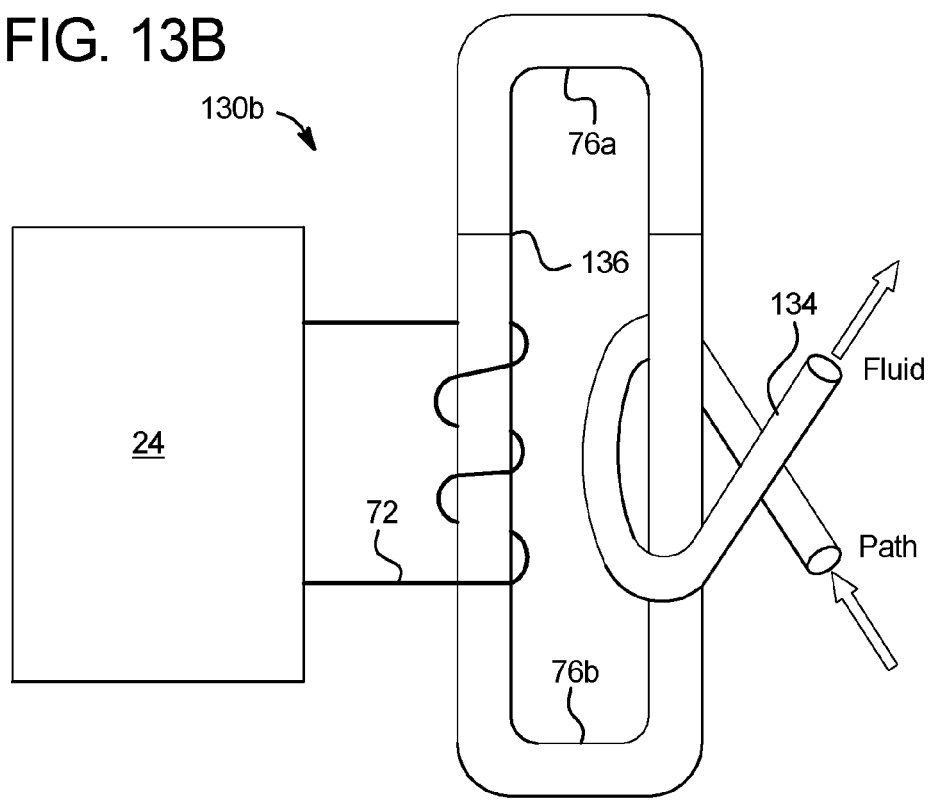
FIG. 13B is a schematic view illustrating another embodiment for an inductive dialysis fluid heating system of the present disclosure using a split magnetic core.

Referring now to FIGS. 13A and 13B, systems 130a and 130b illustrate inductive heating systems that employ a split magnetic core 76a/76b, facilitating the insertion and removal of disposable heating tubes 132 (FIG. 13A) and 134 (FIG. 13B), respectively. Primary coil 72 connects to induction circuit 24 described above and wraps around magnetic core 76a/76b, which can be a magnetically susceptible material stainless steel 430. Tubes 132 and 134 are stainless steel, e.g., magnetically susceptible stainless steel 430 is one embodiment.

Core 76a/76b directs the magnetic flux to heating tubes or susceptors 132 and 134. Susceptors 132 and 134 in the illustrated embodiment are single loops of metal tube. When passed through a magnetic core 76a/76b, the core directs the magnetic field through the center of the loop of core 76a/76b.

A disposable for systems 130a and 130b includes the conductive metal tubes 132 and 134 with fluid inlet and outlet of the tubes making electrical contact with each other. Coil 72 and core 76a/76b are positioned so that tubes 132 and 134 of the disposable may be loaded and removed easily from the magnetic core. In system 130b, the shape of tubing 134 is simpler, so that a single continuous bend is created with the ends of the tube overlapping.

While metal tubes 132 and 134 are shown on the opposite side of core 76 from primary coil 72, tubes 132 and 134 can alternatively be moved closer to primary coil 72 and still be loaded into their respective systems 130a and 130b. For example, core portion 76b can be located along with primary coil 72 within the main body of the system instrument, while core portion 76a is provided in the door of the system instrument. Either metal tube 132 and 134 can then be loaded (for example with a disposable cassette) into the instrument such that it loops about seam 136 when the door is closed and core portions 76a and 76b are mated to form core portion 76. Such loading of the cassette and susceptor places either metal tube 132 and 134 closer to coil 72, increasing heater efficiency.

Baffled Heating Modules

Referring now to FIGS. 14A to 14E, heating module 150 illustrates one possible secondary coil and housing embodiment. The housing of heating module 150 includes a base 152 and a lid 162. Base 152 and lid 162 are made of a suitable medical grade plastic, such as polycarbonate, polysulfone, polyurethane or potentially other high temperature plastics. Base 152 includes longer side walls 154a and 154b, shorter end walls 156a and 156b and a bottom 158. At end wall 156a, base 152 includes or defines a dialysis fluid inlet 160a and a dialysis fluid outlet 160b.

Dialysis fluid inlet 160a and dialysis fluid outlet 160b can be a suitable medical tube port connector, such as a luer connector or a hose barb connector. Dialysis fluid inlet 160a and dialysis fluid outlet 160b can connect heating module 150 directly to a disposable pumping and/or cassette for example. Dialysis fluid inlet 160a and dialysis fluid outlet 160b alternatively connect heating module 150 to another part of a disposable dialysis set, such as one for peritoneal dialysis or hemodialysis, such as inline with a supply or patient line. It should be appreciated that any of the fluid heating embodiments described herein can be used to heat already mixed dialysate or a fluid component or concentrate used in making dialysate.

Lid 162 includes longer side walls 164a and 164b, shorter end walls 166a and 166b and a top 168. At end wall 166a, lid 162 includes or defines inlet and outlet covers 170a and 170b, respectively.

Figure 14A:
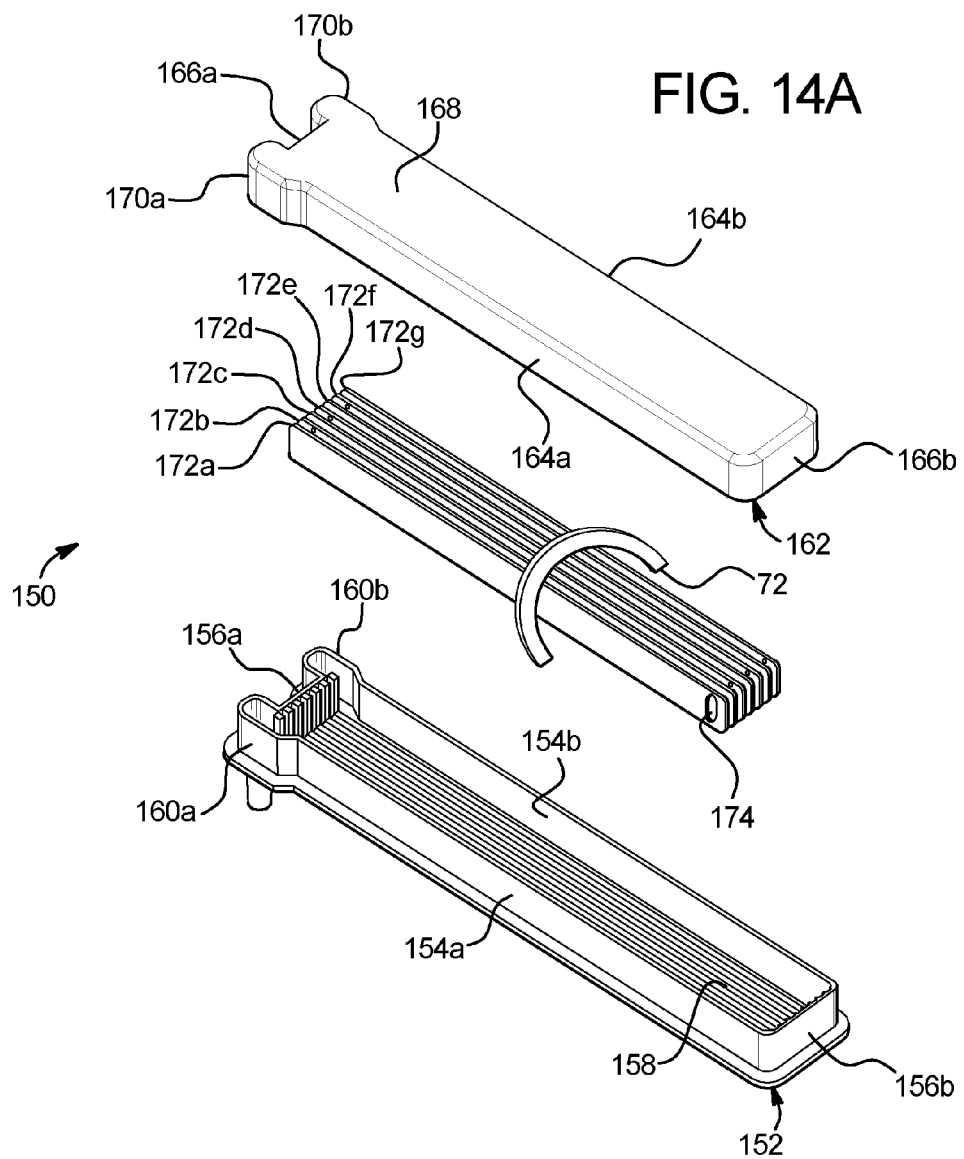
FIG. 14A is an exploded perspective view of various parts of a secondary coil fluid heating module of the present disclosure using multiple separate baffle plates.
Figure 14B:
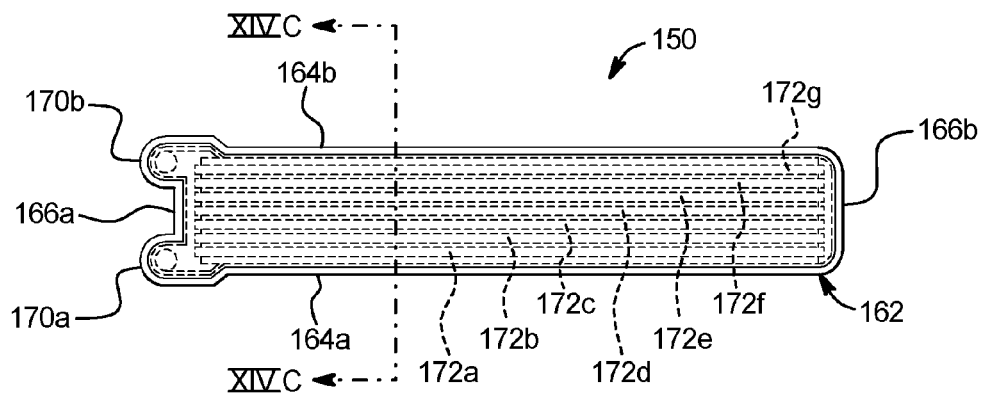
FIG. 14B is a top plan view of the heating module of FIG. 14A.
Figure 14C:
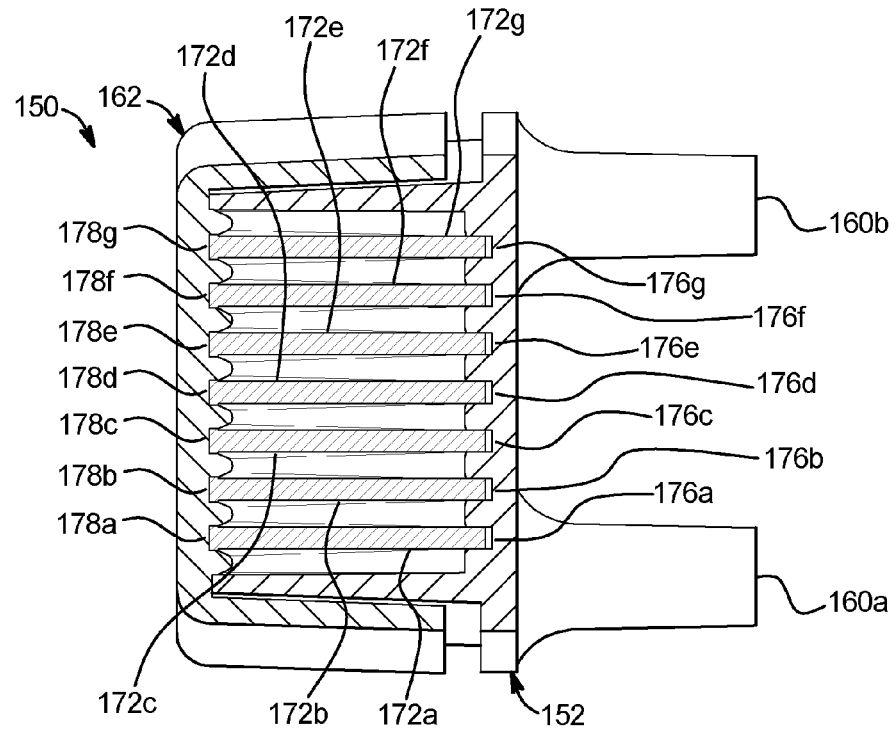
FIG. 14C is an end-sectioned view of the heating module taken along line XIV C-XIV C of FIG. 14B.
Figure 14D:
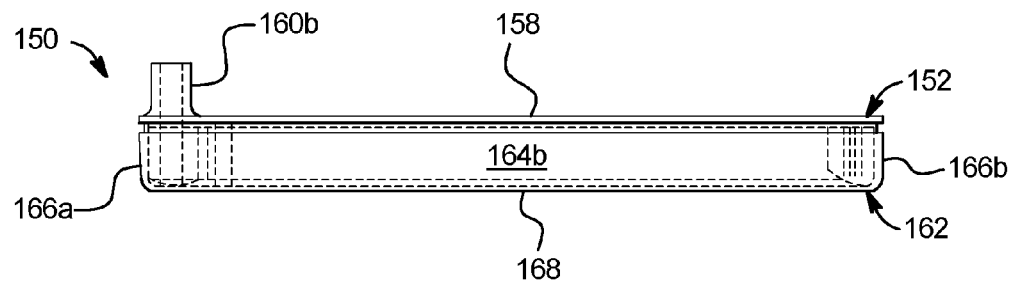
FIG. 14D is a side elevation view of the heating module of FIG. 14A as assembled.
Figure 14E:
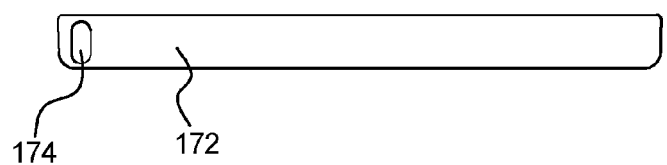
FIG. 14E is a side elevation view of one embodiment of a baffle plate of the module of FIG. 14A.

FIGS. 14A to 14C illustrate that in one embodiment, heating module 150 employs seven conductive baffle plates 172a to 172g (referred to herein collectively as heater baffle plates 172 and individually, generally as baffle or plate 172) as its secondary coil. Baffle plates 172 can be stainless steel, e.g., magnetically susceptible stainless steel 430. Baffles 172 can be roughened or sintered to increase the turbulence of dialysis fluid flow.

As seen in FIGS. 14B and 14C, dialysis fluid flow meanders back and forth along the length of plates 172a to 172g. Plates 172a to 172g in the illustrated embodiment each define a corresponding aperture 174 (FIG. 14E), which alternates from being located at either end 156a or 156b of base 152 in adjacent plates to force fluid to flow back and forth along alternating plates from one end to another. This allows plates or baffles 172 to all be made the same and to then just be fitted in an alternating arrangement for assembly. It also allows each plate 172 to be held fixed at each of its ends in a manner similar to that shone in FIG. 14C, in which the bottoms of plates 172 fit frictionally into grooves 176a to 176g defined by bottom 158 of base 152, and in which the tops of the plates 172 fit frictionally into grooves 178a to 178g defined by top 168 of lid 162. The ends of plates 172 likewise fit frictionally into grooves (not illustrated) defined by the ends 156a and 156b of base 152.

In the illustrated embodiment, the height of module 150 from bottom 158 to top 168 (seen best in FIG. 14D) is about 0.47 inch (11.9 mm). The height of module 150 from the tip of inlet/outlet 160a/160b to top 168 (seen best in FIG. 14D) is about 0.80 inch (20.3 mm). In the illustrated embodiment, the width of module 150 from side 164a to side 164b (seen best in FIG. 14B) is about 0.84 inch (21.3 mm). The width of module 150 from outlet cover 170a to outlet cover 170b (seen best in FIG. 14B) is about 0.99 inch (25.1 mm). Plates 172 can have dimensions of about 3.25 inch (8.26 cm) long and 0.38 inch (9.7 mm) high (as seen best in FIG. 14E and are spaced apart by approximately the thickness of the baffles 172, which can be about 0.036 inch (9.1 mm).

A bond may not be needed to hold plates 172 in a sturdy manner using the grooves discussed above although a medically safe, high temperature adhesive bond could be used. Also, in one embodiment, lid 162 snap-fits to base 152 such that fluid does not leak from heating module 150. A gasket or soft, compliant material can be compressed between lid 162 to base 152 to help provide a fluid-tight seal. Again, a medically safe, adhesive bond or ultrasonic weld could be used to seal lid 162 to base 152.

In one embodiment, the fluid heating system using heating module 150 winds a primary transformer coil 72 in a spiral or helical, e.g., solenoid-like manner about assembled base 152 and lid 162. The helical coil 72 can spiral along any desired part and percentage of assembled base 152 and lid 162, leaving inlet 160a and outlet 160b exposed for connection to the disposable cassette or set. The primary coil is powered via the electronics 24 shown in FIG. 1 for example.

A fluid heating module very similar to heating module 150 was tested using the electronic circuit from a hot plate manufactured by Sunpentown, P/N: SR-1881 as a power supply. The primary coil 72 used was wound seventeen turns in a helical manner around the housing of the heating module, such that the axis of the helical coil was at least substantially parallel to the length of blades 172 shown in FIG. 14A. Coil 72 was a small gauge wire, approximately 22 AWG. With water passing through the disposable at a rate of about 335 ml/min, the heating module heated the water from about 22.3° C. to about 56.2° C., which indicated a power input of the heating module into the water of about 789 Watts. The power into the hot plate primary from the AC mains was measured at 888 Watts. This indicated an overall efficiency of about 89%.

Heating module 150 is efficient from a magnetic and thermal standpoint. Metal susceptor blades 172 can be made relatively inexpensively and part count is minimal. Thinning the blades and lowering the induction frequencies increases the effects of current cancellation, making heating module 150 less efficient. Thinner blades 172, on the other hand, can make heating module 150 more responsive and less prone to overheating the dialysis fluid. These factors each play into the final dimensions chosen for heating module 150.

The number of metal blades 172 can be reduced and the same amount of power into the fluid can be achieved (same fluid heat rise and flowrate) by operating the plates at a higher temperature. For example, using two of the same metal plates 172 operating at 75° C. as opposed to the seven shown above for heating module 150, which are heated to 55° C., achieves the same fluid outlet temperature for the same fluid flowrate.

Referring now to FIGS. 15A to 15E, an alternative heating module 180 is illustrated. Heating module 180 is very similar to heating module 150 above and includes many like element numbers as heating module 150, incorporating all the disclosure and alternatives concerning those numbers by reference. In the illustrated embodiment, heating module 180 has six plates 172a to 172f as opposed to the seven shown in FIGS. 14A to 14E. Plates 172a to 172f are held mechanically via grooves 176a to 176f and 178a to 178f as described above and via a suitable adhesive bond if necessary. Fluid travels alternatively between plates via apertures 174 as described above.

The primary difference between heating module 180 and heating module 150 is that base 182 and lid 184 are modified from above to provide inlet 160a and outlet 160b and inlet and outlet covers 170a and 170b, respectively, along the same longer side 154b of base 182. An initial flow path 157 is added at end 156b of base 182 to enable the baffled flow to begin at side 154a of base 182 and end at side 154b of base 182.

Figure 15A:
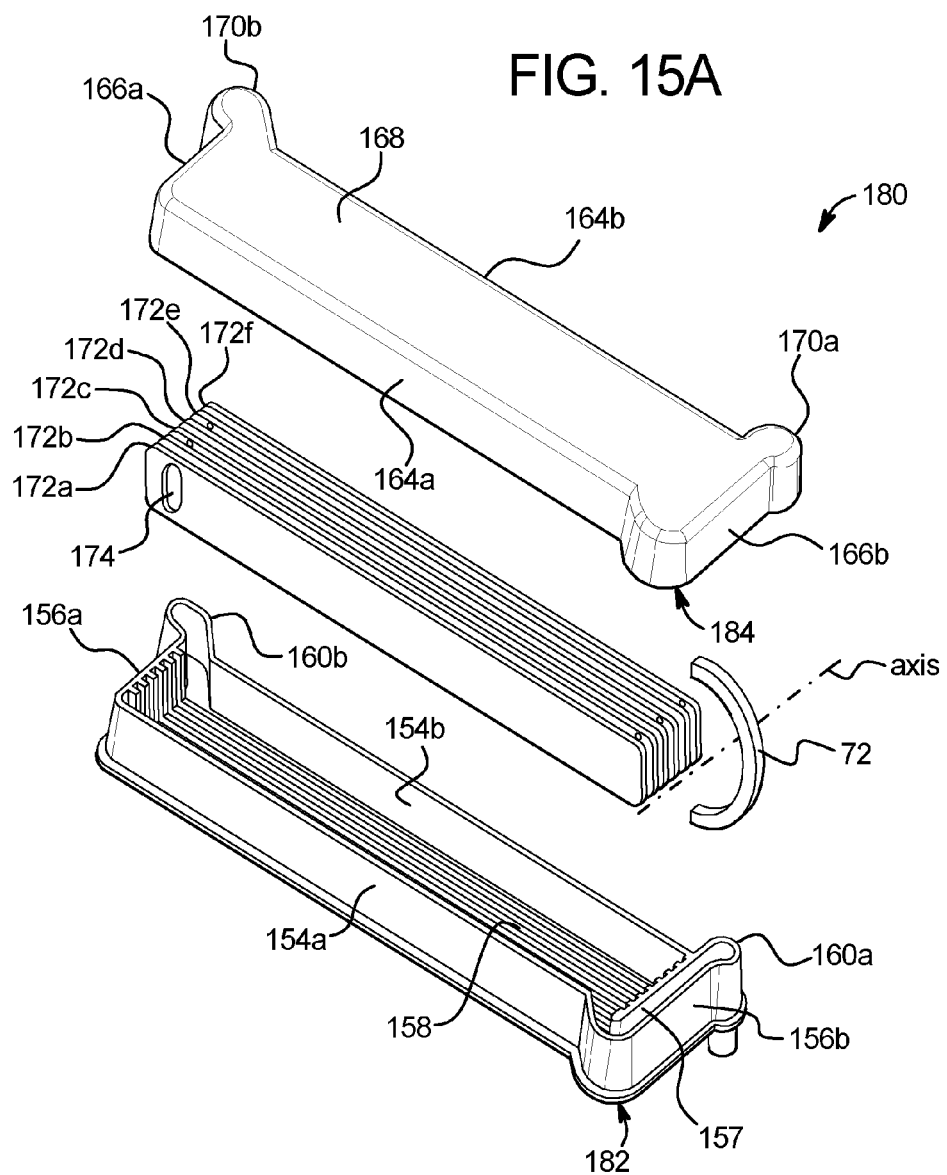
FIG. 15A is an exploded perspective view of various parts of another secondary coil fluid heating module of the present disclosure using multiple separate baffle plates.
Figure 15B:
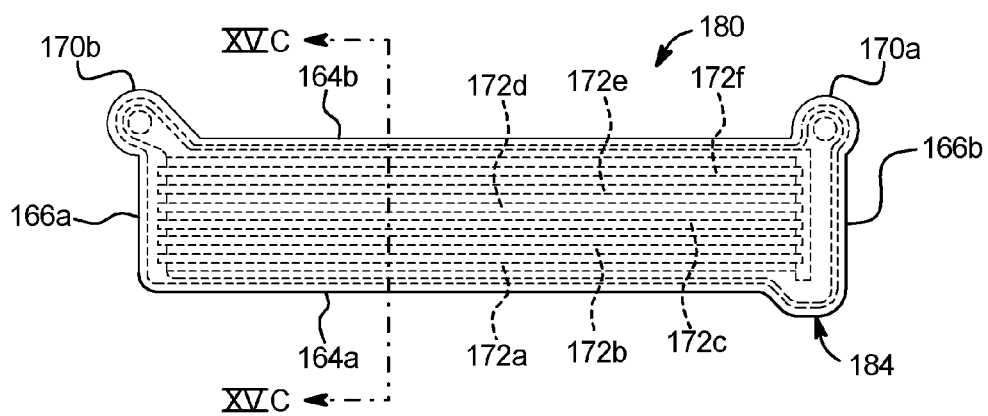
FIG. 15B is a top plan view of the heating module of FIG. 15A.
Figure 15C:
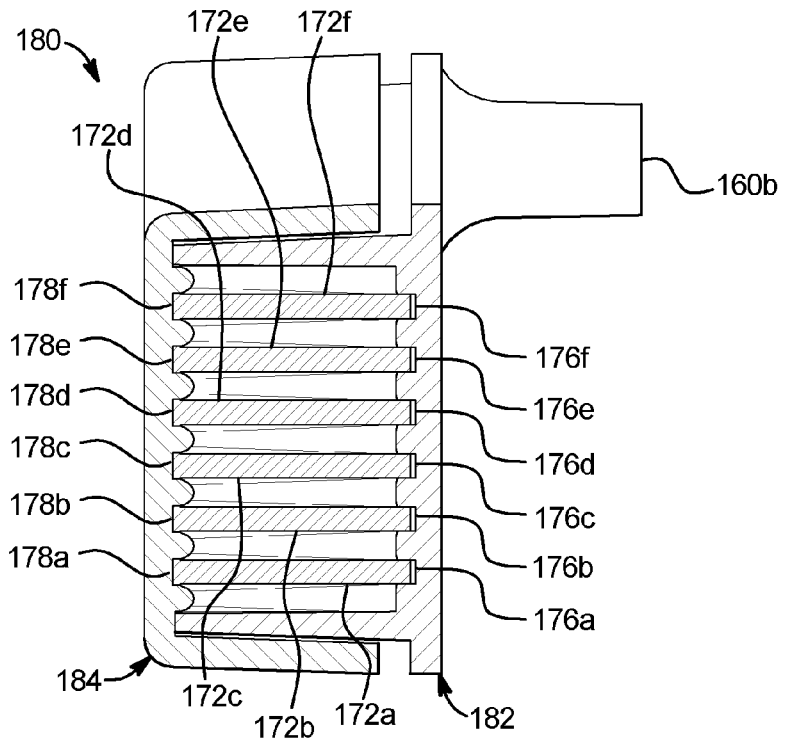
FIG. 15C is an end-sectioned view of the heating module taken along line XV C-XV C of FIG. 15B.
Figure 15D:
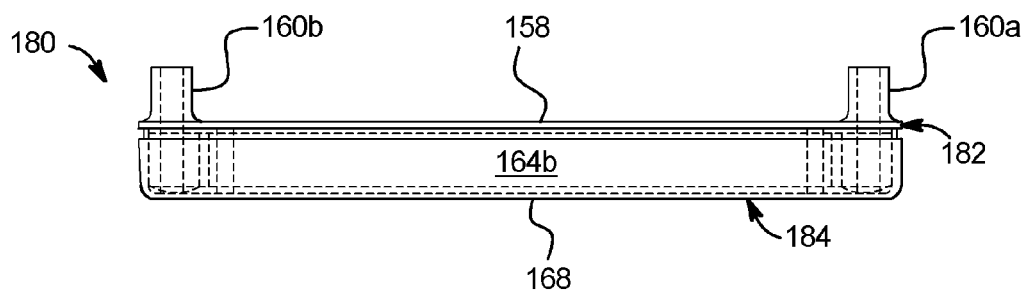
FIG. 15D is a side elevation view of the heating module of FIG. 15A as assembled.
Figure 15E:
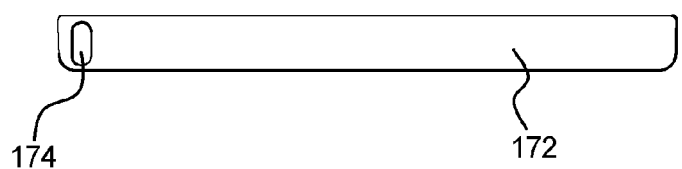
FIG. 15E is a side elevation view of one embodiment of a baffle plate of the module of FIG. 15A.

Placing both inlet 160a and outlet 160b at same longer side 154b of base 182 facilitates the winding of the primary coil 72 lengthwise as seen in FIG. 15A, so that the primary windings run at least substantially parallel to the longer length of plates 172. That is, the axis of the coil as seen in FIG. 15A is at least substantially perpendicular to the faces of plates 172. Heating module 180 is substantially the same as heating module 150 from a heat transfer viewpoint but different from a magnetic coupling viewpoint. Here, the current in the blades runs along the edge of the blade, therefore there is no current cancellation for any realistic frequencies. A disadvantage to this concept is poor coil efficiency due to the short coil length (see FIG. 15A, length produced by stack of turns) compared to the cross-sectional area formed within one turn of the coil.

Coil 72 could also be wound lengthwise and be rotated ninety degrees, such that its axis is at least substantially perpendicular to top 168 of lid 184 and bottom 158 of base 182. This configuration would likely also yield poor coil efficiency due to the resulting short coil (small number of turns) and current cancellation at low frequencies.

In the illustrated embodiment, the height of module 180 from bottom 158 to top 168 (seen best in FIG. 15D) is about 0.47 inch (11.9 mm). The height of module 180 from the tip of inlet/outlet 160a/160b to top 168 (seen best in FIG. 15D) is about 0.80 inch (20.3 mm). The largest width of module 180 (seen best in FIG. 15B) is about 1.11 inch (2.82 cm). Plates 172 can have dimensions of about 3.25 inch (8.26 cm) long and about 0.38 inch (9.7 mm) high (as seen best in FIG. 15E) and are spaced apart by approximately the thickness of the baffles 172, which can be about 0.036 inch (9.1 mm) as seen best in FIG. 15C.

Referring now to FIGS. 16A to 16E, an alternative heating module 210 is illustrated. Heating module 210 is very similar to heating modules 150 and 180 above and includes many like element numbers as heating modules 150 and 180, incorporating all the disclosure and alternatives concerning those numbers by reference. The primary difference between heating module 210 and heating modules 150 and 180 is that alternative base 186 and lid 188 are modified from above to provide for only two baffle plates 172a and 172b. As discussed above, the number of baffles can be reduced and the same amount of power into the fluid can be achieved (same fluid heat rise and flowrate) by operating the plates 172 at a higher temperature.

Plates 172a and 172b are held mechanically via grooves 176a, 176b and 178a, 178b as described above and via a suitable adhesive bond if necessary. Fluid travels between plates via apertures 174 as described above.

Figure 16A:
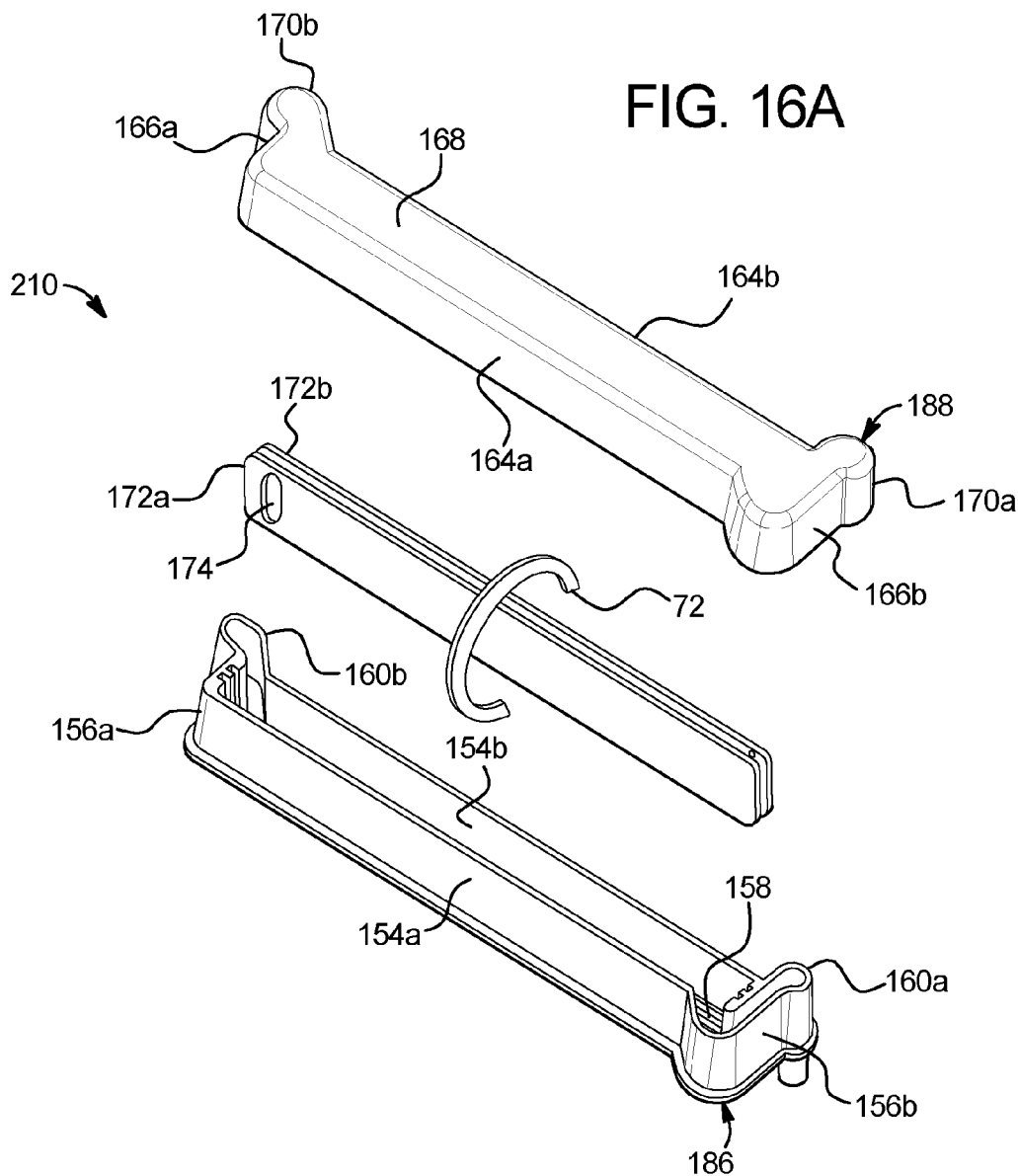
FIG. 16A is an exploded perspective view of various parts of a further secondary coil fluid heating module of the present disclosure using multiple separate baffle plates.
Figure 16B:
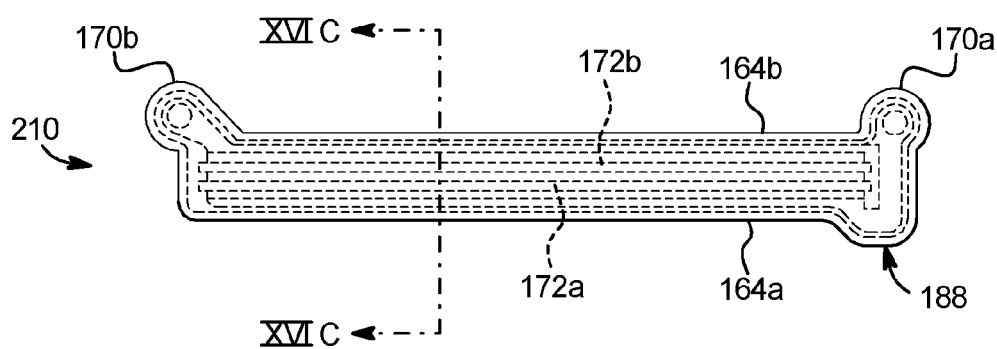
FIG. 16B is a top plan view of the heating module of FIG. 16A.
Figure 16C:
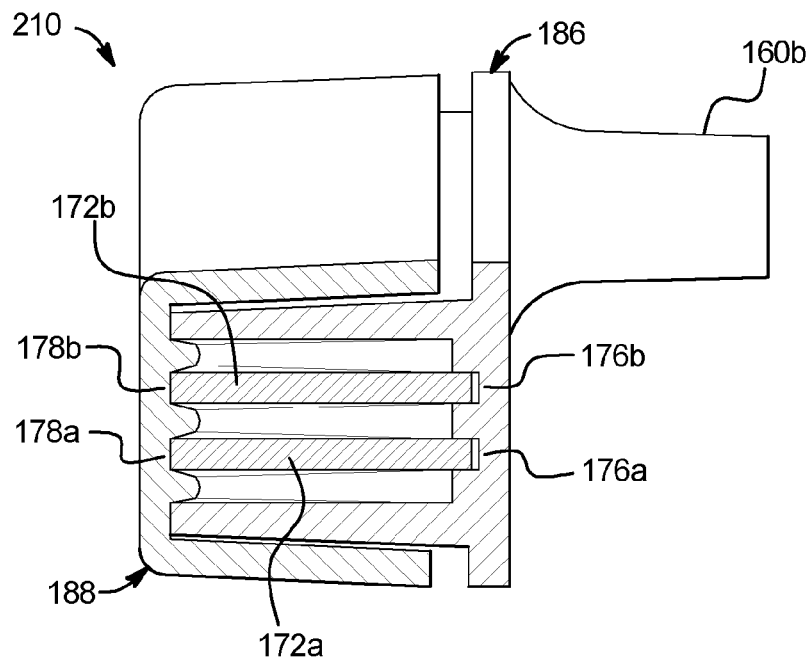
FIG. 16C is an end-sectioned view of the heating module of FIG. 16A taken along line XVI C-XVI C of FIG. 16B.
Figure 16D:
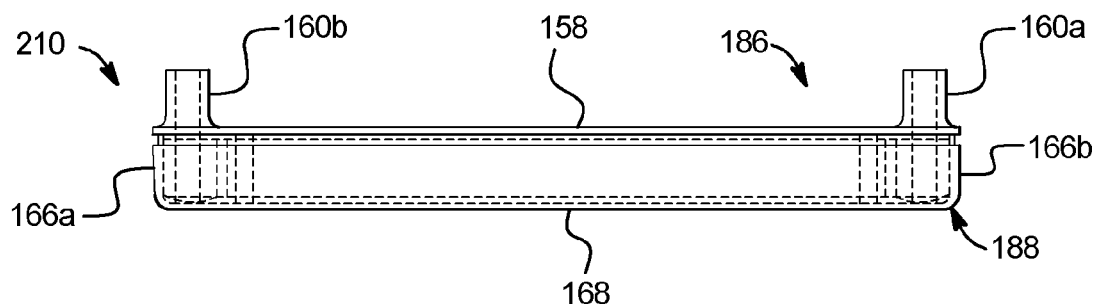
FIG. 16D is a side elevation view of the heating module of FIG. 16A as assembled.
Figure 16E:
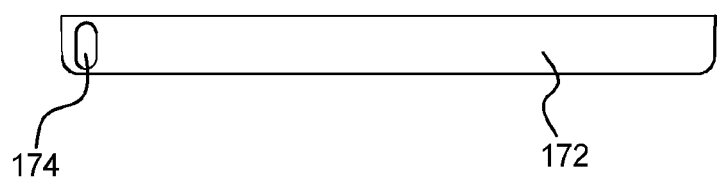
FIG. 16E is a side elevation view of one embodiment of a baffle plate of the module of FIG. 16A.

In the illustrated embodiment, the height of module 210 from bottom 158 to top 168 (seen best in FIG. 16D) is about 0.47 inch (11.9 mm). The height of module 210 from the tip of inlet/outlet 160a/160b to top 168 (seen best in FIG. 16D) is about 0.80 inch (20.3 mm). The longest length of module (as best seen in FIGS. 16B and 16D is about 3.87 inches (9.83 cm). The largest width of module 210 (seen best in FIG. 16B) is about 1.11 inch (2.82 mm). Plates 172 can have dimensions of about 3.25 inch (8.26 cm) long and about 0.38 inch (9.7 mm) high (as seen best in FIG. 16E) and are spaced apart by approximately the thickness of the baffles 172, which can be about 0.036 inch (9.1 mm) as seen best in FIG. 16C.

Referring now to FIGS. 17A to 17F, a further alternative baffled heating module 220 is illustrated. Heating module 220 is a three plate module, which is similar to heating modules 150, 180 and 210 above and includes many like element numbers as heating modules 150, 180 and 210, incorporating all the disclosure concerning those numbers by reference.

The primary difference between heating module 220 and heating modules 150, 180 and 210 is that alternative base 212 and cap 214 are modified from above to provide for three baffle plates 172a to 172c. As discussed above, the number of baffles can be optimized with the operating temperature of the plates 172 to input a desired amount of power and frequency into the fluid.

Another difference is that inlet 216 and outlet 218 are placed next to each other on generally cylindrical cap 214. Dialysis fluid inlet 216 and dialysis fluid outlet 218: (i) can be any suitable medical tube port connector, such as a luer connector or a hose barb connector; (ii) can connect heating module 220 directly to a disposable pumping cassette for example; or (iii) alternatively connect heating module 220 to another part of a disposable dialysis set, such as inline with a supply line or patient line.

FIG. 17C shows one suitable interface between cap 214 and base 212. Base 212 includes an ultrasonic weld energy director 222, which extends at an angle ⊖ from a top of base 212. Angle ⊖ in one embodiment is about forty-five degrees. Cap 214 includes a mating recess that accepts ultrasonic weld energy director 222 of base 212. In an embodiment, cap 214 and base 212 are welded together ultrasonically. Angled energy director 222 helps to focus the ultrasonic energy at that point (annular pointed ridge), so that the director 222 and mating recess bond to provide a solid seal around the entire interface between cap 214 and base 212. It should be appreciated that the interface area needed to be sealed is less for module 220 than for modules 150, 180 and 210 shown above. Cap 214 and base 212 (as can any mating plastic pieces discussed herein) can alternatively or additionally be secured mechanically and/or by adhesive bond.

Plates 172a, 172b and 172c can be sintered or roughened as described herein and are held mechanically via grooves 176a, 176b and 176c in base 212 and grooves 178a, 178b and 178c in cap 214 as described above and via a suitable adhesive bond if necessary. Grooves 176a, 176b and 176c also extend into the sides of base 212 as seen in FIG. 17F.

Fluid travels between plates via apertures 174 as described above and shown in FIG. 17F. With heating module 220, fluid flows into inlet 216, down base 212, along the outside of baffle 172a, though an aperture 174 at the bottom of baffle 172a, up base 212 between baffles 172a and 172b, though an aperture 174 at the top of baffle 172b, down base 212 between baffles 172b and 172c, though an aperture 174 at the bottom of baffle 172c, up base 212 along the outside of baffle 172c, and out outlet 218.

In the illustrated embodiment, the height of module 220 from the bottom of base 212 to the top of cap 214 is a little bigger than three inches (7.62 cm). The height of ultrasonic energy director 222 above the top of base 212 is about 0.015 inch (0.381 mm). A total width x1 from outside of inlet 216 to the outside of outlet 218 (as seen in FIG. 17D) is about 0.540 inches (1.37 cm). The width x2 between the centers of inlet 216 and outlet 218 (as seen in FIG. 17D) is about 0.300 inch (7.62 mm). Plates 172 can have dimensions of about 3.00 inch (7.62 cm) long and about 0.300 inch (7.62 mm) high (as seen in FIG. 17F), are about 0.020 inch (0.508 mm) thick, have an aperture diameter of about 0.125 inch (3.18 mm) and be spaced apart by a gap of approximately 0.050 inch (1.27 mm). Baffle 172a can be spaced apart from baffle 172c a distance x3 of about 0.160 inch (4.06 mm).

In one embodiment, as seen in connection with FIG. 17B, the fluid heating system using heating module 220 winds a primary transformer coil 72 in a spiral or helical, e.g., solenoid-like, manner about assembled base 212 and perhaps a portion of cap 214. The helical coil 72 can spiral along any desired part and percentage of assembled base 212 and cap 214, leaving inlet 216 and outlet 218 exposed for connection to the disposable cassette or set. The primary coil is powered via electronics 24 shown in FIG. 1 for example.

Figure 18A:
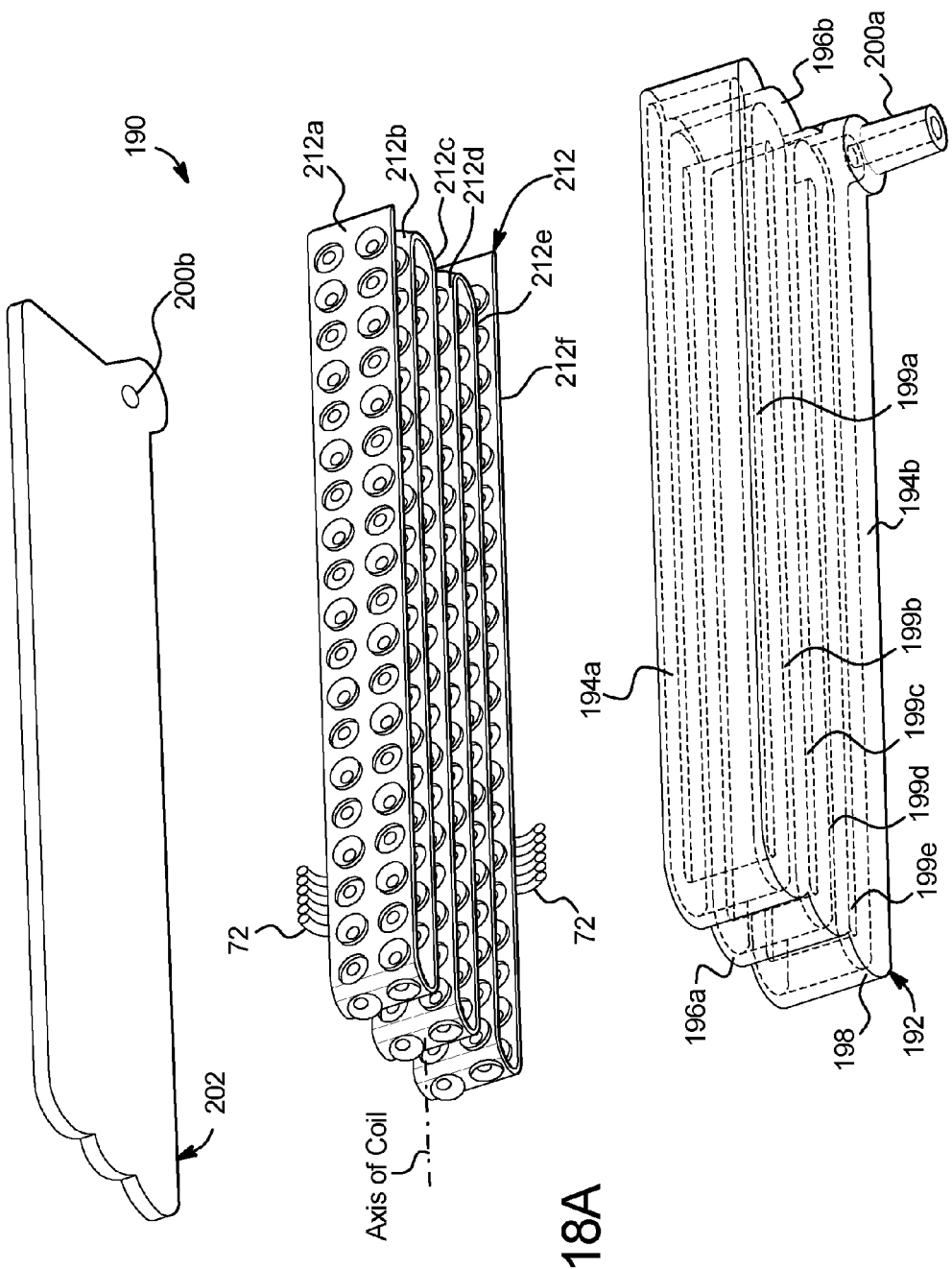
FIGS. 18A to 18C are perspective views of various parts of a secondary coil fluid heating module of the present disclosure using multiple baffle plates or folds from a single sheet of metal.
Figure 18B:
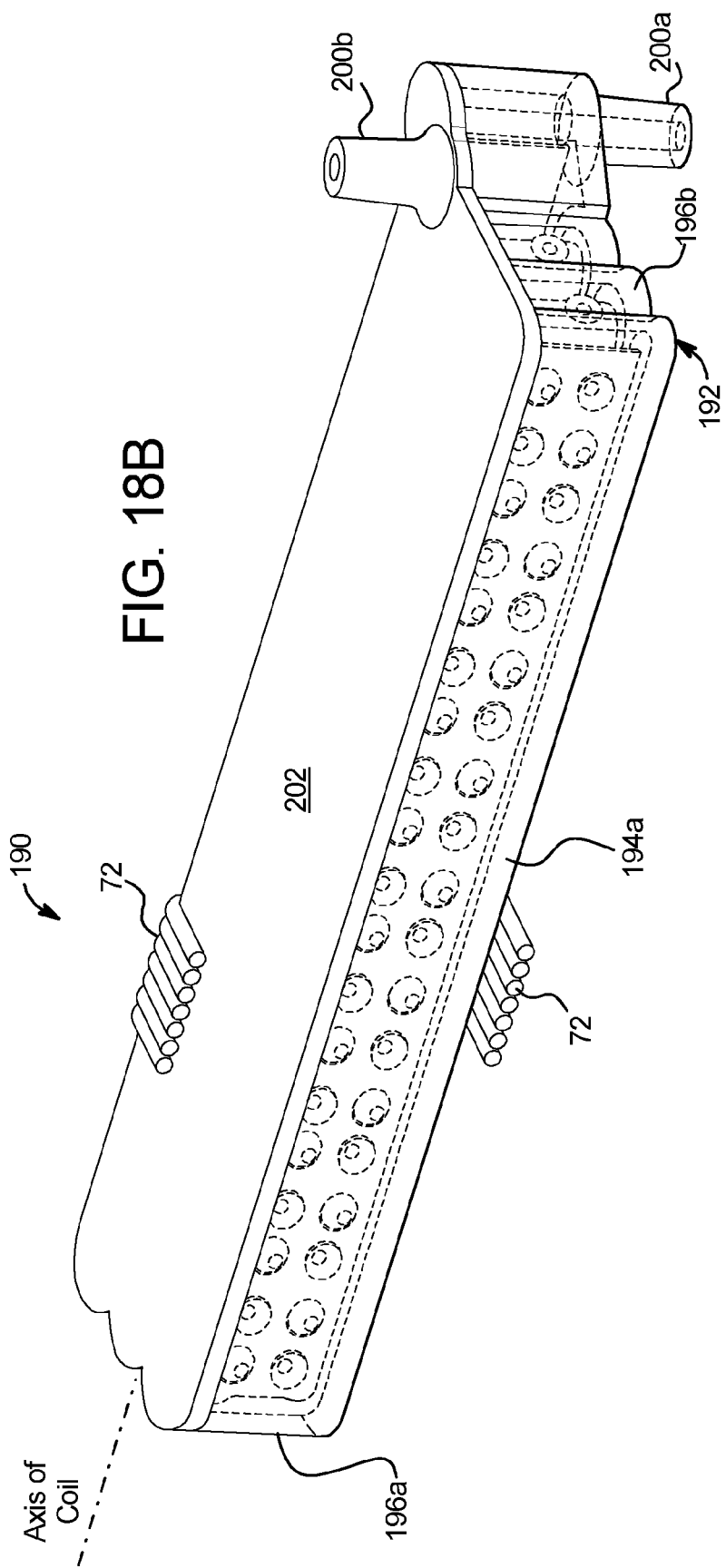
Figure 18C:
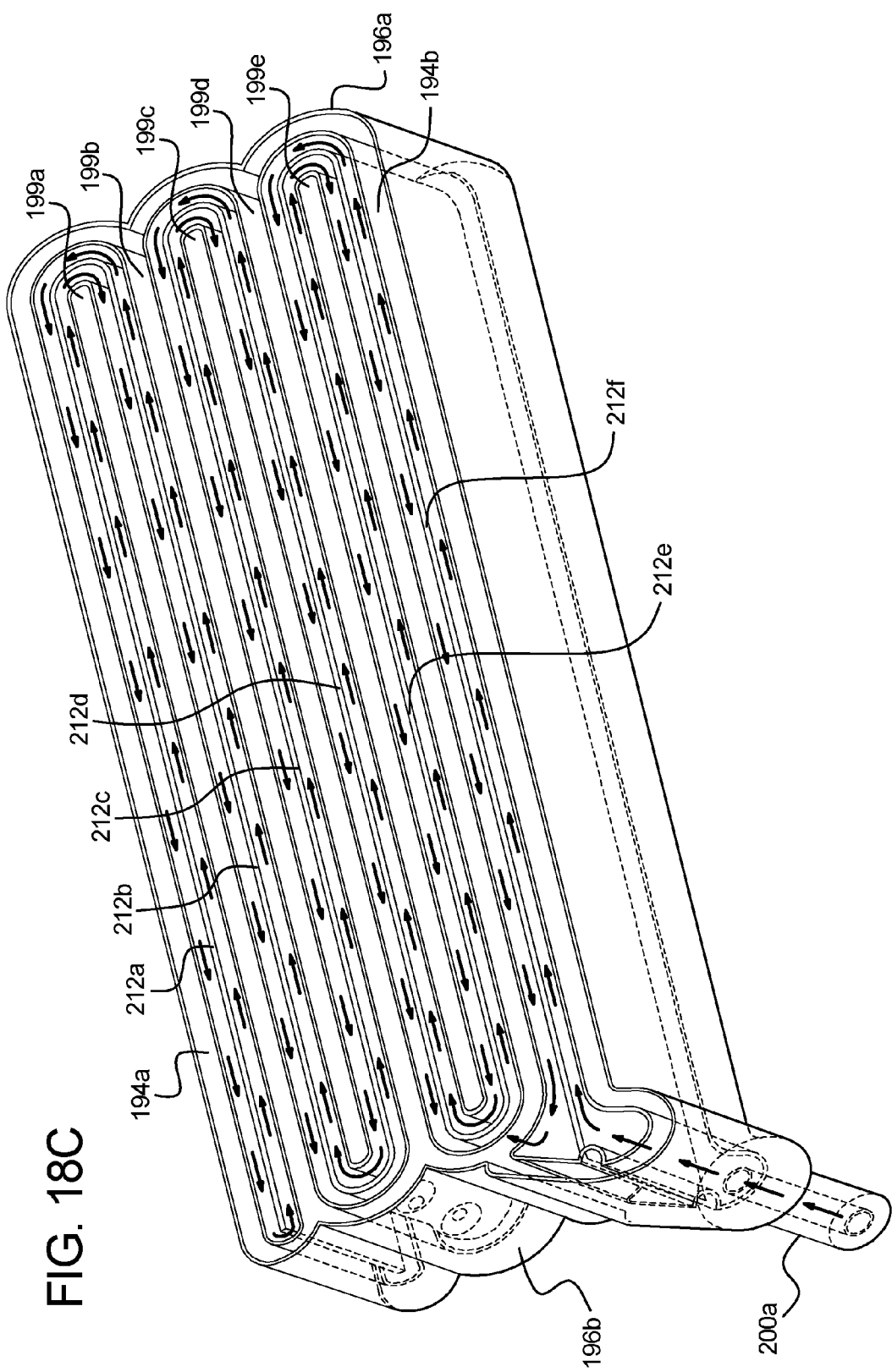

Referring now to FIGS. 18A to 18C, an alternative heating module 190, similar to heating module 150 is illustrated. Here, a serpentine path susceptor 212, made of a single sheet of metal, replaces plates 172 above, reducing the number of susceptor parts and allowing an average temperature of the susceptor to remain more constant over the entire fluid path.

The housing of heating module 190 includes a base 192 and a lid 202. Base 192 and lid 202 are made of any suitable insulating material described herein. Base 192 includes longer side walls 194a and 194b, shorter end walls 196a and 196b, and a bottom 198. Base also includes intervening insulating baffles 199a to 199g, which separate the different folds of bent metal susceptor 212.

At end wall 196b, base 192 includes or defines a dialysis fluid inlet 200a and a dialysis fluid outlet 200b. Dialysis fluid inlet 200a and dialysis fluid outlet 200b can be a suitable medical tube port connector as described above, which can connect heating module 190 directly to a disposable pumping and/or valving cassette or other part of a disposable set.

Lid 202 is generally flat and snap-fits to base 192. A gasket or soft compliant material can be compressed between lid 202 and base 192 to help provide a fluid-tight seal. Again, a medically safe, high temperature adhesive bond or ultrasonic weld could be used to seal lid 202 to base 192.

In the illustrated embodiment, heating module 190 employs six conductive baffle folds 212a to 212f from serpentine path susceptor 212 as its secondary coil. Serpentine path susceptor 212 can be stainless steel, e.g., magnetically susceptible stainless steel type 430. Folds 212a to 212f can be roughened or sintered to increase the turbulence of dialysis fluid flow. The illustrated embodiment shows that folds 212a to 212f have bumps (e.g., stamped) to increase the turbulence and thermal transfer from susceptor 212 to the dialysis fluid.

As seen by the arrows in FIG. 18A, dialysis fluid flow meanders back and forth along the length of insulating baffles 199a to 199e and along both sides of conductive folds 212a to 212f. In particular, cool fluid enters module 190 at port 200a. The fluid path forces the fluid to flow along the outside of conductive fold 212f until the fluid reaches end wall 196a of base 192, which forces the fluid to pass along the inside of conductive fold 212e until the fluid reaches the bend between folds 212e and 212d. The fluid passes along the outside of conductive fold 212d until the fluid reaches end wall 196a of base 192, which forces the fluid to pass along the outside of conductive fold 212c until the fluid reaches the bend between folds 212c and 212b. Then fluid passes along the inside of conductive fold 212b until the fluid reaches end wall 196a of base 192. The fluid further passes along the outside of conductive fold 212a until the fluid reaches end wall 196b of base 192. The fluid continues to pass along the inside of conductive fold 212a until the fluid reaches the bend between folds 212a and 212b, which forces the fluid to pass along the outside of conductive fold 212b until the fluid reaches end wall 196b of base 192. Finally, the fluid passes along the inside of conductive fold 212c until the fluid reaches the bend between folds 212c and 212d, which forces the fluid to pass along the inside of conductive fold 212d until the fluid reaches end wall 196b of base 192, which forces the fluid to pass along the outside of conductive fold 212e until the fluid reaches the bend between folds 212e and 212f, which forces the fluid to pass along the inside of conductive fold 212f until the fluid reaches end wall 196b of base 192 and fluid outlet 200b of lid 202.

The above path forces the warmest fluid (leaving outlet 200b) to contact the coolest fluid (entering inlet 200a) in a countercurrent arrangement. Such an arrangement tends to equalize the temperature over the entire susceptor 212 and tends to minimize hotspots.

Plate 212 is held fixed between base 192 and lid 202. The bottoms of folds 212a to 212f of plate 212 can fit frictionally into grooves (not shown) defined by a bottom 198 of base 192, and in which the tops of folds 212a to 212f of plate 212 fit frictionally into grooves (not shown) defined by lid 202. The free ends of outside baffle 212 can likewise fit frictionally into grooves (not illustrated) defined by the end 196b of base 192. The grooves can negate the need for an adhesive bond to hold plate 212 in a sturdy manner, although a medically safe, high temperature adhesive bond could be used.

The bumps on baffle folds 212a to 212f of susceptor 212 in one embodiment alternate direction from one side to another and are embossed to a height that maintains a constant spacing between insulating baffles 199a to 199g. Wedging the folds 212a to 212f between baffles 199a to 199g should eliminate the need for grooves or bonding to base 192.

Heating module 190 and baffles 212a to 212f can have dimensions similar to that module 150 of FIGS. 14A to 14E and module 180 of FIGS. 15A to 15E. FIG. 18C shows one serpentine flow path in which baffles 199a to 199e force dialysis fluid to flow along both sides of folds 212a to 212f, beginning at the outside of fold 212f and ending at the inside of fold 212f.

In one embodiment as shown in FIGS. 18A and 18B, the fluid heating system using heating module 190 winds a primary transformer coil 72 in a spiral or helical, e.g., solenoid-like, manner about assembled base 192 and lid 202, such that the axis of the coil as seen in FIGS. 18A and 18B is at least substantially parallel to the direction of the longer flat runs of baffles 212a to 212f. Alternatively, coil 72 is wound in any direction described herein in connection with the baffle modules. Helical coil 72 can spiral along any desired part and percentage of assembled base 192 and lid 202, leaving inlet 200a and outlet 200b exposed for connection to the disposable cassette or set. Primary coil 72 is powered via the electronics shown in FIG. 1 for example.

Heating module 190 is efficient from a magnetic and thermal standpoint. Metal susceptor 212 can be made relatively inexpensively and part count is minimal. Thinning the thickness of susceptor 212 and lowering the induction frequency increases the effects of current cancellation, making heating module 150 less efficient. A thinner susceptor 212, on the other hand, makes heating module 150 more responsive and less prone to overheating the dialysis fluid. Further, the number of folded baffles can be reduced and the same amount of power into the fluid can be achieved (same fluid heat rise and flowrate) by operating the folds at a higher temperature. These factors each play into the final dimensions chosen for heating module 190.

Cylindrical Heating Modules

Referring now to FIGS. 19A to 19D, heating module 230 illustrates one embodiment for an inductive cylinder heating module. Heating module 230 is configured to connect integrally to a disposable cassette, to a cassette via tubing or elsewhere to the disposable set as discussed above.

Heating module 230 includes a base 232 made of any of the insulating materials discussed herein. Base 232 includes an inner cylindrical wall 234, an outer cylindrical wall 236 and an annular bottom 238 connecting cylindrical walls 234 and 236 cylindrical walls 234 and 236 flare outwardly and inwardly, respectively, at their tops as seen in FIG. 19B to allow space for a cap 240 defining or including an inlet 242 and an outlet 244. Cap 240 can likewise be made of any of the insulating materials discussed herein. Inlet 242 and outlet 244 can further likewise be any of the types of tubing port connectors discussed herein.

Cap 240 is generally flat can and snap-fit, e.g., via outer lip 246, to base 232. A gasket or soft, compliant material can be compressed between cap 240 and base 232 to help provide a fluid-tight seal. Again, a medically safe, high temperature adhesive bond or ultrasonic weld could be used additionally or alternatively to seal cap 240 to base 232.

Cap 240 includes concentric lips 248 forming a groove between the lips for holding a top of susceptor or secondary coil 250, which can press-fit into the groove and/or be adhered to any contacting surface of cap 240. A portion 252 of bottom 238 of base 232 is filled with insulating material to additionally support secondary coil 250. Dialysis fluid flows around the bottom of secondary coil 250 in spots where bottom 238 of base 232 is not filled with insulating material (e.g., see left side of heating module 230 in FIG. 19B).

Cylindrical secondary coil 250 can be stainless steel, e.g., magnetically susceptible stainless steel 430. The coil can be roughened at its surfaces or be sintered to increase the turbulence of dialysis fluid flow. The coil can also have bumps (e.g., be stamped) to increase fluid flow turbulence.

When using a sintered metal filter material, the sintered secondary coil can extend all the way to the bottom 238 of cylindrical walls 234 and 236, such that fluid must flow through the thickness of the wall of the sintered metal susceptor instead of flowing around the bottom of the susceptor. A sufficient percentage of the sintered material can be left open so that at least a large portion of the dialysis fluid flows through the thickness of the cylinder, like the flow of air through a filter. The sintered metal filter provides a high surface area, high turbulence and low fluid volume to secondary surface area ratio, giving good thermal transfer properties.

Heating module 230 creates a dual annular fluid flow path in which fluid flows from inlet 242, longitudinally down the outside of secondary coil 250, around the bottom of secondary coil 250, and up the inside of secondary coil 250, before leaving heating module 230 via outlet 244. Inlet 242 and outlet 244 can be reversed such that fluid flows on the inside of secondary coil 250 before leaving heating module 230 along the outside of secondary coil 250.

In an embodiment, the disposable set or cassette including heating module 230 is inserted into the dialysis instrument such that heating module 230 is positioned directly on, or inside of a primary coil, e.g., outer coil 72 located within the instrument. When energized, primary coil 72 magnetically induces a current into the shorted susceptor 250, heating susceptor 250 and surrounding fluid. Primary coil 72 (in many embodiments disclosed herein) accordingly serves a secondary purpose of centering and steadying at least the heating portion of the cassette or disposable in operable position with the dialysis instrument.

Heating module 230 is considered to be a very good configuration from an electromagnetic standpoint. There is at least substantially no current cancellation, allowing susceptor 250 to be very thin, minimizing the stored heat in the susceptor and therefore reducing or eliminating the possibility of overheating the fluid if the flow stops before susceptor 250 has cooled down.

In the illustrated embodiment, base 232 has an outer diameter of about 1.99 inches (5.1 cm). Susceptor 250 has an outer diameter of about 1.75 inches (4.45 cm) and can be about 0.049 inch (1.2 mm) thick. The length y1 from the bottom of susceptor 250 to the flaring out of walls 234 and 236 (the length of the heating path in which fluid is forced to be close to susceptor 250) is about 1.93 inches (4.9 cm). The length y2 from the bottom of susceptor 250 to the top of the U of bottom 238 (the length of the return path beneath susceptor 250) is about 0.24 inch (6.1 mm). The length y3 from the top of susceptor 250 to the bottom of susceptor 250 is about 2.25 inches (5.72 cm).

Referring now to FIGS. 20A to 20E, heating module 260 illustrates another embodiment for an inductive cylinder heating module. Heating module 260 is configured to connect integrally to a disposable cassette, to a cassette via tubing or elsewhere to the disposable set as discussed herein.

Heating module 260 includes a base 262 made of any of the insulating materials discussed herein. Base 262 includes an inner cylindrical wall 264, an outer cylindrical wall 266 and an annular bottom 268 connecting cylindrical walls 264 and 266. Outer wall 236 flares outwardly as seen in FIGS. 20A and 20C to allow room for a cap 270 defining or including an inlet 272 and an outlet 274. Cap 270 can likewise be made of any of the insulating materials discussed herein. Inlet 272 and outlet 274 can further likewise be any of the types of tubing port connectors discussed herein.

Cap 270 is generally flat and can snap- or press-fit to the cylindrical walls of base 262 via concentric lips 278 (FIG. 20E). A gasket or soft, compliant material can be compressed between cap 270 and base 262 to help provide a fluid-tight seal. Again, a medically safe, high temperature adhesive bond or ultrasonic weld could be used additionally or alternatively to seal cap 270 to base 262.

Concentric lips 278 also form a groove between the lips for holding a top of susceptor or secondary coil 250 as described above. Susceptor 250 can also be adhered to any contacting surface of cap 270. Susceptor 250 is also centered and held between walls 264 and 266 via protruding dividers 276 extending outwardly and inwardly from base 262.

Cylindrical secondary coil 250 can be stainless steel, e.g., magnetically susceptible stainless steel 430. The coil can be roughened at its surface or sintered to increase the turbulence of dialysis fluid flow. The coil can also have bumps (e.g., be stamped) to increase fluid flow turbulence. Again, if susceptor 250 is made from a sintered metal filter type material, a significant percentage of the material can be left open so that at least a large portion of the dialysis fluid flows through the thickness of the cylinder, like the flow of air through a filter.

The primary difference with heating module 260 versus heating module 230 is that dividers 276 force the fluid to flow up and down different segments and on both sides of susceptor 250. Dividers 276 are staggered as seen in FIG. 20E, such that the fluid entering through inlet 272 is forced downwardly along a first outside pathway on the outside of susceptor 250, around the bottom of the susceptor 250, up a first inside pathway (which is in alignment with the first outside pathway) on the inside of susceptor 250, over the top of a divider 276 on the inside of susceptor 250. The fluid continues down a second, adjacent inside pathway, around the bottom of the susceptor 250, up a second outside pathway (which is in alignment with the second inside pathway and adjacent to the first outside pathway) on the outside of susceptor 250, over the top of a divider 276 on the outside of susceptor 250 (as seen in FIG. 20E). The fluid can further continue down a third outside pathway (adjacent to second outside pathway), and so on around susceptor 250 until exiting module 260 through outlet 274. Dividers 276 increase the contact time between fluid and susceptor 250, producing a more even flow around the susceptor and reducing hotspots.

Coil 72 in the illustrated embodiment is wound around heating module 260 as illustrated in FIG. 20E. Alternatively, coil 72 resides inside the inner insulating walls of heating modules 230 and 260.

In the illustrated embodiment, base 262 has an outer diameter of about 2.00 inches (5.08 cm). Susceptor 250 has an outer diameter of about 1.75 inches (4.4 cm) and can be about 0.049 inch (1.3 mm) thick. The height y1 from the top to the bottom of susceptor 250 is about 2.25 inches (5.71 cm). The height y2 from the top of cap 270 the bottom of base 262 is about 2.61 inches (6.63 cm). The height y3 from the top of inlet/outlet 272/274 to the bottom of base 262 is about 2.94 inches (7.5 cm).

Referring now to FIG. 21, heating module 280 illustrates one resistive heating system of the present disclosure. Heating module 280 includes a cylindrical insulating housing 282 made of any of the materials discussed herein. Housing includes a fluid inlet 284 and a fluid outlet 286. Fluid flow is shown generally via the arrows associated with element 288. Housing 282 is configured to connect integrally to a disposable cassette, to a cassette via tubing or elsewhere to the disposable set as discussed above.

In this resistive system, element 288 and corresponding baffles 290a to 290d are a thin plastic, disposable part, e.g., part of the cassette or disposable set, which transfers heat to the fluid and defines the fluid flow path between itself and a mating resistive heater 292, which is part of the dialysis instrument. Heater 292 includes circular, angled heat fins 294a to 294d, which mate with thin plastic baffles 290a to 290d of the cassette or disposable set to again provide a large surface contact area in a relatively small package.

To increase thermal transfer between resistive heater 292 and electrically insulating element 288, a conductive grease could be used to increase the heat transferred from resistive heater 292, through the insulator 288, to the fluid. A silicone rubber-based thermally conductive Sil-Pad® material or a thermally conductive conformable, low modulus polymer Gap-Pad® material by Berguist Company could be used alternatively, replacing the grease. Further alternatively, element 288 could be made of an electrically insulating, thermally conducting material, such as a Kapton® material. Further alternatively, element 288 could be made of a metal to efficiently transfer the heat energy to the fluid. In this case the electrical insulation isolating the main power source from the element 288 to be located elsewhere in the heating subsystem.

Referring now to FIG. 22, heating module 300 illustrates yet another alternative embodiment for an inductive cylinder heating module. Heating module 300 includes an outer cylindrical insulating shell 302, an inner cylindrical insulating shell 304 and a downwardly spiraling insulating baffle 306 sealed between shells 302 and 304. Disk-shaped top 308 and bottom 310 are also sealed to shells 302 and 304. Top 308 includes an inlet 312a. Bottom 310 includes an outlet 312b. Inlet 312a and outlet 312b can be of any connecting type described herein. All of the above items are made of an electrically insulating material, e.g., of any of the aforementioned plastics. Heating module 300 is configured to connect integrally to a disposable cassette, to a cassette via tubing or elsewhere to the disposable set as discussed herein.

A primary coil 314 can be a metal cylinder onto which heating module 300 is placed. Alternatively, the solid cylindrical primary coil wraps around the outside of heating module 300. Further alternatively, wire coil 72 (shown as an alternative in FIG. 22) wound around heating module 300 in the manner shown. In any case, the primary coil can be positioned to cover a part or all of heating module 300.

Fluid flows into heating module 300 via inlet 312a, down and around spiral baffle 306 and out outlet 312b. In this embodiment, heating module 300 does not include a conductive susceptor. Instead, the heating system relies on the conductivity of the dialysis fluid to become induced with current from the primary coil. Such a configuration is advantageous from a cost standpoint because the cost of the metal is spared. The configuration is disadvantageous from a practical standpoint because an input voltage of perhaps 140 Volts/cm might be needed to heat the fluid according to the parameters specified in connection with the test of the embodiment of FIGS. 14A to 14E.

In an alternative embodiment, shell 304 is metal, e.g., any of the types discussed herein, while shell 302 and spiral baffle 306 are plastic. Further alternatively, outer shell 302 is plastic, while one or both of inner shell 304 and spiral baffle 306 are metal or metalized, e.g., any of the metals discussed herein. The metal parts provide a susceptor induced via primary coils 314 or 72 discussed above.

Figure 23:
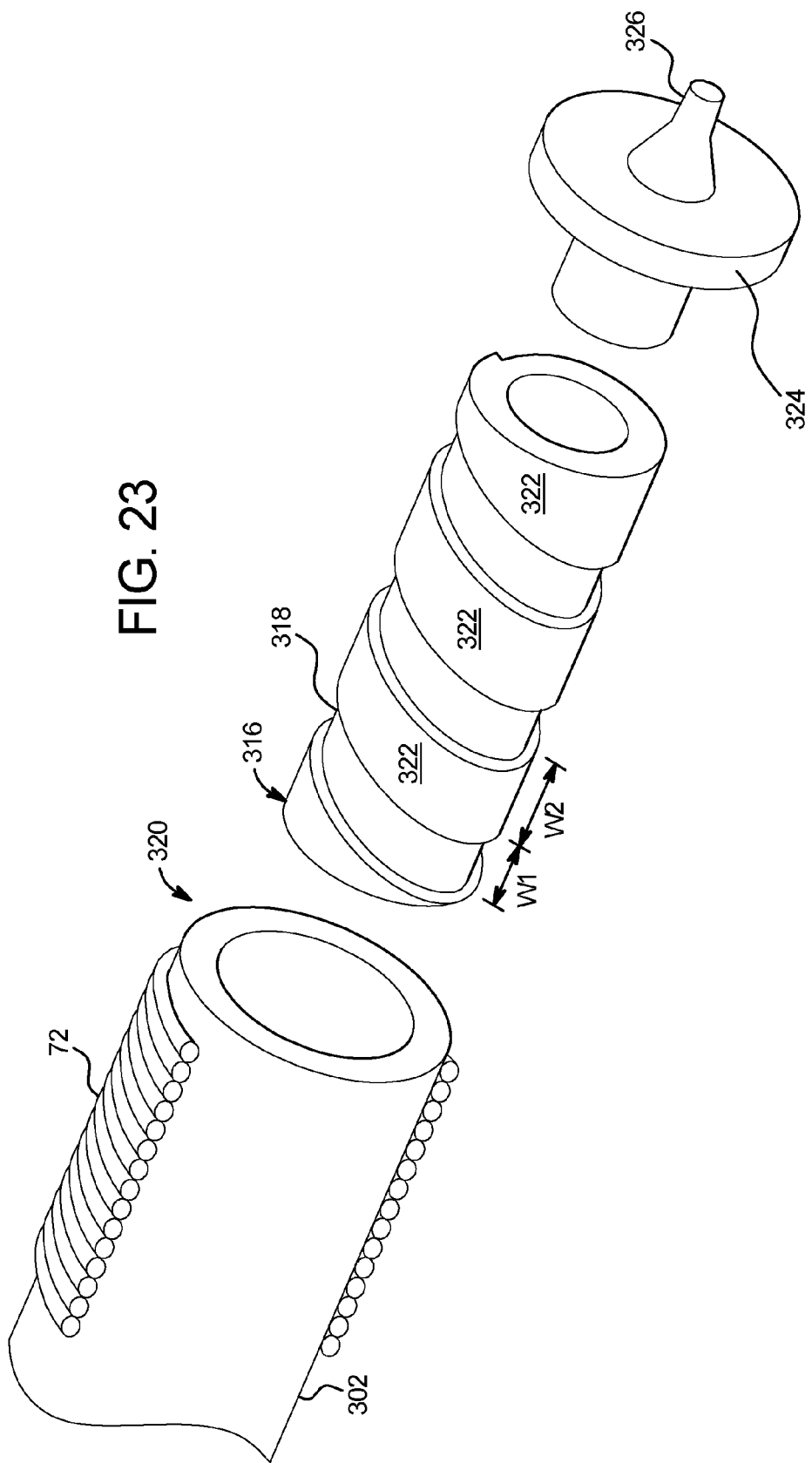
FIG. 23 is a perspective view of yet a further embodiment of an inductive cylindrical fluid heating module.

Referring now to FIG. 23, heating module 320 illustrates yet another alternative embodiment for an inductive cylinder heating module. Heating module 320 includes an outer cylindrical insulating shell 302 and a susceptor 316 that fits snugly within insulating shell 302. Susceptor 316 can be any of the metals described herein. Susceptor 316 has an inner spiraling flow path portion 318 and an outer spiraling machine screw type baffle 322. The pitch, frequency and relative width w1 of path 318 versus width w2 of baffle 322 are chosen to maximize performance. Path 318 can have turbulating features, such as stainless steel mesh or wool.

Disk-shaped ends 324 (one shown) couple to shell 302 and have an inlet/outlet 326 (one shown). Path 318 communicates with inlet 326 and outlet 326. Inlet/outlet 326 can be of any type described herein and can be made of an electrically insulating material, e.g., of any of the aforementioned plastics. Heating module 300 is configured to connect integrally to a disposable cassette, to a cassette via tubing or to elsewhere to the disposable set as discussed above.

In an alternative embodiment, baffle 322 is replaced with stainless steel, e.g., type 316 or 430, wool or mesh (not illustrated) which can extend between ends 324. Here, inner portion 318 is plastic. A further alternative module (not illustrated) fills, e.g. no inner insulator, an insulating tube with metal wool or mesh and places end caps at the ends of the tube. The metal wool or mesh operates as the susceptor. In any case, a spiral primary coil 72 can be wound around outer tube 302 as shown.

Figure 24:
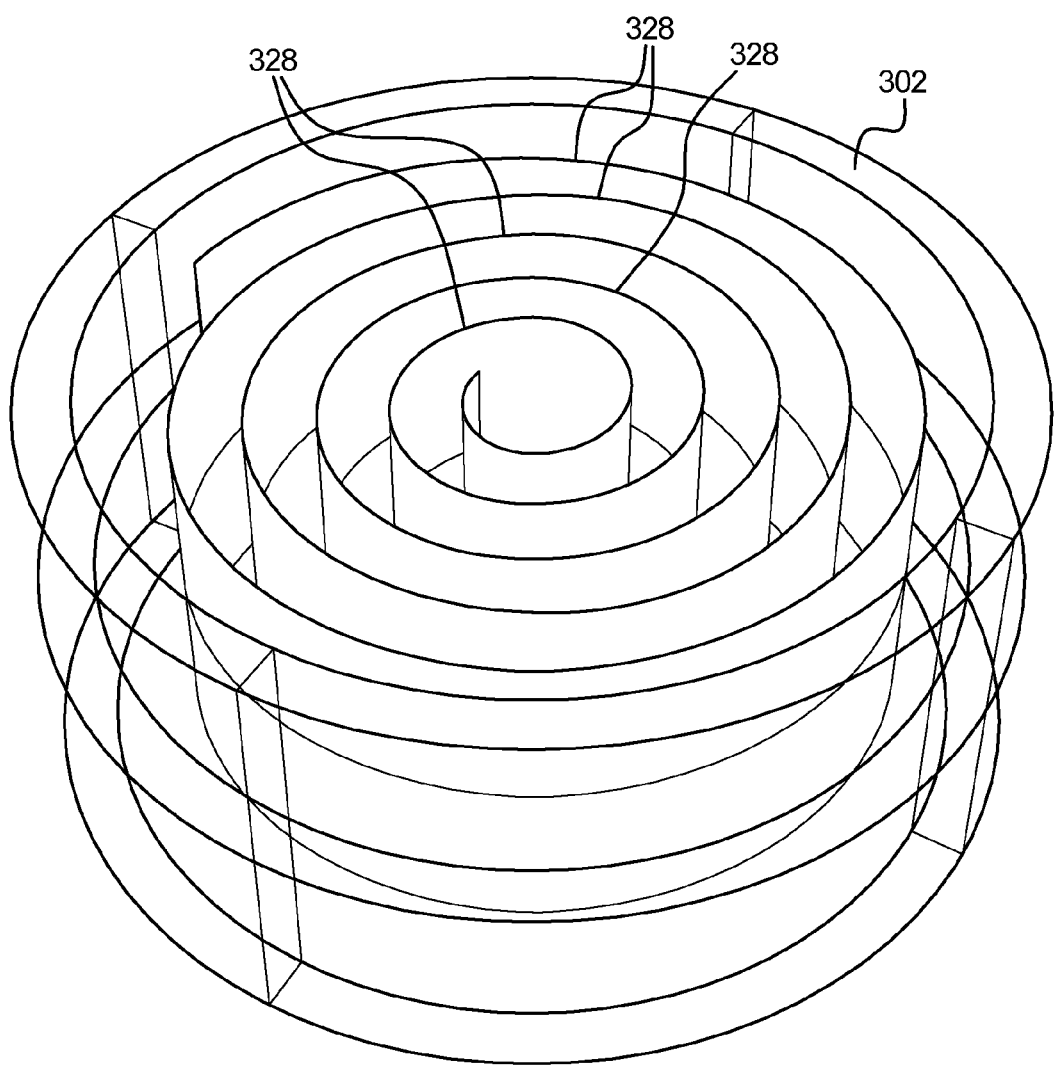
FIG. 24 is a perspective view of still another embodiment of an inductive cylindrical fluid heating module.

Referring now to FIG. 24, susceptor 328 illustrates another possible susceptor for an inductive cylinder fluid heating module. Susceptor 328 fits inside an insulating housing 302 as illustrated. Susceptor 328 is a single piece of metal wound in a spiral manner as illustrated. Susceptor 328 can have bumps or other turbulating devices or can be sintered. Fluid flows between the different spiral layers in a parallel manner. Housing 302 can be wound with a primary coil 72 as shown herein.

Tubing Heating Modules

Referring now to FIGS. 25A to 25E, heating module 330 illustrates one possible secondary coil and housing embodiment that uses conductive heating tubes. Heating module 330 flows fluid on both sides of the tube to maximize the heat transfer from the susceptor to the fluid. The housing of heating module 330 includes a base 332, an end cap 340 and a lid 350. Base 332, end cap 340 and lid 350 are made of a suitable medical grade at least relatively high-melting temperature plastic, such as polycarbonate, polysulfone, urethane or potentially other high temperature plastics.

Base 332 includes a bottom 334 and semi-circular walls 336a to 336e extending from bottom 334 and having a diameter slightly larger than that of tubes 338a to 338e placed within base 332.

Lid 350 includes or defines a dialysis fluid inlet 352 and a dialysis fluid outlet 354. Dialysis fluid inlet 352 and dialysis fluid outlet 354 can be any suitable medical tube port connector, such as a luer connector or a hose barb connector. Dialysis fluid inlet 352 and dialysis fluid outlet 354 can connect heating module 330 directly to a disposable pumping and/or valving cassette for example. Dialysis fluid inlet 352 and dialysis fluid outlet 354 alternatively connect heating module 330 to another part of a disposable dialysis set, such as one for peritoneal dialysis or hemodialysis, such as inline with a supply line or patient line. It should be appreciated that any of the fluid heating embodiments described herein can be used to heat an already mixed dialysate or a fluid component or concentrate used in making dialysate.

Figure 25A:
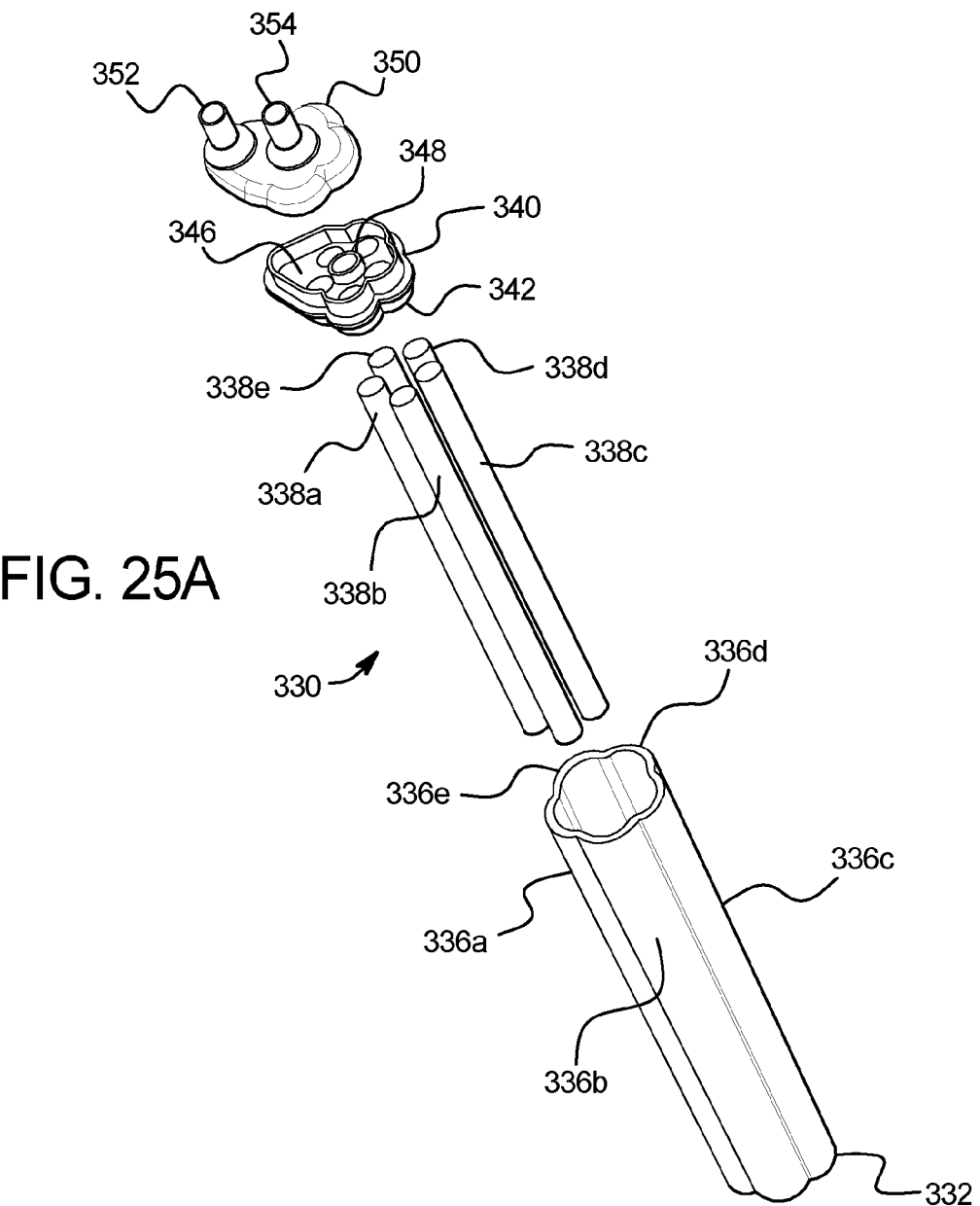
FIG. 25A illustrates various parts of one embodiment of a secondary coil fluid heating module of the present disclosure using multiple heating tubes.
Figure 25B:
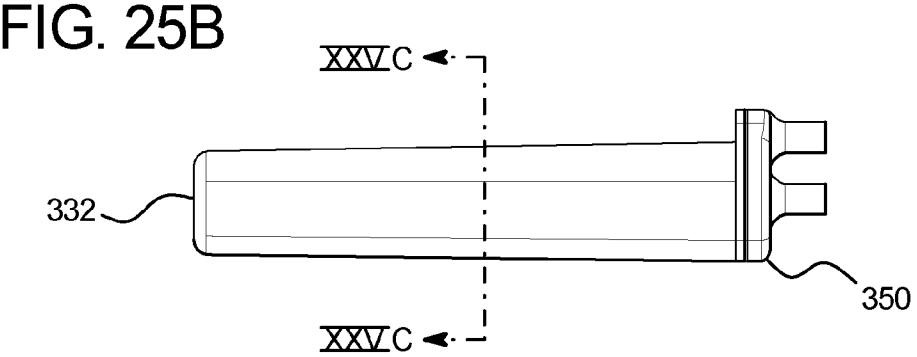
FIG. 25B is a side view of the assembled fluid heating module of FIG. 25A.

FIG. 25A illustrates that heating module 330 employs five conductive tubes 338a to 338e (referred to herein collectively as conductive tubes 338 and individually, generally as tube 338) as its secondary coil. Conductive tubes 338 can be stainless steel, e.g., magnetically susceptible stainless steel 430, or non-magnetically susceptible stainless steel 304. The tubes can be roughened or sintered to increase the turbulence of dialysis fluid flow. Tubes 338 are all the same in the illustrated embodiment.

Each tube 338 is fixed at its upper end to a circular collar 342 (FIGS. 25A and 25E) of end cap 340. The ends of tubes 338 fit frictionally into collars 342. A suitable adhesive bond can also be used to hold tubes 338 within collars 342. The bottom ends of tubes 338 are supported by supports 344 (see FIGS. 25C and 25E), which give support but allow dialysis fluid to flow out the bottom of tubes 338 into the bottom of base 332.

The upper part of end cap 340 defines a manifold area 346 in which fluid fills after entering heating module 330 from inlet 352. Collars 342 define apertures leading from manifold area 346 into tubes 338 as seen best in FIG. 25E. End cap 340 also includes an outlet port 348, which is placed in operable communication with outlet 354 as seen best in FIG. 25E.

In the illustrated embodiment, base 332 and lid 350 combined are about 3.47 inches long (8.81 cm) (total length to end of inlet/outlet 3.80 about inches 9.65 cm). Base 332 is about 0.74 inch (19 mm) in diameter at its widest point. Tubes 338 are all the same in the illustrated embodiment. In the illustrated embodiment, tubes 338 are three inches long (7.62 cm), have about an 0.156 (4 mm) outside diameter and are about 0.010 inch (0.25 mm thick). Tubes 338 are spaced apart equally along a center-circle having a diameter of about 0.34 inch (8.6 cm) as seen in FIG. 25C.

With heating module 330, dialysis fluid flow enters through inlet 352, fills manifold area 346, flows down each of tubes 338 simultaneously, out the bottom of the tubes, returns along the outside surface of the tubes, and leaves heating module 330 through outlet port 348 and outlet 354. In this manner, the fluid flows through all of tubes 338 in parallel and returns on the outside surface of the tubes in parallel.

Figure 25C:
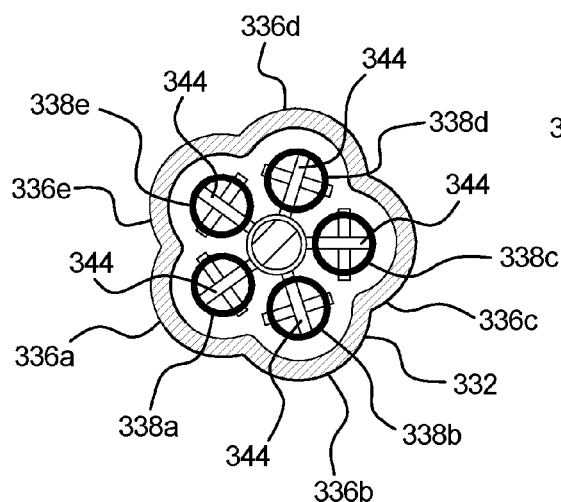
FIG. 25C is a plan-sectioned view of the base and installed tubes taken along line XXV C-XXV C of FIG. 25B.
Figure 25D:
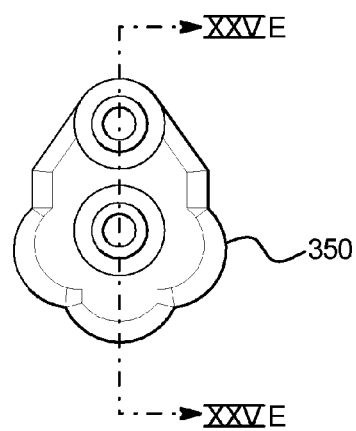
FIG. 25D is a top plan view of the assembled fluid heating module of FIG. 25A.
Figure 25E:
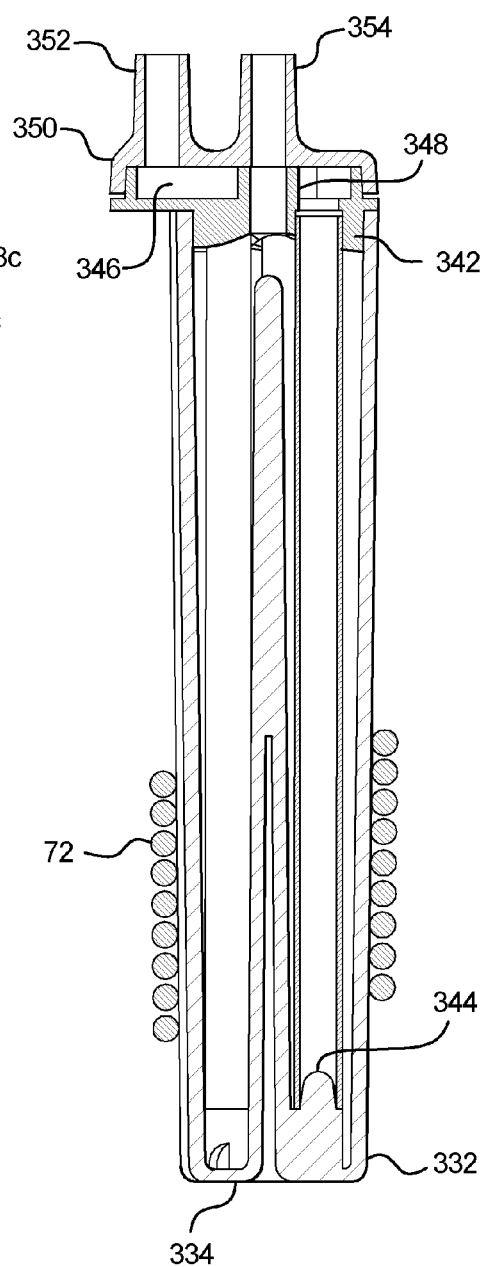
FIG. 25E is an elevation-sectioned view of the base and installed tubes plates taken along line XXV E-XXV E of FIG. 25D.

The mating semicircles 336a to 336e force the return flow closer to the outer surface of tubes 338 as seen in FIG. 25C. Alternatively, base 332 has a rounded cross-sectional shape, that is, does not provide semicircles 336a to 336e.

In one embodiment, the fluid heating system using heating module 330 winds a primary transformer coil 72 in a spiral or helical, e.g., solenoid-like manner about base 332. The helical coil 72 can spiral along any desired part and percentage of base 332, leaving inlet 352 and outlet 354 exposed for connection to the disposable cassette or set. The induction coil 72 is wound such that the axis of coil, 72 is at least substantially parallel to the axis of the tubes 338 in the illustrated embodiment. The primary coil 72 can be powered via the electronics 24 shown in FIG. 1 for example.

Heating module 330 is efficient from a magnetic and thermal standpoint. Metal tubes 338 can be made relatively inexpensively and the overlay part count is minimal. Relatively thin tube walls allow heating module 330 to be responsive to fluid inlet temperature and flow fluctuations. These factors each play into the final dimensions, operating temperature and number of tubes chosen for heating module 330.

The number of tubes 338 can be reduced and the same amount of power into the fluid can be achieved (same fluid heat rise and flowrate) by operating the tubes 338 at a higher temperature. The number of tubes can alternatively be increased (see e.g., FIGS. 27A to 27D below). The size of the tubes can also be changed. The fluid flow could be reversed so that the return path is through the center of the tubes, which may be beneficial if the outer surfaces of the tubes carry most of the current. Here, the hottest part of the tubes (the outer surface) meets the coldest dialysis fluid in a counterflow arrangement.

In a further alternative embodiment, fluid flow is confined to the outside of the tubes 338, leaving the inside of the tubes dry. This would allow a temperature probe to contact the inside of the tubes to measure the tubing temperature. Alternatively, as discussed below, the resistance of the tubing can be determined by applying a voltage or current to the tubes and measuring the other of the current or voltage. The resistance of the tubing varies with temperature allowing tubing temperature to be correlated and determined.

Referring now to FIGS. 26A to 26E, heating module 360 illustrates another possible secondary coil and housing embodiment that uses conductive heating tubes. Heating module 360 flows fluid on the insides of tubes 338*a* to 338*f* only. The instrument can measure the temperature of the tubing at the dry outside portion of tubes 338 using either a sensor (e.g., an infrared temperature sensor, diode, thermistor, integrated circuit sensor, or resistance temperature device ("RTD")) or via resistance correlation as discussed herein. Because the tubing is metal and therefore highly thermally conductive, the instrument can determine the fluid temperature from the tubing temperature relatively accurately.

Heating module 360 includes an inlet/outlet manifold 362, an end cap 370 secured to manifold 362, a return manifold 380 and an end cap 390 secured to return manifold 380. Each of these components can be made of a suitable medical grade at least relatively high-melting temperature plastic, such as those described above.

Cap 370 includes or defines a dialysis fluid inlet 372 and a dialysis fluid outlet 374, which can be reversed from the order shown in the FIGS. 26A to 26E. Dialysis fluid inlet 372 and dialysis fluid outlet 374 can be any suitable medical tube port connector, such as a luer connector or a hose barb connector. For example, dialysis fluid inlet 372 and dialysis fluid outlet 374 can connect heating module 360 directly to a disposable pumping and/or valving cassette for example. Dialysis fluid inlet 372 and dialysis fluid outlet 374 alternatively connect heating module 360 to another part of a disposable dialysis set, such as one for peritoneal dialysis or hemodialysis. For example, dialysis fluid inlet 372 and outlet 374 can connect module 360 in line with a supply line or patient line. It should be appreciated that any of the fluid heating embodiments described herein can be used to heat an already mixed dialysate or a fluid component or concentrate used in making dialysate.

Caps 370 and 390 can be snap-fitted, and/or adhesively bonded or ultrasonically welded to manifolds 362 and 380, respectively. Alternatively, caps 370 and 390 are formed integrally with manifolds 362 and 380, respectively.

Figure 26A:
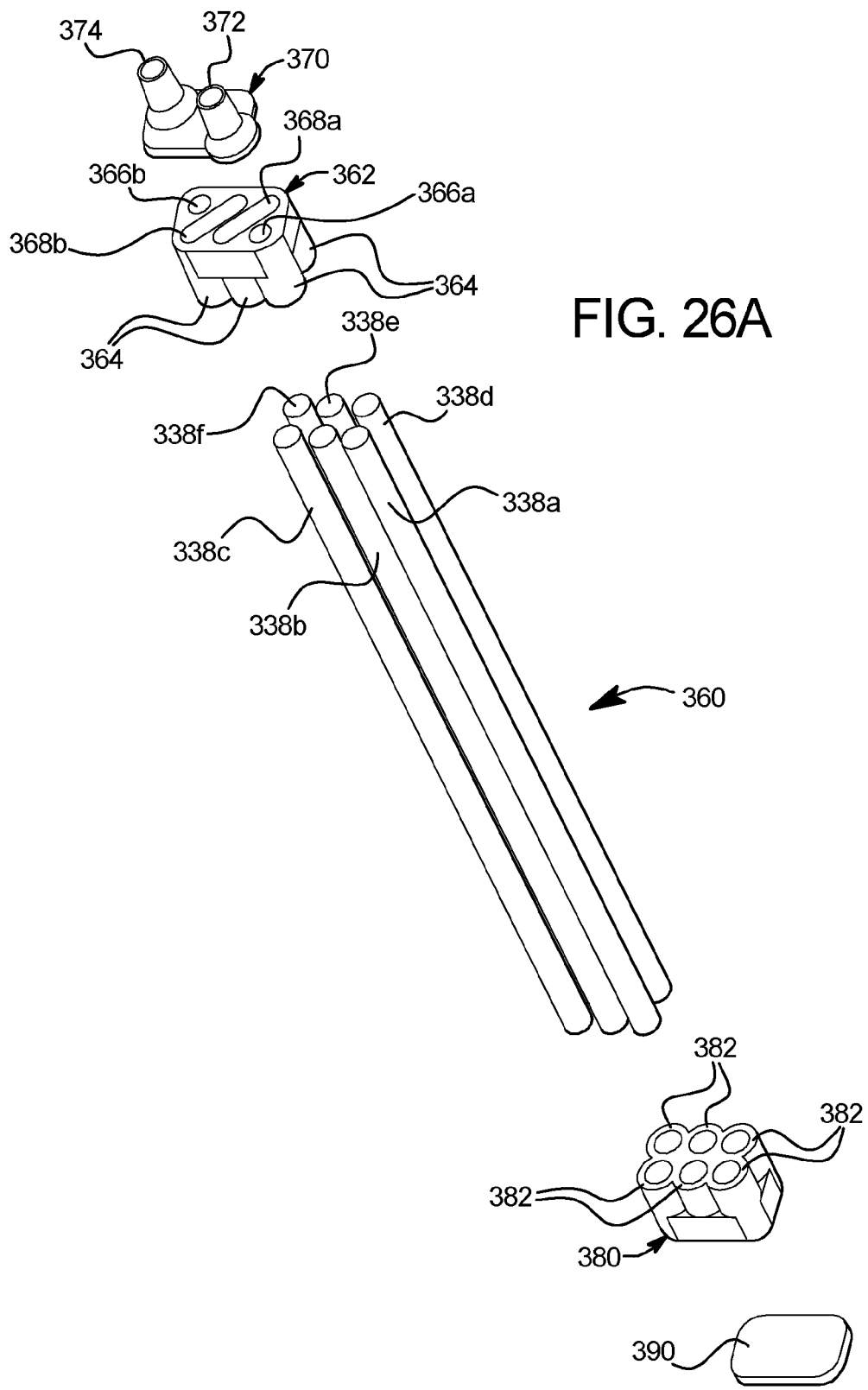
FIG. 26A illustrates various parts of another embodiment of a secondary coil fluid heating module of the present disclosure using multiple heating tubes.

FIG. 26A illustrates that heating module 360 employs six conductive tubes 338*a* to 338*f* (referred to herein collectively as conductive tubes 338 and individually, generally as tube 338) as its secondary coil. Conductive tubes 338 can be stainless steel, e.g., magnetically susceptible stainless steel 430, or non-magnetically susceptible stainless steel 304. The tubes 338 can be roughened or sintered to increase the turbulence of dialysis fluid flow. Tubes 338 are all the same in the illustrated embodiment.

Each tube 338 is fixed at its upper end to manifold 362. The ends of tubes 338 fit frictionally into collars 364 of manifold 362 as shown in FIG. 26E. A suitable adhesive bond can also be used to hold tubes 338 within collars 364. The bottom ends of tubes 338 are likewise fitted frictionally to return manifold 380. The ends of tubes 338 fit frictionally into collars 382 of manifold 380. A suitable adhesive bond can also be used to hold tubes 338 within collars 382.

As seen in FIG. 26A, inlet/outlet manifold 362 defines inlet aperture 366*a*, which communicates with inlet 372 of cap 370 and inlet tube 338*a*. Manifold 362 defines outlet aperture 366*b*, which communicates with outlet 374 of cap 370 and outlet tube 338*f*. Manifold 362 further defines diagonal slot 368*a*, which communicates with tubes 338*b* and 338*d*, and diagonal slot 368*b*, which communicates with tubes 338*c* and 338*e*.

As further seen in FIG. 26E, return manifold 380 defines three right angle apertures 384 (only one seen in FIG. 26E), which allow a tube in the front row of three tubes to communicate fluidly with its corresponding tube in the rear row of three tubes. In other words, right angle apertures 384 allow tube 338*a* to communicate fluidly with tube 338*d*, tube 338*b* to communicate fluidly with tube 338*e*, and tube 338*c* to communicate fluidly with tube 338*f*.

In the illustrated embodiment, outside manifold to outside manifold distance is about 5.52 inches (14 cm). Manifolds 362 and 380 are about 0.45 inch (1.1 cm) long. In the illustrated embodiment, tubes 338 are about five inches long (12.7 cm), have about an 0.156 (4 mm) outside diameter and are about 0.010 inch (0.25 mm thick). Outer tubes 338*a* and 338*c* (338*d* and 338*f*) have a center-to-center distance of about 0.39 inch (1.0 cm). Tubes 338*a* and 338*d* (338*b* and 338*e*, 338*c* and 338*f*) have a center-to-center distance of about 0.20 inch (0.5 cm).

With heating module 360, dialysis fluid flow enters through inlet 372, flows through aperture 366*a*, through tube 338*a*, through a right angle manifold 384 to tube 338*d*. The fluid continues through tube 338*d*, to diagonal slot 368*a*, to tube 338*b*, through tube 338*b*, through a right angle manifold 384 to tube 338*e*. The fluid then flows through tube 338*e*, to diagonal slot 368*b*, to tube 338*c*, through tube 338*c*, through a right angle manifold 384, to tube 338*f*. The fluid continues through tube 338*f*, through aperture 366*b*, to and out outlet 374. In this manner, the fluid flows through tubes 338 in series.

In one embodiment, the fluid heating system using heating module 360 winds a primary transformer coil 72 in a spiral or helical, e.g., solenoid-like, manner about tubes 338 via an insulating jacket (example shown below in FIGS. 28A to 28D). The helical coil 72 can spiral along any desired part and percentage of tubes 338, leaving inlet 372 and outlet 374 exposed for connection to the disposable cassette or set. The induction coil is wound such that the axis of coil 72 is at least substantially parallel to the axis of the tubes 338. The primary coil 72 is powered via the electronics shown in FIG. 1 for example.

Heating module 360 is efficient from a magnetic and thermal standpoint. Metal tubes 338 can be made relatively inexpensively and the overall part count is minimal. Module 360 can have relatively thin tube walls, making the heating module 360 more responsive. The thin walls do not store as much energy, making the module better able to cope with a fluid flow stoppage or gas bubble.

The number of tubes 338 can be reduced and the same amount of power into the fluid can be achieved (same fluid heat rise and flowrate) by operating tubes 338 at a higher temperature (see e.g., FIGS. 27A to 27D below). The number of tubes can alternatively or additionally be increased. The size of tubes 338 can be changed.

In a further alternative embodiment (not shown), a combination parallel and series module is provided in which, for example, fluid travels first from manifold 362, through tubes 338a and 338d, to manifold 380, then back though tubes 338b and 338e to manifold 362, then again down through tubes 338c and 338f to manifold 380 and out manifold 380. This arrangement could simplify the structure of manifolds 362 and 380. It is also accordingly expressly contemplated to provide inlet 372 on one end and outlet 374 on a second end of module 360 and indeed any of the modules discussed herein. Inlets and outlets for any of the modules can be inline as shown with module 360 or at a right angle as shown below for example with module 420 of FIGS. 28A to 28G.

Referring now to FIGS. 27A to 27D, heating module 400 illustrates a further possible secondary coil and housing embodiment that uses conductive heating tubes. Heating module 400 is a two-tube version of heating module 360 and likewise flows fluid on the inside of tubes 338a and 338b only. The instrument can measure the temperature of the tubing at the dry outside portion of tubes 338 using either a sensor (e.g., an infrared temperature sensor, diode, thermistor, integrated circuit sensor, or resistance temperature device ("RTD")) or via resistance correlation as discussed herein. Because the tubing is metal and therefore highly thermally conductive, the instrument can determine the fluid temperature from the tubing temperature relatively accurately.

Heating module 400 includes an inlet/outlet manifold 402 having an integral end cap, a return manifold 410 and an end cap 390 secured to return manifold 410. Each of these components can be made of a suitable medical grade at least relatively high-melting temperature plastic, such as those described above.

Manifold 402 includes or defines a dialysis fluid inlet 404 and a dialysis fluid outlet 406, which can be reversed from the order shown in the FIGS. 27A to 27D. Dialysis fluid inlet 404 and dialysis fluid outlet 406 can be any suitable medical tube port connector, such as a luer connector or a hose barb connector. Dialysis fluid inlet 404 and dialysis fluid outlet 406 can connect heating module 400 directly to a disposable pumping and/or cassette for example. Dialysis fluid inlet 404 and dialysis fluid outlet 406 alternatively connect heating module 400 to another part of a disposable dialysis set, such as one for peritoneal dialysis or hemodialysis. For example, dialysis fluid inlet 404 and outlet 406 can connect module 400 in line with a supply line or a patient line. It should be appreciated that any of the fluid heating embodiments described herein can be used to heat an already mixed dialysate or a fluid component or concentrate used in making dialysate.

Cap 390 can be snap-fitted and/or bonded to or ultrasonically welded to manifold 410. Alternatively, cap 390 is formed with manifold 410. FIG. 27A illustrates that heating module 400 employs two conductive tubes 338a and 338b (referred to herein collectively as conductive tubes 338 and individually, generally as tube 338) as its secondary coil. Conductive tubes 338 can be stainless steel, e.g., magnetically susceptible stainless steel 430, or non-magnetic stainless steel 304. Tubes 338 can be roughened on the inside to increase the turbulence of dialysis fluid flow. Tubes 338 can all be the same in the illustrated embodiment.

Each tube 338 is fixed at its upper end to manifold 402. The ends of tubes 338 fit frictionally into collars 408 of manifold 402. A suitable adhesive bond can also be used to hold tubes 338 within collars 408. The bottom ends of tubes 338 are likewise fitted frictionally to return manifold 410. The ends of tubes 338 fit frictionally into collars 412 of manifold 410. A suitable adhesive bond can also be used to hold tubes 338 within collars 412.

As seen in FIG. 27C, return manifold 410 defines a right angle manifold 384, which allows tube 338a to communicate fluidly with tube 338b. In the illustrated embodiment, total length l of heating module 400 is about 2.64 inches (6.7 cm) and total width w is about 0.71 inch (1.80 cm). In the illustrated embodiment, tubes 338 are two inches long (5.1 cm), 0.156 (4 mm) outside diameter and 0.010 inch (0.25 mm) thick).

With heating module 400, dialysis fluid flow enters through inlet 404, flows through tube 338a, through a right angle manifold 384, to tube 338b, through tube 338b and out outlet 406. Here again, the fluid flows through tubes 338 in series.

In one embodiment, the fluid heating system using heating module 400 winds a primary transformer coil 72 in a spiral or helical, e.g., solenoid-like manner about tubes 338 via an insulating jacket (example shown below in FIGS. 28A to 28D). The helical coil 72 can spiral along any desired part and percentage of tubes 338, leaving inlet 404 and outlet 406 exposed for connection to the disposable cassette or set. The induction coil is wound in one embodiment such that the axis of coil 72 is at least substantially parallel to the axis of the tubes 338. The primary coil 72 is powered via the electronics shown in FIG. 1 for example. The six tube module 360 above can be operated at a constant tubing temperature of about 55° C., while the two tube module 400 can be operated at a constant tubing temperature of about 75° C., both producing the same fluid temperature rise at a constant flowrate.

A fluid heating module very similar to heating module 400 was tested using the electronic circuits from a customized Ameritherm Hot Shot™ power supply. The primary coil 72 used was wound 13.5 turns in a helical manner around the housing of the heating module, such that the axis of the helical coil was at least substantially parallel to the length of tubes. Coil 72 was 1050 strands of 42 AWG Litz wire. With water passing through the disposable at a rate of about 250 ml/min, the heating module 400 heated water from 24.2° C. to 46.7° C., which indicates that the heating module 400 inputs power into the water at about 393 Watts. The power that the AC mains inputs into the hot plate primary was measured at about 440.2 Watts. This indicates an efficiency of about 89%.

Heating module 400 is efficient from a magnetic and thermal standpoint. Metal tubes 338 can be made relatively inexpensively and the overall part count is minimal. Again, module 400 can have relatively thin tube walls, making the heating module 400 more responsive. The thin walls do not store as much energy, making the module 400 better able to cope with a fluid flow stoppage or a gas bubble. Module 400 could be changed to a single tube which is bent into a U-shape, eliminating manifold 410. Module 360 can likewise be modified to be a single tube bent multiple times.

Referring now to FIGS. 28A to 28F, heater 420 illustrates a further possible embodiment that uses conductive heating tubes. Heater 400 is again a two-tube version of heating module 360 and likewise flows fluid on the inside of tubes 338a and 338b only. The instrument can measure the temperature of the tubing at the dry outside portion of tubes 338 using either a sensor (e.g., an infrared temperature sensor, diode, thermistor, integrated circuit sensor, or resistance temperature device ("RTD")) or via resistance correlation as discussed herein. Because the tubing is metal and therefore is highly thermally conductive, the instrument can determine the fluid temperature from the tube temperature relatively accurately.

Figure 28D:
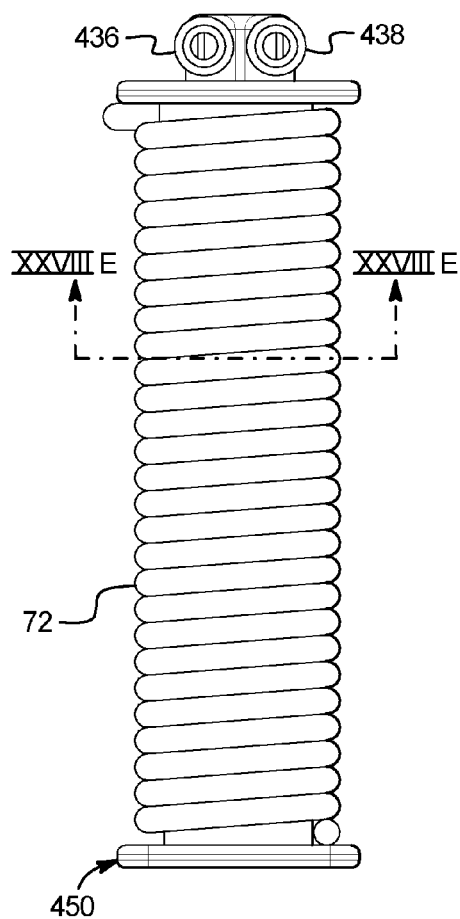
FIG. 28D is a front elevation view of the heater module of FIG. 28A showing wound primary coil.
Figure 28E:
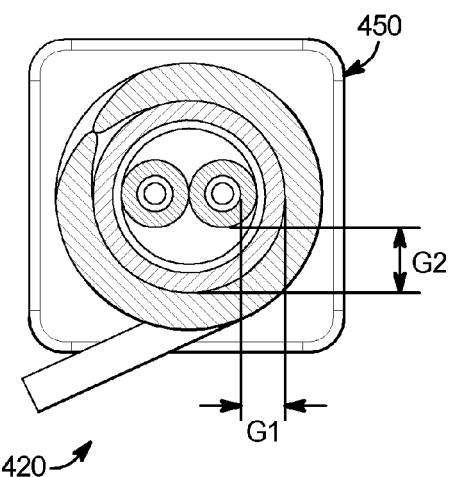
FIG. 28E is a bottom-sectioned view of the heater of FIG. 28A taken along line XXVIII E-XXVIII E of FIG. 28D.
Figure 28F:
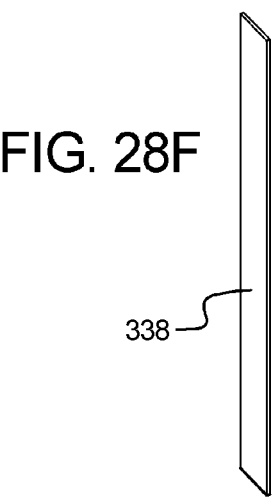
FIG. 28F is a side elevation view of one embodiment of a heating tube of the heater of FIG. 28A.
Figure 28G:
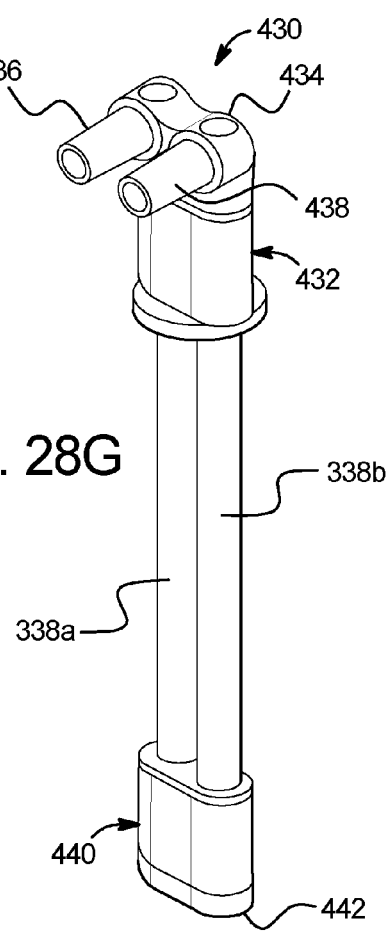
FIG. 28G is a perspective view of a heating module used with the heater of FIG. 28A.

Heater 420 includes a fluid heating module 430 shown most clearly in FIG. 28G. Module 430 includes an inlet/outlet manifold 432 with an integral end cap 434, a return manifold 440 having an end cap 442 secured to return manifold 440. Cap 442 can be welded ultrasonically to manifold 440 as seen in FIG. 28C via at least one ultrasonic energy concentrator as described above. Each of these components can be made of a suitable medical grade at least relatively high-melting temperature plastic, such as those described above.

End cap 434 of manifold 432 includes or defines a dialysis fluid inlet 436 and a dialysis fluid outlet 438, which can be reversed from the order shown in the FIGS. 28A to 28G. Dialysis fluid inlet 436 and dialysis fluid outlet 438 can: (i) be any suitable medical tube port connector, such as a luer connector or a hose barb connector; (ii) connect heating module 430 directly to a disposable pumping and/or valving cassette; or (iii) alternatively connect heating module 430 such as in line with a supply line or a patient line to another part of a disposable dialysis set, such as one for peritoneal dialysis or hemodialysis. In the illustrated embodiment, inlet 436 and outlet 438 are oriented at a right angle with respect to tubes 338, which may be advantageous for mounting heater 420 as shown below.

FIGS. 28B, 28C and 28G illustrate that heating module 430 employs two conductive tubes 338a and 338b (referred to herein collectively as conductive tubes 338 and individually, generally as tube 338) as its secondary coil. Conductive tubes 338 can be stainless steel, e.g., magnetically susceptible stainless steel 430, or non-magnetic stainless steel 304 or 316. Tubes 338 can be roughened on the inside to increase the turbulence of dialysis fluid flow. Tubes 338 can all be the same in the illustrated embodiment.

Each tube 338 is fixed at its upper end to manifold 432. The top ends of tubes 338 fit frictionally into collar 444 of manifold 432. A suitable adhesive bond can also be used to hold tubes 338 within collars 444. The bottom ends of tubes 338 are likewise fitted frictionally into collars 446 of return manifold 440. A suitable adhesive bond can also be used to hold tubes 338 within collars 446.

As seen in FIG. 28C, return manifold 440 allows tube 338a tube to communicate fluidly with tube 338b. Tubes 338 are angled at their ends (FIGS. 28B, 28C and 28F), e.g., at forty-five degrees, to direct flow towards a desired destination or accept flow from a particular direction.

With heating module 430, dialysis fluid flow enters through inlet 436, enters tube 338a through an angled tube inlet, flows through tube 338a, out angled outlet of tube 338a. The fluid continues through manifold 440, to angled inlet of tube 338b, through tube 338b, out angled outlet of tube 338b, and out outlet 436. Here again, the fluid flows through tubes 338 in series.

As seen in FIGS. 28A to 28D, fluid heater 420 using heating module 430 winds a primary transformer coil 72 in a spiral or helical, e.g., solenoid-like manner about tubes 338 around an insulating jacket 450 insulating jacket 450 is seen best in FIGS. 28B and 28C and is located between tubes 338 and coil 72. Jacket 450 includes flanged ends that help to hold coil 72 in place. Jacket, like coil 72, is provided with the dialysis instrument in one embodiment. Helical coil 72 can spiral along any desired part and percentage of tubes 338, here between the flanges of jacket 450, leaving inlet 436 and outlet 438 exposed for connection to the disposable cassette or set. As illustrated, induction coil 72 is wound such that the axis of coil 72 is at least substantially parallel to the axis of tubes 338.

In any embodiment herein having a generally elongated susceptor and coil 72, coil 72 can extend past the susceptor at one or both ends. For example, tubes 338 can be three inches (7.62 cm) long as shown. Coil 72 can for example extend ¼ inch (6.35 mm) past each end of susceptor 72, making the length of coil 72 about 3.5 inches (8.89 cm) total. The elongated inductive heating modules may have a tendency to heat the middle of tubes 338 more than the ends of the tubes. That is, they may tend to create a "hot spot" at the middle of the susceptor. Extending coil 72 past the susceptor controls "hot spots" and tends to equalize the heat generated along the entire length of the susceptor.

Another method for combating "hot spots" applicable to any of the elongated inductive heating modules herein is to change the pitch of the coil at the "hot spots". Coil 72 in one embodiment is wound as tightly as possible, such that no or substantially no space exists between the windings of coil 72. It is however contemplated to space the windings apart at a known susceptor "hot spot" to prevent the "hot spot". The windings can be spaced apart a fraction of the wire diameter of coil 72 or a distance more than the wire diameter. The spacing can vary or be substantially the same between windings of coil 72. The windings at cooler parts of the susceptor would remain tightly wound in one embodiment, e.g., with little or no spacing between the windings. Coil 72 having winding sections tightly wound at non-"hotspots" and spaced apart windings at "hotspots" attempts to produce even heating along the entire length of the susceptor.

It is contemplated to fix, e.g., glue or otherwise mechanically fix, coil 72 in a partially spaced apart state to jacket 450 located within the instrument. It is also contemplated to mount coil 72 within the instrument and structure the instrument with spacers to hold the windings in place at the desired spacings. It is further contemplated to provide both (i) the extension of coil 72 past one or both ends of the susceptor and (ii) the changing of the pitch of the susceptor at "hot spots" to combat the "hot spots" in an attempt to produce even heating along the susceptor length.

The primary coil is powered via the electronics 24 shown in FIG. 1 for example. Heater 420 can be powered such that the two tubes 338 of module 430 can be operated at a higher constant tubing temperature to produce a desired outlet temperature at a desired flowrate, operating power and frequency.

In the illustrated embodiment, the length and width of the flange of jacket 450 is about 1.00 inch (2.54 cm) by about 1.00 inch. The inner diameter of jacket 450 is about 0.500 inch (1.27 cm). In the illustrated embodiment, tubes 338 are about 3.00 inches long including the angled tips (7.62 cm), have about an 0.159 inch (4 mm) outside diameter and are about 0.010 inch (0.25 mm) thick. The center-to-center distance between the tubes is about 0.21 inch (5.33 mm). A nominal flux gap G1 between the inner diameter of coil 72 and the outside of tubes 338 is about 0.126 inch (3.2 mm). A largest flux gap G2 between the inner diameter of coil 72 and the outside of tubes 338 is about 0.231 inch (5.9 mm). A height y1 of manifold 440 is about 0.500 inch (1.27 cm). An adhesive well or crease y2 extends down about 0.200 inch (5.1 mm) between the top of manifold 440 and the outside of tubes 338 to allow adhesive to seep between the manifold and tubes. The well also extends between tubes 338.

A fluid heating heater very similar to heater 420 was tested using the electronic circuits from a customized Ameritherm Hot Shot™ power supply. The primary coil 72 used was wound 13.5 turns in a helical manner around the housing of the heating module, such that the axis of the helical coil was at least substantially parallel to the length of tubes. Coil 72 was 1050 strands of 42 AWG Litz wire. With water passing through the disposable at a rate of about 250 ml/min, the heating module heated the water from 9.8° C. to 34.2° C., which indicates that the heating module inputs power into the water at about 363 Watts. The AC mains inputs power into the hot plate primary at about 416 Watts. This indicates an efficiency of about 87%.

Heater 420 is efficient from a magnetic and thermal standpoint. Metal tubes 338 can be made relatively inexpensively and the overall part count is minimal. Again, module 430 can have relatively thin tube walls, making the heating module 430 more responsive. The thin walls do not store as much energy, making the module better able to cope with a fluid flow stoppage. Module 430 could be changed to a single tube which is bent into a U-shape eliminating the need for reversing manifold 440.

FIGS. 28H to 28K illustrate an alternative fluid heating module 430 operable with fluid heater 420, including all alternatives. Fluid heating module 430 of FIGS. 28H to 28K can have similar dimensions and the same materials as that of FIGS. 28A to 28G. Fluid heating module 430 of FIGS. 28H to 28K also includes similar end caps 432 and 440 as those of fluid heating module 430 of FIGS. 28A to 28G, including right angle inlet 436 and outlet 438. Fluid heating module 430 of FIGS. 28H to 28K can also operate with insulating jacket 450 and coil 72 as described above with module 430 of FIGS. 28A to 28G.

The primary difference between the two heating modules is that fluid heating module 430 of FIGS. 28H to 28K includes a single rectangular susceptor tube 338 that is divided into tube sections 338a and 338b, e.g., square or rectangular sections. FIGS. 28I to 28K each show a common wall or divider wall 452 separating sections 338a and 338b of tube 338. Such configuration improves manufacturability and module rigidity, minimizes module width and potentially improves overall cost. In the illustrated embodiment tube section 338a is an inlet tube section communicating with inlet 436, while tube section 338b is an outlet tube section communicating with outlet 438. It is contemplated to replace adjacent tubes of modules 360 and 400 shown above with a single rectangular susceptor tube 338 that is divided into tube sections 338a and 338b. Further alternatively any of modules 360, 400 and 430 can be made with separate square tubes.

Figure 28L:
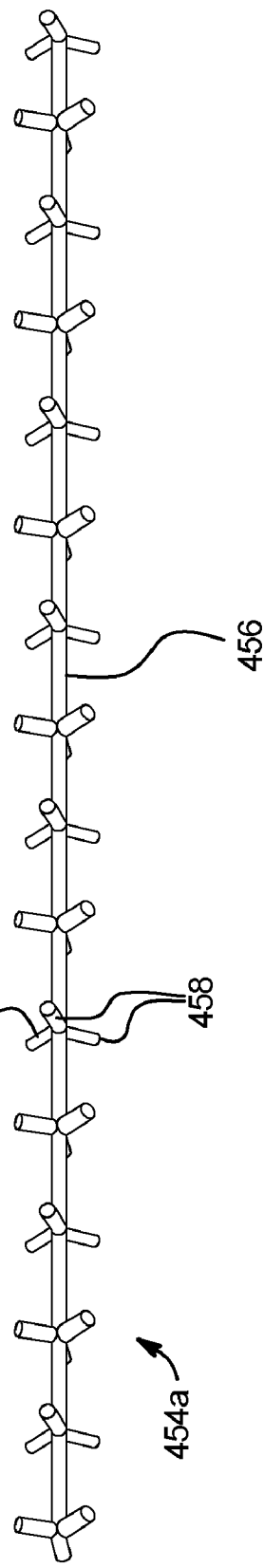
FIGS. 28L and 28M are perspective and side views of one embodiment of a static mixer used in any of the tube fluid heating modules described herein.
Figure 28M:
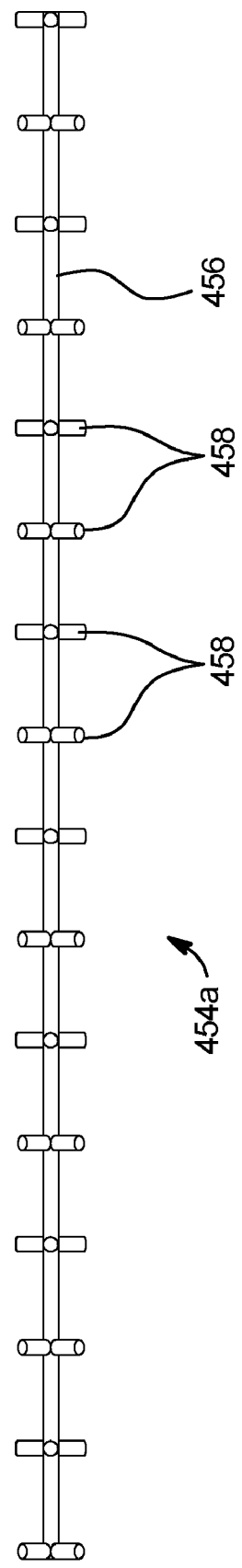

FIGS. 28L and 28M illustrate a first static mixer 454a suitable for insertion into any of the tube heating modules described herein. The illustrated static mixer 454a is sized for a three inch (7.62 cm) tube but can be sized differently for a differently sized tube. The dimensions shown are for example only but do point to various suitable spacings and orientations. In one embodiment, each tube of the heating module is fitted with a mixer, e.g., mixer 454a. Alternatively, less than all tubes are fitted with static mixers.

Mixer 454a can be plastic or metal, e.g., stainless steel. The mixer makes fluid flow more turbulent and causes the fluid to mix and heat more evenly without creating an undue pressure drop. Mixer 454a in the illustrated embodiment includes a rounded stem 456 and extending pegs 458 for smooth contact with the fluid. Alternatively, stem 456 and pegs 458 can be flat and oriented generally perpendicular to fluid flow or at an angle to same.

Mixer 454a includes three pegs 458 at each peg set extending radially and equidistantly at about 120°. More or less pegs 458 can be provided per peg set and extend equidistantly or non-equidistantly as desired. Different peg sets can have different peg configurations, e.g., number and spacing of pegs. Pegs 458 in one embodiment extend to touch or come very close to the inner wall of the tube into which mixer 454a is inserted. The three pegs 458 are oriented differently on stem 456 than the next set of pegs in certain cases (e.g., at the middle) for illustrated mixer 458a. The three pegs 458 are oriented the same on stem 456 as the next set of pegs in other cases (e.g., at the end) for illustrated mixer 458a. Alternatively, the three pegs 458 are oriented the same or differently on stem 456 as the next set of pegs in all cases.

Mixer 454a shows sets of pegs 458 spaced equally along stem 456 (e.g., at 0.177 inch (4.5 mm)). Mixer 454b shows sets of pegs 458 spaced at a larger distance along stem 456 (e.g., at 0.354 inch (9.0 mm)) at the ends of stem 456 and at a shorter distance along stem (e.g., at 0.177 inch (4.5 mm)) at the middle of stem 456. Mixer 454c also bunches peg sets at the middle and shows sets of pegs 458 spaced at a larger distance along stem 456 (e.g., at 0.472 inch (12.0 mm)) at the ends of stem 456 and at an even shorter distance along stem (e.g., at 0.118 inch (3.0 mm)) at the middle of stem 456. Mixer 454c also includes two different spacing step-downs per side of stem 456, while mixer 454b shows one spacing step-down per side of stem 456.

Bunching the peg sets at the middle of stem 456 (and orientating the sets differently from the next set) tends to mix and even the temperature of the fluid more so at the middle of the susceptor where it may be needed the most due to a "hot spot" residing generally at the middle of the susceptor. The spacing dimensions are again merely for example. It should be appreciated that the number, spacing, radial orientation, orientation with respect to next peg set, shape and size of the pegs and peg sets can each be modified optimized to produce a desired mixing and pressure drop outcome.

In an alternative embodiment, a plastic or metal spring is inserted into the tubes as a static mixer. The spring can be a known compression spring, which is sized such that the outside diameter of the spring is the same or slightly less than the inside diameter of the tube into which the spring is inserted. The spring (or multiple springs) can run at least substantially the entire length of the tube. The spring mixer is advantageous because its windings tend to push the fluid inwardly from the wall of the tube where the fluid tends to be heated more than at the middle of the tube. The spring also promotes fluid mixing and for both reasons provides a more evenly heated fluid. The spring is also economical and likely to be found as an off-the-shelf component. The diameter of the spring coil and the number coil pitch are selected to optimize even fluid heating and pressure drop.

Mixing of the fluid as it is being heated is discussed herein elsewhere, e.g., via bumps or inconsistencies in the baffles, added stainless steel wool or beads, sintering, etc. Thus, it is contemplated to add a mixing element in any of the baffle, cylinder, tube, cassette, pouch or bag heating modules discussed herein.

Twisted Baffle

Referring now to FIGS. 29A to 29E, fluid heating module for 460 illustrates a further alternate secondary coil or susceptor, which includes a capped metal tube 470. Module 460 includes an inlet/outlet manifold 462, having a dialysis fluid inlet 464 and a dialysis fluid outlet 466. Dialysis fluid inlet 464 and dialysis fluid outlet 466 can: (i) be any suitable medical tube or port connector, such as a luer connector, or a hose barb connector; (ii) connect heating module 460 directly to a disposable pumping and/or valving cassette for example; or (iii) alternatively connect heating module 460 to another part of a disposable set, such as one for peritoneal dialysis or hemodialysis, via inline with a supply line or a patient line. In the illustrated embodiment, inlet 464 and outlet 466 are oriented in a generally inline manner with that of a twisted susceptor 480. In an alternative embodiment, inlet 464 and outlet 466 are placed in a right angle relationship with the axis of susceptor 470.

Manifold 462 is connected to conductive susceptor 470 mechanically, via an adhesive and/or via an adhesive bond. Susceptor 470 includes a generally semispherical end 472, which provides a suitable shape for the dialysis fluid to change direction one hundred eighty degrees as the fluid reaches the bottom end 482 of a twisted baffle 480.

Manifold 462 can be made of any of the insulating materials described herein. Susceptor 470 likewise can be made of stainless steel, e.g., magnetically susceptible stainless steel 430, or nonmagnetic stainless steel 304 or 316. Twisted baffle 480 can be plastic.

Manifold 462 mechanically and/or adhesively holds baffle 480 at the top 484 of the baffle. To that end, manifold 462 can provide a lip or other type of crimping structure, which accepts top 484 of baffle 480 and mechanically clamps top 484 and/or enables top 484 to be adhesively bonded to crimping structure 468.

As seen best in FIG. 29E, dialysis fluid flows into fluid heating module 460 via inlet 464. Dialysis fluid flows generally along a first face 486a of baffle 480, around end 482 of baffle 480, along a second twisting surface 486b of baffle 480 and out fluid heating module 460 via outlet 466. Twisted baffle 480 is illustrated as having generally two turns, although a single turn or more than two turns can be provided.

In one implementation, a total length L1, of fluid heating module 460 is about 4.361 inches (11.1 cm). A length L2 of manifold 462 is about 0.96 inch (2.44 cm). An outer diameter of housing 470 is about 0.281 inch (0.714 cm). Inlet 464 and outlet 466 are spaced apart center-to-center by about 0.300 inch (7.62 mm).

As discussed above, housing 470 in one embodiment is a metal susceptor, such as stainless steel, and the dialysis instrument includes an insulating jacket, such as jacket 450 shown above in connection with heater 420. Coil 72 is wrapped around the jacket in the manner shown with heater 420. Stainless steel housing 470 is then slid snuggly into jacket 450. Here, the outer surface of stainless steel housing 470 is moved closer to coil 72 due to elimination of bottom manifold, e.g., reducing the flux gap.

In an alternative embodiment, susceptor 470 is a straight tube with an end cap fitted to the bottom 472 of housing 470. The alternative end cap can be adhesively bonded or suitably fixed mechanically and/or adhesively to housing 470.

In a further alternative embodiment, housing 470 is made of an insulating material. Coil 72 of the dialysis instrument is wound such that plastic housing 470 fits snuggly within the coil. Here, twisted baffle 480 forms the conductive susceptor. Susceptor baffle 480 can be roughened or sintered or include turbulating bumps or be sintered as has been described herein. Susceptor baffle 480 can alternatively be replaced with a stainless steel mesh or wool material.

Shim Module

Referring now to FIGS. 30A to 30F, heating module 490 illustrates yet another type of susceptor or inductive fluid heater, which here includes an inner and outer cylindrical rink-like housing 492, holding a pair of conductive washers or shims 500a and 500b. Housing 492 in an embodiment is made of an insulating material such as any insulating material described herein. Conductive shims or washers 500 (referring collectively to washers 500a and 500b) are made of a conductive material such as magnetically susceptible or nonmagnetic stainless steel as has been described herein.

FIG. 30F shows housing 492 having in an inner ring 494 and an outer ring 496 which can both be bowed slightly away from a flow path between the rings if desired. FIG. 30F illustrates that turbulating baffles 498a to 498h are placed equidistantly about a circumference of housing 492. Baffles 498 (referring collectively to baffles 498a to baffles 498h) can be oriented in a same or different pitch relative to a horizontal plain through both inner ring 494 and outer ring 496. In the illustrated embodiment, the pitch of baffles 498 is alternated to cause fluid to flow up and down about the baffles, increasing contact with the metallic inner surfaces of washers 500.

Outer ring 496 includes a dialysis fluid inlet 502 and a dialysis fluid outlet 504 spaced closely to dialysis fluid inlet 502. Detail XXXD shown in FIG. 30D illustrates that each of inlet 502 and outlet 504 include an inner tubing port 506b and an outer collar 506a which reinforce a connection between a tube placed over inner port 506b, as discussed in detail below.

As seen in FIG. 30F, dialysis fluid flows into housing 492 through inlet 502 and is channeled either under or over baffle 498a, then alternating over or under baffles 498b, 498c, and 498d, and so on until reaching outlet 504. In an embodiment, a hard stop is provided instead of baffle 498h such that dialysis fluid is forced out outlet 504 after one turn around housing 492. Alternatively, a portion of dialysis fluid can potentially circulate around housing 492 more than once before leaving through outlet 504.

It is contemplated to provide a volume between washers 500 that is greater than the volume of the tubing inlet port to slow fluid velocity and to increase resident heating time of the dialysis fluid within the chamber of housing 492. Baffles 498 tend to disrupt laminar flow and create turbulence so as to improve contact between the net fluid volume and the heated surfaces of washers 500a and 500b. The contacting surfaces of washers 500 can be roughened, e.g., bead blasted, to improve surface contact.

Reinforcing collars 506a reduce the moment arm that a tube placed over port 506b would have if bent relative to heating module 490. This feature improves the robustness of module 490.

The primary coil operating with susceptor plates 500 of heating module 490 can be pancake-type coils, such as coil 42 shown above in FIGS. 4, 6 and 9. Pancake coil 42 can be placed adjacent to upper and/or lower washer 500a and 500b. Alternatively, heating module 490 is placed within an insulating jacket that is wound with a wire coil 72 as has been shown and described herein. Here, the jacket is sized to be slightly wider than the width of rings 494 and 496, such that a flux gap between the windings and the flat washer surfaces is suitably small. In one preferred embodiment, the primary coil is a cylindrical coil, for example, similar to the one of FIG. 7, which can fit inside inner ring 494. In an embodiment, the primary coil touches inner ring 494. Alternatively, a small gap resides between the primary coil and inner ring 494.

In one implementation, the inner diameter of inner ring 494 is about 1.38 inches (3.5 cm). The outer diameter of outer ring 496 is about 2.245 inches (5.70 cm). The height h of inner ring 494 and outer ring 496 is about 0.360 inch (9.14 mm). The outer diameter of tubing port 506b is about 0.12 inch (3.05 mm). A center to center distance between inlet 502 and outlet 504 is about 0.50 inch (1.27 cm). Washers 500a and 500b in one implementation have about a 2.125 inch (5.40 cm) outside diameter, and about a 1.5 inch (3.81 cm) inside diameter and are about 0.025 inch (0.635 mm) thick.

Saddlebag

Figure 31A:
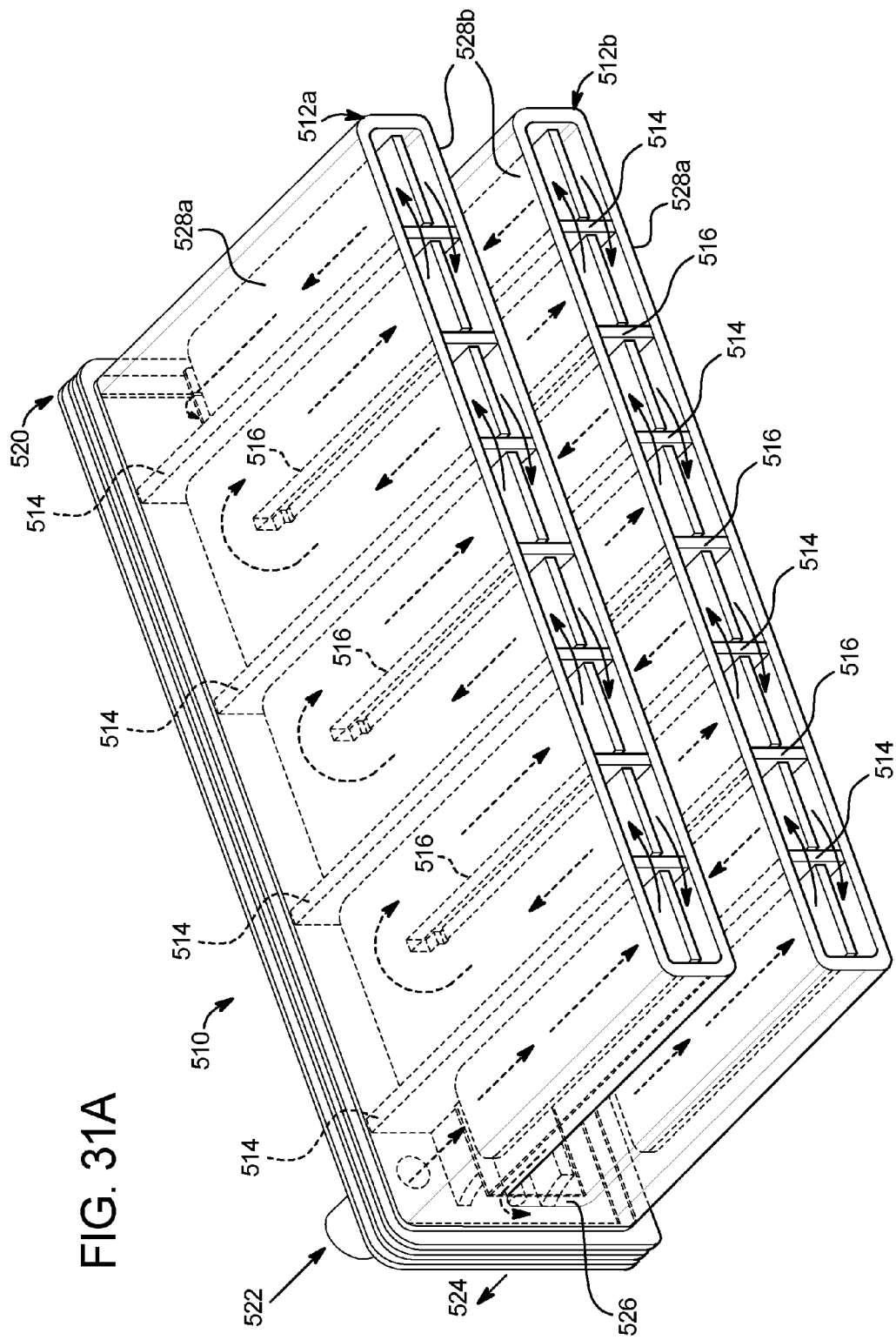
FIG. 31A is a sectioned perspective view of one embodiment of a dual chamber fluid heating module.
Figure 31B:
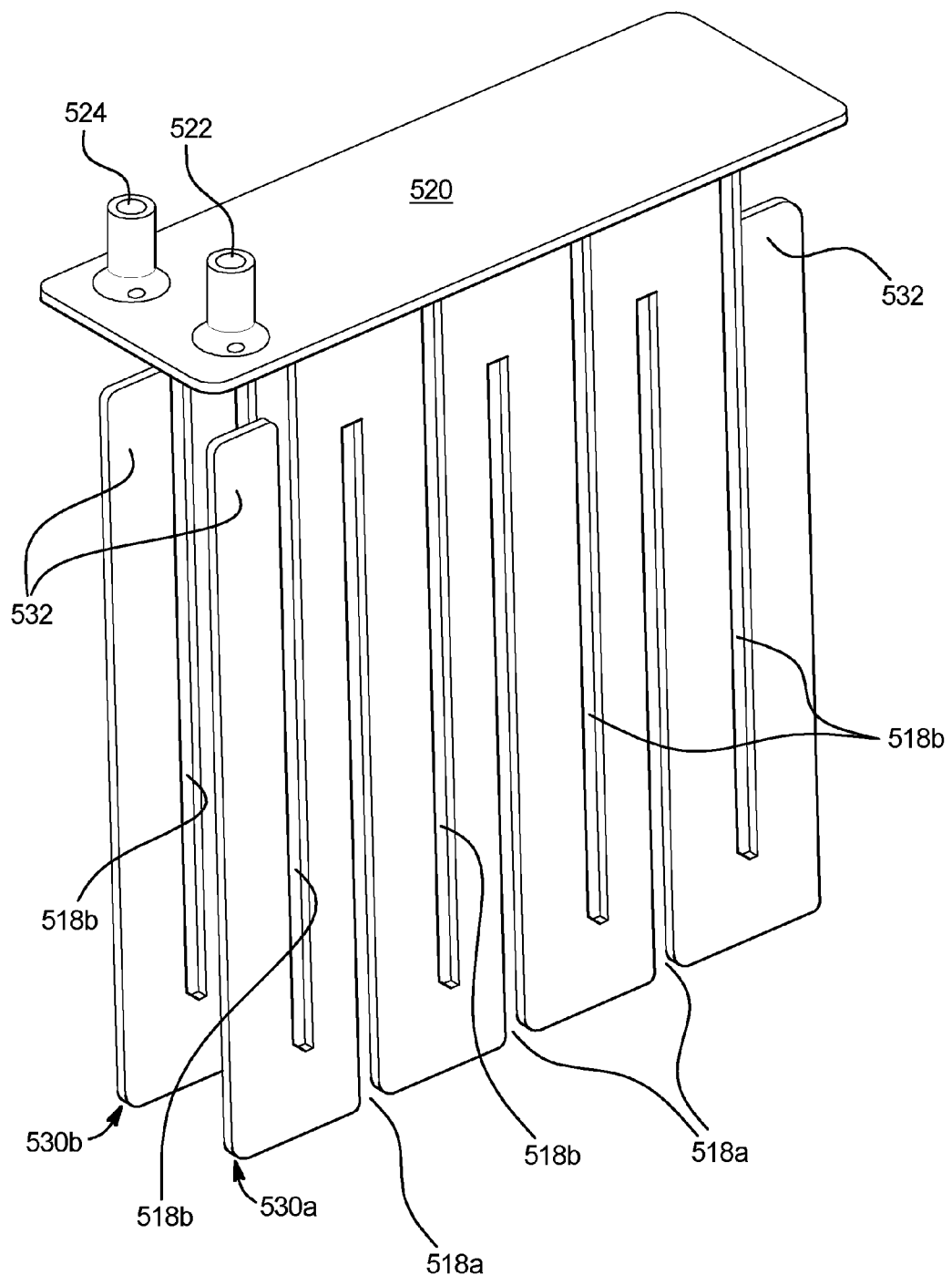
FIG. 31B is a perspective views of one embodiment of a susceptor for the dual chamber fluid heating module of FIG. 31A.

Referring now to FIGS. 31A and 31B, fluid heating module 510 illustrates a further alternative having a saddlebag or two chamber housing. Fluid heating module 510 includes a first housing 512a and a second housing 512b, which are connected at their top ends via a bridge 526. Each chamber 512a and 512b includes an outer wall 528a and an inner wall 528b, separated by longer insulating baffles 514 and shorter insulating baffles 516. Although not shown in FIG. 31A, chambers 512a and 512b are enclosed on the bottom (bottom not shown to better illustrate flow pattern). Longer insulating baffles 514 end at the bottom of susceptors 530a and 530b, such that dialysis fluid can travel under the lower edge of the longer insulating baffles 514 as seen by the arrows in FIG. 31A. Shorter insulating baffles 516 on the other hand extend to the bottom of chambers 512a and 512b such that they force dialysis fluid up towards the top of shorter baffles 516 as seen by the arrows in FIG. 31A.

Longer insulating baffles 514 and shorter insulating baffles 516 separate each chamber 512a and 512b into eight compartments as generally shown by the flow arrows in FIG. 31A. Metal susceptor 530a is inserted into chamber 512a to further separate the eight compartments into sixteen subchambers. Likewise, metal susceptor 530b is inserted into chamber 512b to separate the eight compartments into sixteen different subchambers. Thus, when chambers 512a and 512b are connected via bridge 526, fluid module 510 includes thirty-two separate subchambers. Dialysis fluid flows in series through the thirty-two chambers as indicated via the arrows.

As seen in FIG. 31B, in one embodiment a susceptor plate 530a is inserted into chamber 512a such that grooves 518a in plate 530a opening at the lower end of the plate fit over shorter insulating baffles 516 in chamber 512a. Next, longer insulating baffles 514 are slid downwardly into the slots 518b in plate 530a that open at the upper end of plate 530a. The same procedure is followed for chamber 512b and plate 530b in which plate 530b likewise includes grooves 518a and 518b. Outer conductive baffles 532 of plates 530a and 530b are shortened as illustrated to allow fluid flow to travel over the upper ends of outer baffles 532 and underneath a cap 520, which is adhesively bonded, ultrasonically welded and/or snap-fitted to chambers 512a, 512b and bridge 526.

Susceptor plates 530a and 530b can be made of stainless steel, such as magnetically susceptible or nonmagnetic stainless steel. The primary coil operating with susceptors 530a and 530b in an embodiment is a pancake coil slid between chambers 512a and 512b. The coils can be placed on the outside portions of chambers 512a and 512b, alternatively or additionally. Further alternatively, the chambers are wound with a Litz wire type coil 72. The coil in any case is part of the instrument in one embodiment.

Heating Module Integrated in Pumping Cassette

Referring now to FIG. 32, fluid heating module 540 illustrates one possible module for incorporation into a disposable dialysis fluid pumping cassette 550. Disposable pumping cassette 550 in the illustrated embodiment includes a rigid structure 552 which is sealed on first and second sides via first and second flexible membranes (not illustrated). Rigid structure 552 can be made of polycarbonate, polysulfone, urethane or potentially other high temperature plastics. Rigid structure 552 includes first and second pumping chambers 554a and 554b that operate with pneumatic pumping actuators located in the dialysis instruments (not illustrated) into which cassette 550 and integrated fluid heating module 540 are inserted. It should be appreciated that while pneumatic pump actuators can be used in one embodiment, the pumping of the system employing integrated fluid heating module 540 is not limited to pneumatic pumping and can instead be peristaltic pumping or mechanically activated membrane pumping.

Rigid structure 552 also includes a plurality of valve ports 556a to 556j (referred to herein collectively as valve ports 556 or generally, individually as valve port 556). A flexible membrane seals around the edge of rigid structure 552 and also to the ridges extending from a base wall 559 of the structure defining pump chambers 554 (referring collectively to pump chambers 554a and 554b) and valve ports 556. A description of the operation of the flexible membrane in combination with pump ports 554 and valve ports 556 is described in connection with U.S. Pat. No. 4,826,482, the pertinent portions of which are incorporated herein expressly by reference.

Valve ports 556 lead to flow paths located on the opposite side of base wall 559 of rigid structure 552. Cassette 550 also includes a plurality of tubing ports 558a to 558g (referred herein collectively as ports 558 or generally, individually as port 558). Ports 558 connect to tubes, which run to supply bags, and potentially to or from the patient. One preferred port 560 is discussed in detail below. Heating module 540 also includes a plurality of baffle plates 562a to 562i (referred herein to collectively as baffle plates 562 and generally, individually as baffle plate 562).

In one embodiment, heater module 540 is heated resistively. Here, baffle plates 562 are part of and made with cassette 550 and are electrically insulating. A heating plate 568 extends from the outside of cassette 550, through the outer wall of rigid structure 552 of cassette 550 and through each of the baffles 562. Ends 568a and 568b of heating plate 568 can be connected operably to resistive heater supply contacts (not illustrated) or directly to a current source.

Insulating baffles force fluid back and forth over heating plate 568. The baffle plates 562 are staggered as illustrated to create a winding flow path as shown generally by the arrows in FIG. 32. Base wall 559 does not extend into the heating path area of baffles 562 in one embodiment. Alternatively, wall 559 is provided and baffles 562 extend through to the unseen side of rigid housing 552. A hole in wall 559 enables the fluid to flow in the heating pathway on each side of wall 559.

In an alternative resistive embodiment, baffle plates 562 are conductive, e.g., made of stainless steel such as nonmagnetic stainless steel 304 or 316 or magnetically susceptible stainless steel 430. Baffles 562 can be roughened or sintered so as to disrupt fluid flow, making it more turbulent. Rigid structure 552 can hold conductive baffles 562 mechanically and/or via an adhesive bond. As above, plate 559 is not needed in the heating area. Alternatively, plate 559 can be metal and formed with baffles 562. Further alternatively, plate 559 is made of an insulating material. Here, baffles 562 can extend through plate 559 or be provided as separate sets of baffles on both sides of plate 559.

In the alternative resistive embodiment, plates 564 and 566 formed on the outside of baffles 562 are also made of a conductive material, e.g., that of baffles 562, so as to provide an electrical path from plates 568a and 568b. Here, plate 568 does not extend all the way across cassette 550 and baffles 562 but is instead separated into two plates 568a and 568b, as shown, which end at outer plates 564 and 566, respectively. Plates 564 and 566 communicate electrically with baffles 562.

In a further alternative embodiment, fluid heating module 540 is heated inductively via one pancake coil or dual pancake coils residing on one or two sides of cassette 550 when the cassette is loaded into the dialysis instrument. Or, cassette 550 can slide inside of a wound coil 72 described herein, which resides within the dialysis instrument. Cassette 550 when loaded into the instrument is slid into coil 72, such that fluid heating module 540 comes into alignment with coil 72. In this inductive embodiment, rigid walls 564 and 566 formed on the outside of baffle 552 can be made of a plastic or other insulating material along with the remainder of rigid housing 552.

In the inductive embodiment, baffle plates 562 are also conductive and form the susceptor. Here, plates 562 can be made of stainless steel, such as nonmagnetic stainless steel 304 or 316, or magnetically susceptible stainless steel 430. Baffles 562 can be roughened or sintered so as to disrupt fluid flow, making it more turbulent. Rigid structure 552 can hold conductive baffles 562 mechanically and/or via an adhesive bond. In the inductive heating embodiment, plate 568 or plates 568a and 568b described above are not needed. All alternatives for not providing plate 559 or providing plate 559 for the resistive embodiment in which baffles 562 are conductive are also applicable here.

Each of the alternative integral cassette fluid heating modules is shown below using inductive heating. It should be appreciated, however, that similar to heating module 540, the alternative modules can alternatively be made to operate resistively instead of inductively.

Figure 33:
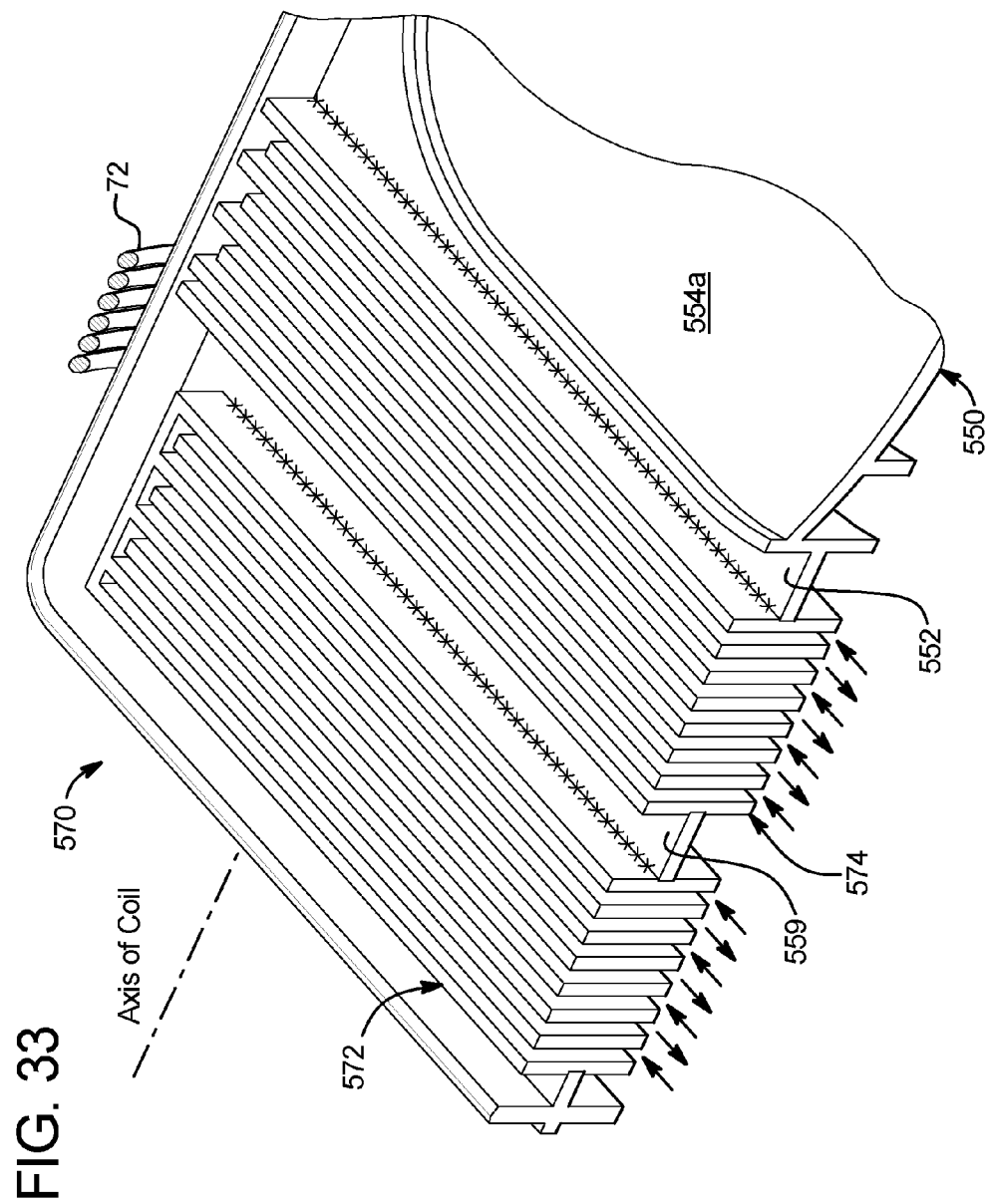
FIG. 33 is a sectioned perspective view of another embodiment of a fluid heating module integrated into a disposable pumping cassette.

Referring now to FIG. 33, an alternative integral cassette fluid heating module 570 is illustrated. Module 570 operates with disposable cassette 550, which includes each of the components described above. Alternative fluid heating module 570 includes a pair of baffle compartments 572 and 574, which extend through base wall 559 of rigid structure 552 of cassette 550. Baffle compartments 572 and 574 each include a plurality of staggered baffles, which can be of any of the materials discussed above for baffles 562. Baffle compartments 572 and 574 in an embodiment are adhesively bonded at the areas marked X in FIG. 33 to the base wall 559 of cassette 550.

With both heating modules 540 and 570, a flexible membrane welded to rigid plastic structure 552 can be bonded to baffles 562 of module 540 or the baffles of compartments 572 and 574 or module 570. Alternatively, a rigid plastic top and bottom are sealed to the plastic film, which in turn is adhesively bonded to the conductive baffles. Further alternatively, a plastic top and bottom are snap-fitted to the baffles. The top and bottom are then welded or bonded to the flexible sheeting. Still further alternatively, the conductive baffles include conductive tops and bottoms, creating an enclosed conductive shell, which is adhesively bonded to rigid portion 552 of cassette 550. Here, because the conductive heating baffle portion is enclosed, the portion does not have to be sealed to the cassette sheeting.

Heating module 570 is shown in operable communication with a wound primary coil 72. Here, the baffles of compartments 572 and 574 operate as susceptors. As described above, however, baffle compartments 572 and 574 can be modified to operate in a resistive heating mode.

Figure 34:
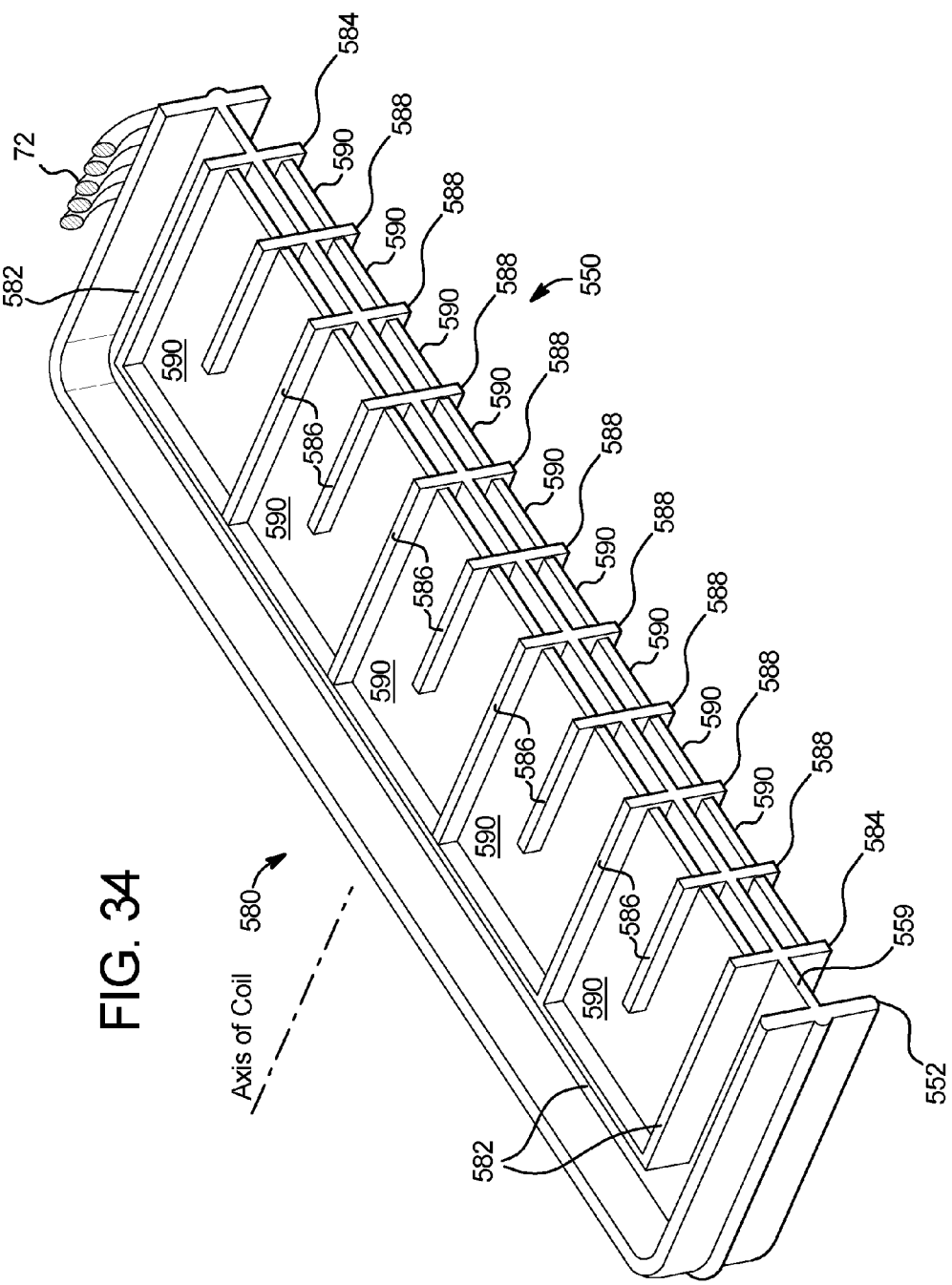
FIG. 34 is a sectioned perspective view of a further embodiment of a fluid heating module integrated into a disposable pumping cassette.

Referring now to integrated fluid heating module 580 of FIG. 34, a further alternative integrated cassette-based heating module is illustrated. Heater module 580 is operable with a disposable cassette 550 as described herein. For convenience, a cut-away section of heater module 580 is illustrated.

In heating module 580, rigid structure 552 is molded to include an upper insulating sidewall 582 and an aligned lower extending sidewall 584. Rigid portion 552 is further molded to include upper insulating baffle plates 586 and aligned lower insulating baffle plates 588. Conductive inserts 590, made of any of the medically safe conductive materials discussed herein, are snap-fitted and/or adhesively bonded to side walls 582 and 584 and insulation baffles plates 586 and 588.

Base wall 559 includes an aperture (not shown), which allows fluid after winding through a set of baffles on one side of base wall 559 to flow through the aperture to the other side of base wall 559 and wind through the second set of conductive baffles. It should be appreciated that flow in fluid heating module 580 is very similar to that of the saddle bag fluid heating module 510 discussed above in connection with FIGS. 31A and 31B.

In an embodiment, upper and lower flexible sheets are adhesively bonded or welded to the ridges of insulating side walls 582 and 584 and insulating baffles 586 and 588 to form an enclosed fluid pathway on both sides of cassette 550. Induction coil 72 is shown in operable relationship with conductive baffles 590, which operate as a secondary coil or susceptor to primary coil 72. Alternatively, baffles 590 are extended outside of cassette 550 for resistive heater operation.

Figure 35:
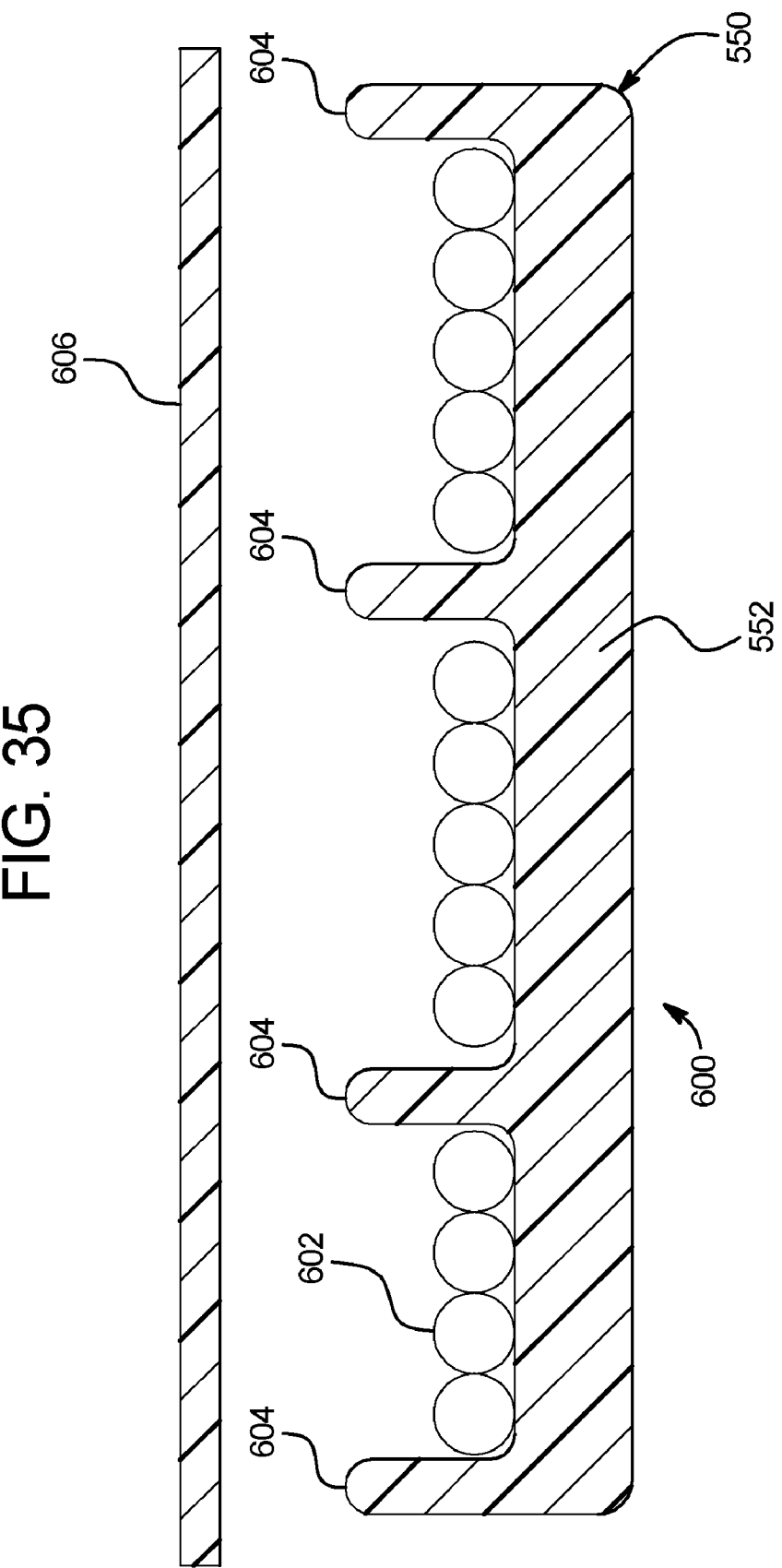
FIG. 35 is a sectioned elevation view of an embodiment of a fluid heating module having stainless steel balls captured in a fluid heating pathway, e.g., the pathway of a disposable pumping cassette.

Referring now to FIG. 35, heating module 600 illustrates a further alternative integrated cassette embodiment. Here, stainless steel, magnetically susceptible or nonmagnetic, balls or pellets 602 fill heating pathways defined by insulating baffle plates 604. Insulating baffles 604 in an embodiment form serpentine channels. Insulating baffle plates 604 are bonded or welded to a flexible sheet 606 of cassette 550. Heating module 600 in one embodiment is heated via inductive heating using one or more pancake 42 or a wound coil 72, e.g., wound to form an axis either parallel to or perpendicular to baffles 604. Stainless steel balls 602 help to disrupt dialysis fluid flow, so as to make it more turbulent. Stainless steel balls 602 are alternatively replaced with a stainless steel mesh wool.

Figure 36:
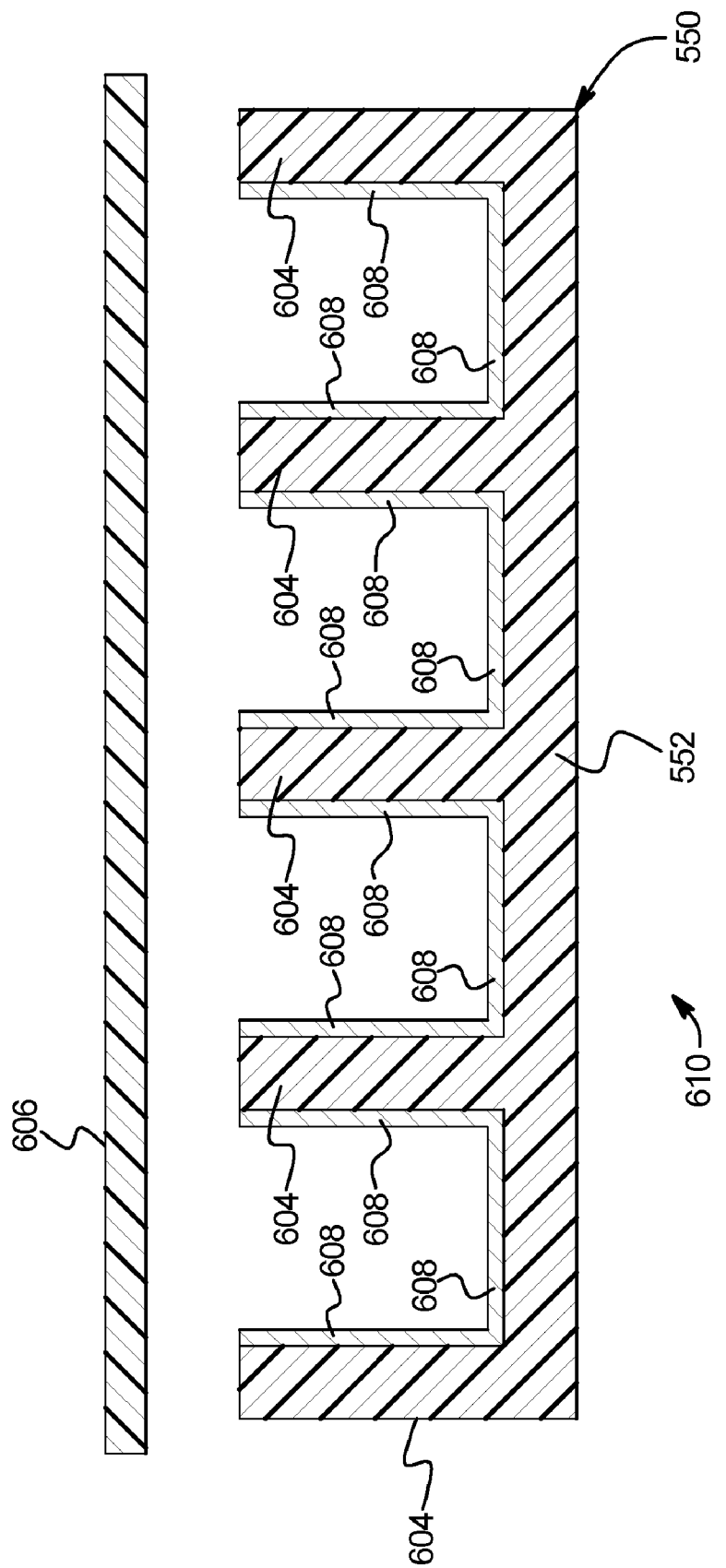
FIG. 36 is a sectioned elevation view of an embodiment of a fluid heating module having stainless steel electro-deposited onto a fluid heating pathway, e.g., the pathway of a disposable pumping cassette.

Referring now to FIG. 36, fluid heating module 610 illustrates another possible integrated cassette type fluid heating module. As with module 600, module 610 includes a rigid plastic structure 552 of disposable pumping cassette 550. Rigid plastic portion 552 defines a plurality of insulating baffles 604. Baffles 604, in an embodiment, define a serpentine path as has been described herein. The tops of baffles 604 are ultrasonically welded or adhesively bonded to cassette sheeting 606.

With module 610, a layer 608 of metal or metal ink is deposited electrolessly, e.g., via a spray technique, an ink jetting technique or a photo-imaging process, onto the sides of baffles 604 and the bottom of channels defined by baffles 604. The metal layer 608 can be applied in multiple applications and cured in multiple steps to build layer 608 to a desired thickness. In an embodiment, metal layer 608 is a stainless steel layer. Heating module 610 operates inductively with a conductive coil in one embodiment, e.g., via one or more pancake coil 42 or helical coil 72.

In an alternative embodiment, conductive layer 608 is not provided. Instead, at least the heating module portion 610 of rigid portion 552 of pumping cassette 550, including insulating baffles 604 is formed from an injection molded part filled with metal powder or carbon. This modified part becomes heated upon the powering of an associated primary coil, such as one or more pancake coil 42 or wire coil 72 wound around the conductively filled heating portion 610 of the cassette.

In a further alternative embodiment, metal layer 608 is removed. Instead, at least the heating module portion 610 of disposable cassette 550 is metal and is made from a metal injection molding ("MIM") or a powdered metal ("PM") process. Metal portion 610 is made up of baffles 604 and a base connecting the baffle 604, which become heated inductively via an inductive coil. This embodiment also lends itself to resistive heating, in which the exposed metal portion 610 is placed in contact with electrical heating contacts.

Conductive portion 610 made via the MIM or PM process is connected sealingly to a rigid plastic portion 552 of disposable cassette 550 via a tight-fitting arrangement and an adhesive bond in one embodiment. A metal cover (not shown) is formed alternatively on the top of baffles 604 to provide a completely enclosed metal heating serpentine fluid path area.

In yet another alternative integrated cassette heater embodiment, twisted conductive baffles, such as baffle 480 of heating module 460 are placed between insulating baffles 604. In still a further alternative embodiment, insulating baffles 604 are removed and replaced with the twisted susceptor plates 480. Twisted susceptor plates 480 can include as many turns as desired to create a turbulent flow path. The plates 480 are provided in an amount sufficient to conduct enough current to become heated to a necessary level. Twisted baffles 480 can be crimped at one end to a side of plastic portion 552, such that the baffles 480 are held rigidly within cassette 550.

Heating Module Attached to Pumping Cassette

Referring now to FIG. 37, a disposable cassette 550a shows one possible cassette for connecting to various fluid heating modules discussed above. Cassette 550a includes rigid portion 552 defining pump chambers 554, valve chambers or valve seats 556 and tubing ports 558 as discussed above. Cassette 550a further includes a to-heater port 558h and a from-heater port 558i. Rigid portion 552 also includes a to-heater pathway 560a, which is placed in fluid communication with to-heater port 558h. Rigid portion 552 of cassette 550a further includes a from-heater passageway 560b, which is placed in fluid communication with from-heater port 558i. Flexible sheeting is applied to the front and back surfaces of cassette 558a to seal pump chambers 554, valve chambers 556 and fluid heating pathways 560a and 560b. Fluid heating pathways 560a and 560b communicate with other pathways through valves 556, for example, communicate with pathways leading to or from one of the pump chambers 554 or pathways leading to one or more of ports 558a to 558g.

Heating ports 558h and 558i enable cassette 550a to communicate with many of the fluid heating modules discussed above, such as multiple baffle plate module 150 of FIGS. 14A to 14E, three plate module 220 of FIGS. 17A to 17F, serpentine baffle module 190 of FIGS. 18A to 18C, five tube module 330 of FIGS. 25A to 25E, six tube module 360 of FIGS. 26A to 26E, two tube module 400 of FIGS. 27A to 27D and two tube module 430 of FIGS. 28A to 28G. Each of the above modules includes an inlet and outlet spaced together closely, which lends itself to ready connection to closely spaced ports 558h and 558i. Applicants do not intend to limit cassette 550a to the listed modules below. However, other modules could require longer lengths of tubing between cassette 550a and the heating module. A single port cassette for single tube module 460 of FIGS. 29A to 29E is also shown below.

In one implementation, cassette 550a has a footprint of about 5.75 inches (14.6 cm) high by about 5.25 inches (13.3 cm) wide (largest width) by about 0.50 inch (1.27 cm) thick. Cassette 550a includes two pneumatic pumping chambers 554 (although peristaltic or mechanically actuated volumetric pumping chambers could be used instead). Illustrated cassette 550a includes seventeen square pneumatic valve ports 565. Alternatively, valve ports are removed from cassette 550a and clamps are used instead.

FIG. 38 illustrates the connection of cassette 550a to a further alternative fluid heating module 620. Fluid heating module 620 includes a tube 632 bent to form closely spaced apart inlet 622 and outlet 624. As seen in FIG. 38, module 620 having closely spaced inlet and outlet tubes 622 and 624 enables short tubing splices 626a and 626b to connect (i) to-heater port 558h to inlet 622 and (ii) from-heater port 558i to outlet 624, respectively. The short run of splices 626a and 626b tends to prevent heat loss and increase overall system efficiency.

Cassette 550a includes a plurality of metallic contacts 630. Metal contacts 630 are used to sense fluid temperature upstream and downstream from module 620. One suitable metal contact is described in copending patent application, entitled, "Dialysis Fluid Measurement Method And Apparatus Using Conductive Contacts", filed Jul. 5, 2007, patent application Ser. No. 11/773,661, the entire contents of which are incorporated expressly herein by reference.

Alternatively, non-invasive temperature sensing using a non-invasive, e.g., infrared temperature sensor can be used to eliminate contacts 630 and associated electronics. Copending patent application entitled, "Dialysis System Having Non-Invasive Temperature Sensing", filed Jul. 5, 2007, patent application Ser. No. 11/773,746, the pertinent portions of which are incorporated herein expressly by reference, discloses one system and method for non-invasive temperature sensing using an infrared temperature sensor.

Module 620 in FIG. 38 includes a retainer 634 that holds the ends of tube 632 in a rigid manner. The ends of tube 632 are fed into a manifold 621, which includes inlet 622 and outlet 624. Inlet 622 and outlet 624 each have a port that fits into one end of one of the tubing splices 626a and 626b. The other end of tubing splices connects to to-heater port 558h and from-heater port 558i.

FIG. 39 illustrates module 630 in operation with an alternatively configured pumping cassette. FIG. 39 illustrates that fluid heating module 630 is a secondary coil operating with a primary helical coil 72 wound around a magnetic core 76, which includes magnetic flux directing arms 78a and 78b as discussed above for example in connection with FIGS. 7 to 9. Flux directing arms 78a and 78b of core 76 are located in the dialysis instruments in one embodiment and induce a current in module 630. As illustrated, coil 72 can be wound around directing coil arm 78b, between the arm and the tube of module 630.

Figure 41:
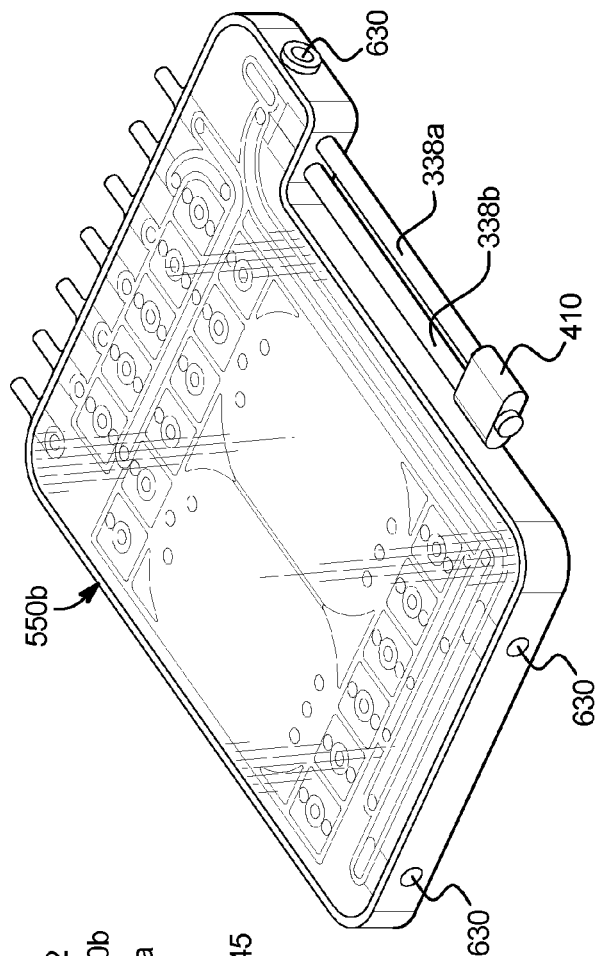
FIG. 41 is a perspective view of the disposable cassette of FIG. 40 showing a further alternative fluid heating module connected to the cassette.
Figure 40:
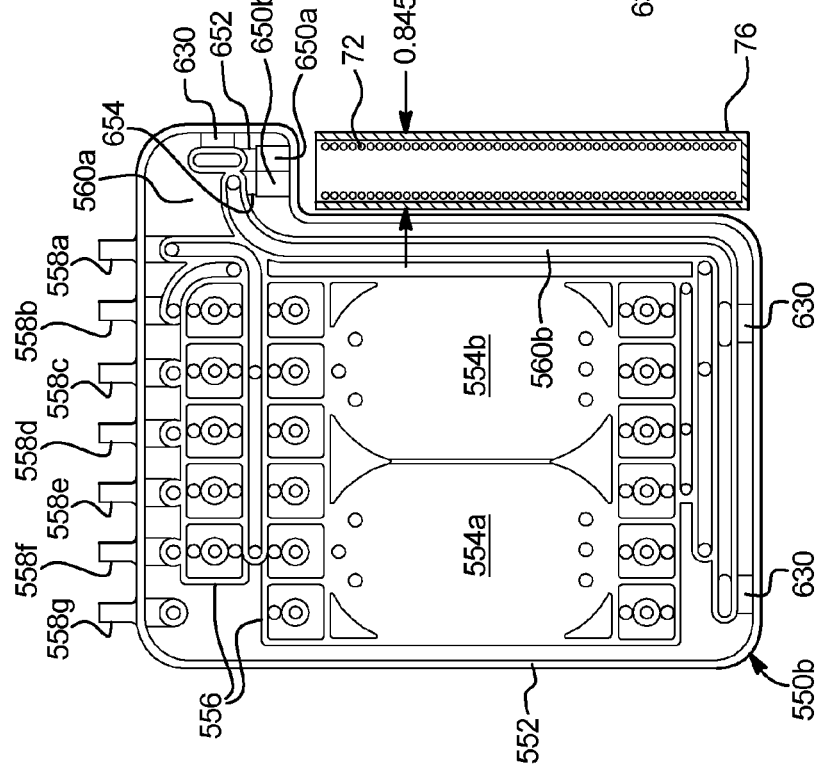
FIG. 40 is a top plan view of another embodiment of a disposable pumping cassette having embedded port connections for connecting to the fluid heating modules described herein.

Referring now to FIGS. 40 and 41, Cassette 550b illustrates an alternative pumping cassette for connecting to the fluid heating modules discussed above. Cassette 550b is largely the same as cassette 550a and also provides fluid heating pathways 560a and 560b. The primarily difference between cassette 550b and 550a is the provision of embedded/reinforcing to-heater port 650a and embedded/reinforcing from-heater port 650b (referred to herein collectively as ports 650 or generally, individually as port 650). Ports 650 are discussed in detail below in connection with FIGS. 45 to 47. To-heater port 650a communicates fluidly with to-heater fluid pathway 560a. From-heater port 650b communicates fluidly with from heater pathway 560b.

FIG. 41 illustrates that cassette 550b with embedded ports 650a and 650b enables the upper manifolds of any of the two-tube fluid heating modules discussed above (e.g., modules 360, 400 and 420) to be eliminated. Instead, the inlet tube of the two-tube heater module is connected sealingly and directly to to-heater port 650*a*, while the outlet tube of the two-tube module is connected sealingly and directly to from heater port 650*b*.

FIG. 41 illustrates one example in which upper manifold 402 is removed from fluid heating module 400 shown above in connection with FIGS. 27A to 27D. Here, tube 330*a* is mated sealingly and directly with embedded port 650*a*, while outlet tube 338*b* is mated sealingly and directly with embedded port 650*b*. Tubes 338*a* and 338*b* are connected at the bottom by a return manifold for 410. Alternatively, tubes 338*a* and 338*b* are bent from a single piece of tubing and the u-shaped tube is mated sealingly into embedded ports 650*a* and 650*b*. For example, the single bent tube 632 of fluid heating module 620 shown above in connection with FIG. 38 could be used instead of manifold 621 providing inlet and outlet ports 622 and 624. Here, manifold 621 is removed and the tubes are mounted directly into embedded ports 650*a* and 650*b*. The embedded ports enable cassette 550*b* to be slightly smaller than cassette 550*a*. For example, the largest width along the top of cassette 550*b* can be reduced to about 5.055 inches (12.8 cm).

FIG. 40 also illustrates an alternative magnetic core 76, which is made of any of the materials described herein for core 76. Core 76 illustrated here is five sided and has an open top to accept tubes 338*a* and 338*b* shown in FIG. 41. Core 76 also houses coil 72 shown in cross-section. Core 76 and coil 72 are part of the instrument and are reused. Cassette 550*b* and tubes 338*a* and 338*b* are disposed of after treatment. Core 76 may also be used with the single tube version of cassette 550*c* discussed below and with a susceptor having more than two tubes or any of the baffle plate configurations shown herein.

Magnetic core 76 can be structured in the instrument to fit around other modules discussed herein and is not limited to the tube modules. For example, a similar core 76 to that of FIG. 40 can fit around the coil 72 of any of the baffle plate modules. A core 76 can also be configured to fit around washer module 490 and canister modules 230 and 260.

Core 76 provides an additional benefit in that it tends to shield the outside world from electromagnetic interference ("EMI") that coil 72 emits. Whether provided via core 76 or additional shielding, e.g., aluminum sheeting discussed above, each of the modules discussed herein is shielded so as to meet the international guidelines for containing EMI radiation.

Referring now to FIGS. 42 and 43, a further alternative cassette 550*c* is made even smaller via the provision of a single embedded port 650*c*, which operates with a single tube fluid heating module, such as fluid heating module of 460 of FIGS. 29A to 29E. Here, inlet and outlet manifold 462 of module 460 shown above is eliminated.

Embedded port 650*c* is wider than embedded ports 650*a* and 650*b* of FIGS. 40 and 41 to accommodate a larger tube 470 that holds for example a twisted baffle 480, which splits the flow between an inlet flow running to a bottom 472 of tube 470 from the flow returning to a top end of single tube 470. Embedded port 650*c* includes an inlet pathway 652, which enables port 650*c* to communicate inlet fluid pathway 560*a*. Port 650*c* further includes an outlet pathway 654 that communicates with outlet fluid pathway 560*b* of cassette 550*c*, in contrast to port pathways 652 and 654 of FIG. 40, which are dedicated to to-heater port 650*a* and from heater port 650*b*, respectively. The provision of single tube embedded port 650*c* enables the widest width of cassette 550*c* to be reduced to about five inches (12.7 cm) in one implementation.

FIG. 44 illustrates an alternative version of the single tube fluid heating module, which here includes an end cap 474 instead of the rounded end 472 as shown in FIG. 43. End cap 474 can be plastic or metal and secured as described herein. FIG. 44 also illustrates that twisted baffle 480 can be loosely fitted into tube 470. Further, baffle 480 extends past the upper edge 476 of tube 470. The exposed edge 476 of baffle 480 extends into the well of single embedded tube port 650*c*, which enables the baffle to be held firmly in place via an abutment to inner wall 656 of port 650*c*. The configuration also directs flow from inlet pathway 652 down the inlet side of twisted baffle 480 into the well of single port 650*c*. The configuration also directs flow from the outlet side of twisted baffle 480 at edge 476 into outlet pathway 654 of cassette 550*c*.

Figure 46:
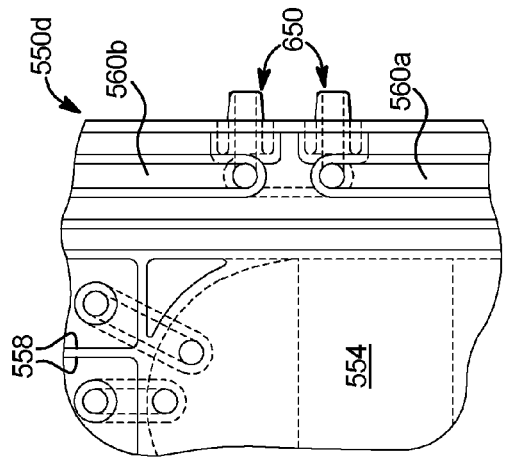
FIG. 46 is a top plan view of the embedded, reinforced ports of FIG. 45, which are spaced to be connectable, for example, to the conductive washer fluid module of FIGS. 30A to 30F.
Figure 45:
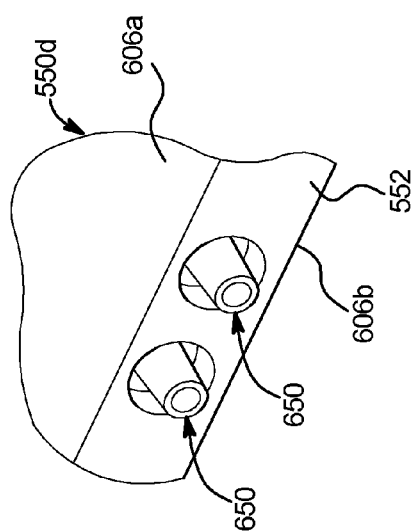
FIG. 45 is a sectioned-perspective view of embedded, reinforced fluid ports similar to ones shown in connection with FIGS. 42 to 44.
Figure 47:
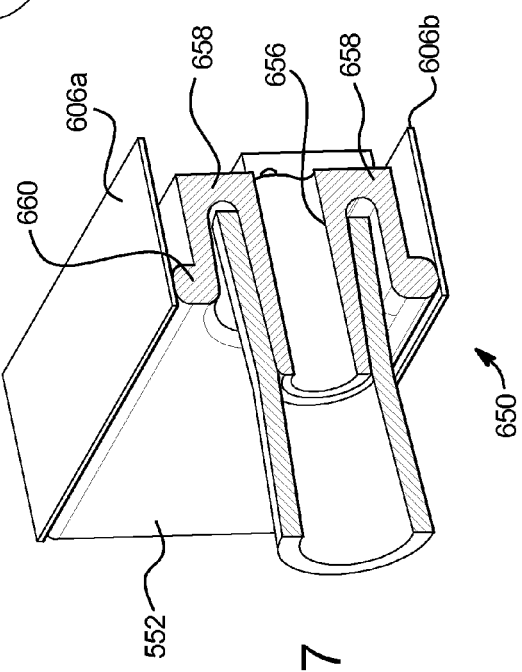
FIG. 47 is a sectioned-perspective view of one of the embedded, reinforced fluid ports of FIG. 46.

Referring now to FIGS. 45 to 47, embedded reinforced tubing ports 650 are illustrated in detail. A non-embedded reinforced port 502 is shown above in connection with FIG. 30D and dual washer fluid heater module 490. The torque and shear stress benefits associated with non-embedded reinforced port 502 are also shared by embedded reinforced port 650. It should be appreciated that the spacing of embedded ports 650 shown in FIG. 46 is appropriate for connecting dual washer module 490 to a further alternative disposable pumping cassette 550*d* shown in relevant section in FIGS. 45 and 46. Viewing heater module 490 in FIG. 30A and the cassette section of FIG. 46, nonheated fluid flows through to-heater pathway 560*a*, out a first port 650, to heater module inlet 502 (FIG. 30A), around a pathway between washers 500*a* and 500*b*, out fluid heater module outlet 504, into a second embedded port 650, which communicates fluidly from heater pathway 560*b* to an appropriate area of cassette 550*d*.

FIG. 47 illustrates that an inner port 656 is molded integrally with a sidewall 658 of rigid portion 552 of cassette 550*d*. Also, an outer retention collar 660 is molded integrally with wall 658 of rigid portion 552. Collar 660 provides the same type of reinforcing protection to tubing port 656 as does collar 506*a* to inner port 506*b* shown in connection with reinforced inlet and outlet ports 502 and 504 of FIG. 30*d*. In both cases, shear force stress on the associated inner port 656 or 506*b* is reduced because it is recessed in the cup feature or added collar 660 or 506*a*, respectively, which shifts the lever arm pivot forward. Thus someone pivoting the flexible tube in the direction shown via arrows in FIG. 47 applies a torque having a moment arm beginning at the outer dotted line in FIG. 47 as opposed to beginning at the inner dotted line shown in FIG. 47.

The space between the dotted lines indicated by a horizontal arrow shows how the moment arm and thus the torque applied onto tubing port 656 is reduced. This reduction will enhance the durability of the ports 502, 504 and 560. While the reinforced ports are shown in connection with the heating modules discussed herein, it should be appreciated that the ports can be used elsewhere on the dialysis cassettes 550, for example as supply line ports, to- or from-patient ports, or as another tubing port.

Figure 48:
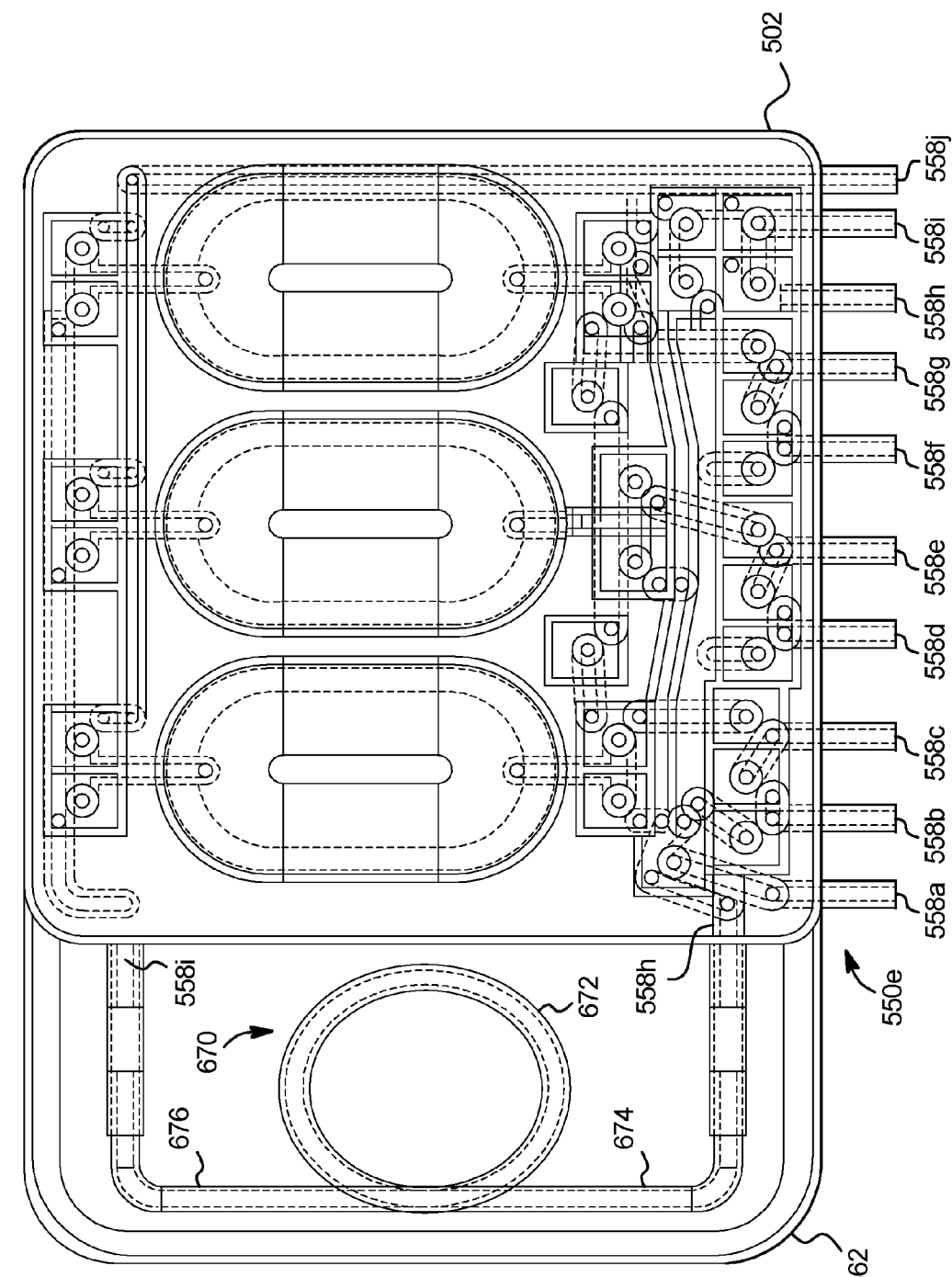
FIG. 48 is a top plan view of a further alternative embodiment of a disposable pumping cassette connected to an alternative looped tube fluid heating module.

Referring now to FIG. 48, further alternative pumping cassette 550*e* illustrates one embodiment for connecting to an inline fluid heating module, such as module 180 of FIGS. 15A to 15E, module 210 of FIGS. 16A to 16E, and the further alternative fluid heating module 670 shown in FIG. 48. Cassette 550*e* includes a to-heater port 558*h* spaced apart from a from-heater port 558*i* a distance sufficient to enable one of the inline fluid heating modules to be placed between ports 558*h* and 558*i*. It should be appreciated that the ports can alternatively be of the embedded and/or reinforced type discussed above.

Fluid heating module 670 includes a tube 672 coiled once and including an inlet end 674 and an outlet end 676 for connecting to ports 558*h* and 558*i*, respectively. The loop of tube 672 fits over a flux directing extension 78 of a magnetic core 76 as shown for example in FIG. 39. Tubing 672, like tubing 632 of fluid heating module 630, is stainless steel, such as a magnetic or nonmagnetic stainless steel, in one embodiment. Rigid portion 552 of cassette 550*e* is extended to provide a handle 662 that extends around fluid heating module 670 to help load cassette 550*e* in relation to pump and valve actuators and the fluid heating module 670 in relation to a coil 76 operating with inductive fluid heating module 670.

Spheres in a Bag

Figure 49:
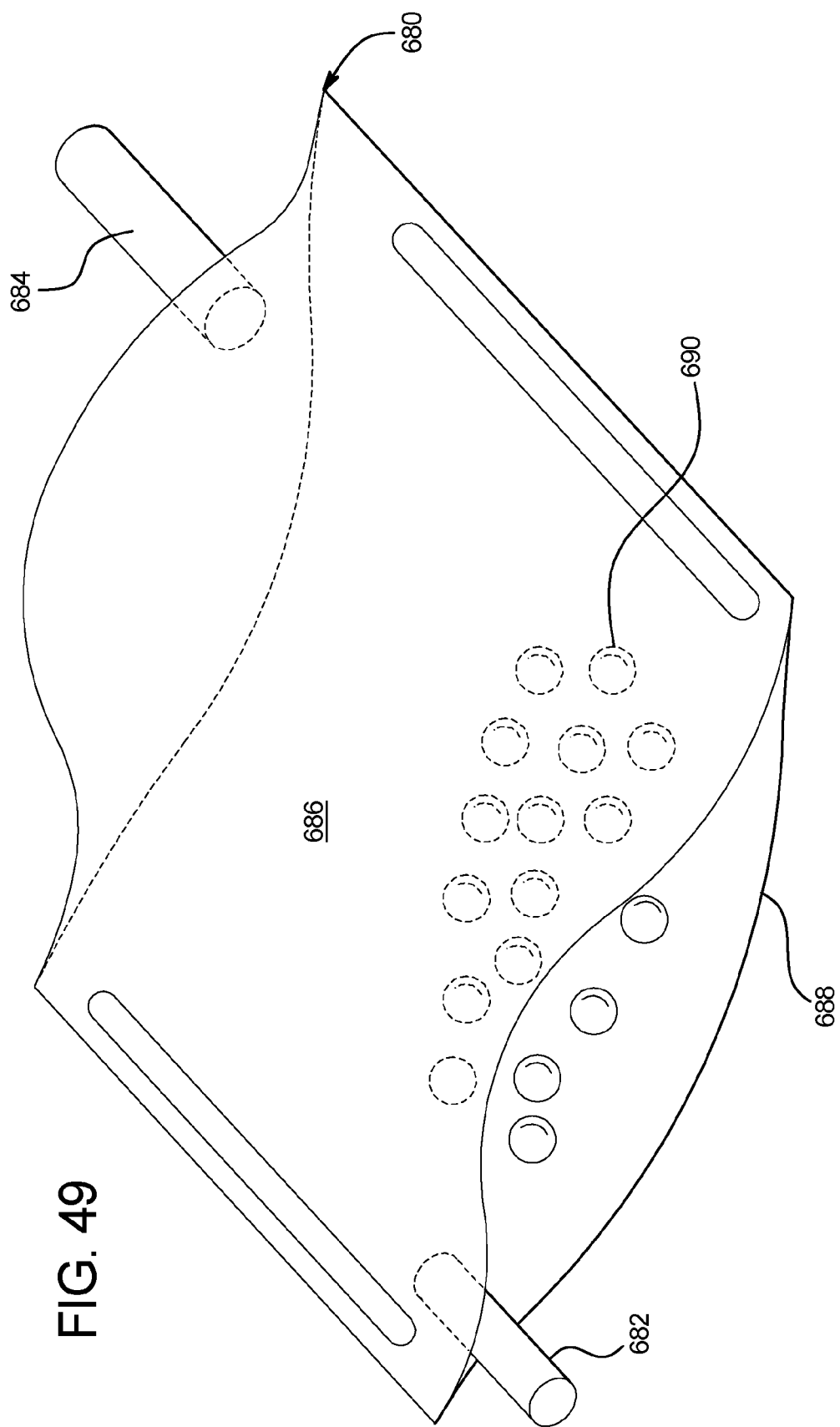
FIG. 49 is a perspective view of a disposable warmer bag or pouch containing a metal ball or metal wool susceptor.

Referring now to FIG. 49, fluid heating bag or pouch 680 illustrates yet another alternative fluid heating module of the present disclosure. As has been discussed herein, the fluid heating modules of the present disclosure can be separate or stand alone modules that are connected to a disposable cassette or elsewhere in a disposable set, such as inline with a patient line, or in a solution line for example. Bag or pouch 680 illustrates that it is also possible to place conductive susceptor materials in a fluid bag or pouch, such as supply bag or a warmer bag. In the illustrated embodiment, bag 680 provides a fluid inlet 682 and a fluid outlet 684, which are ultrasonically welded or adhesively bonded to one or more sheets 686 and 688 forming the pouch or bag 680. Sheets 686 and 688 can be made of polyvinyl chloride ("PVC") or other high temperature flexible, medical grade plastic.

Pouch or bag 680 holds a plurality of stainless steel balls 690 in the illustrated embodiment. The stainless steel balls 690 operate as a susceptor or secondary coil to a primary inductive coil located in the dialysis instrument. The primary coil can be a pancake coil 42 or a helical coil 72. In an alternative embodiment, stainless steel balls 690 are replaced with another type of stainless steel media that allows fluid to flow therethrough, such as a stainless steel mesh, sintered metal or wool. The stainless steel media can be magnetically susceptible or nonmagnetic as discussed herein.

Plate Heater Applying Positive and Negative Pressure

Figure 50:
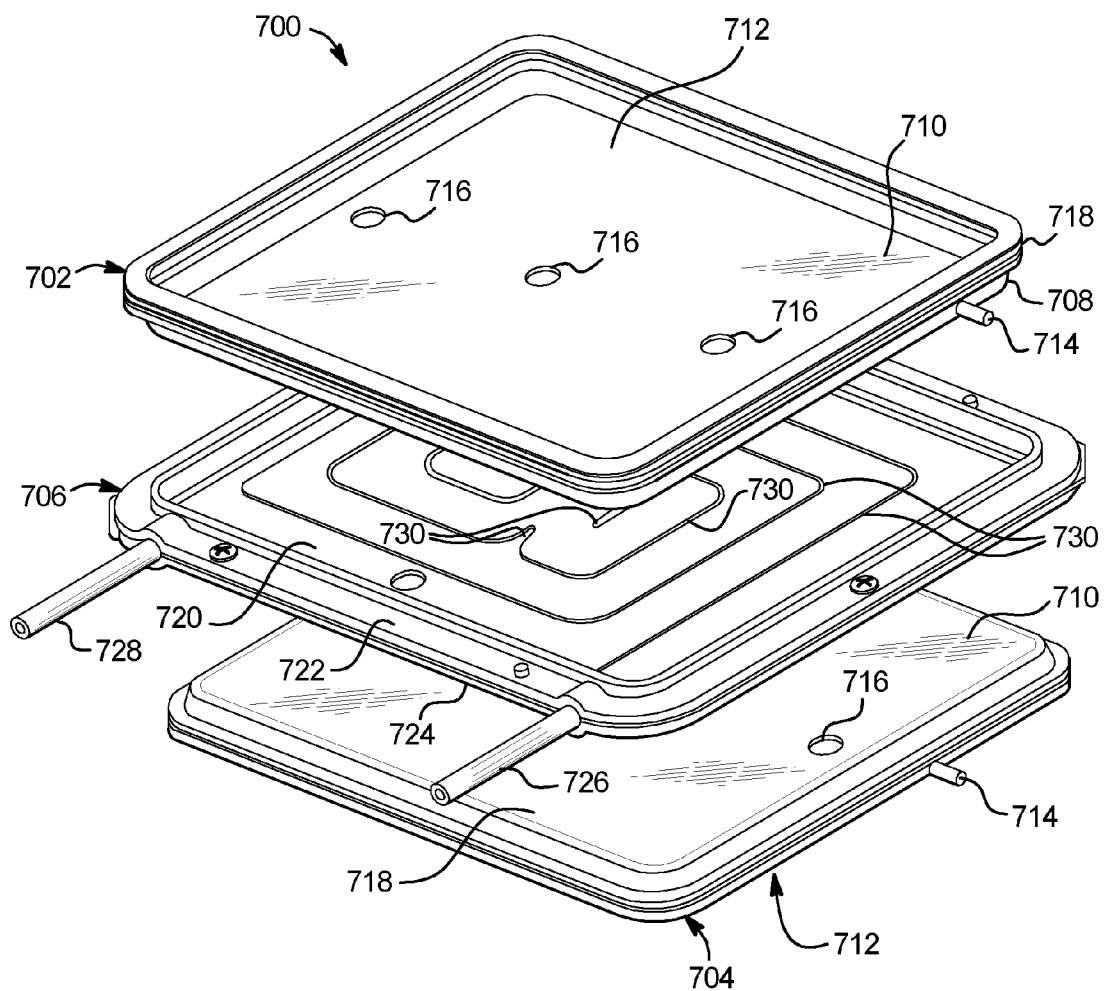
FIG. 50 is a perspective view of a fluid heating system capable of supplying positive or negative pressure between the heater and the disposable heating interface.

Referring now to FIG. 50, heating system 700 illustrates an alternative heating system that uses pressure and a vacuum to enhance heat transfer efficiency and that provides additional benefits discussed herein. Heating system 700 includes an upper heater 702, a lower heater 704 and a fluid heating pathway assembly 706. Upper heater 702 and lower heater 704 each include a heating plate 708, a heating plate or surface 710 and an outer cover 712. Heating plate 708 for both upper and lower heaters 702 and 704 includes or defines an aperture or port 714, which provides a connection to one or more pneumatic source, including a negative pressure source and a positive pressure source.

Heating surface or heating plate 710 includes or defines one or more opening 716, which transmits the positive or negative pressure applied through port 714, and plenum between outer cover 712 and plate 710, to a flexible heating section 720 of assembly 706. Opening(s) as described herein are configured to maximize the distribution of the positive or negative pressure across the entire flexible heating section 720.

In one embodiment, tubes (not illustrated) are connected to pneumatic ports 714. Those tubes run for example to a valved portion of the disposable, such as one located on a disposable cassette as illustrated above or to a series of pinch clamps (not illustrated). The disposable cassette valves can be operated electrically or pneumatically. The pinch clamps can be actuated electrically, e.g., in a solenoid-like manner.

FIG. 1 illustrates electronics for inductive heating. System 700 is primarily a resistive heating embodiment. Its electronics, like those of circuit 24 can include a logic implementer, like implementer 16 of circuit 24, which includes a processor, such as a microprocessor, and a memory, including for example random access memory ("RAM") and read-only memory ("ROM"). The memory and processing can be software based as it is known in the art. Alternatively, one or more application specific integrated circuit ("ASIC") can be used. The logic implementer for resistive system 700, like logic implementer 16, also includes the ability to accept input signals 18*a* and to accept output signals 18*d*. Input signals 18*a* can be signals from sensors, such as a temperature sensor, a flow sensor, an air detection sensor or other type of sensor used in connection with the dialysis instrument.

The resistive circuit, like circuit 24, sends output signals 18*b* to components within the dialysis instrument, such as to a power supply that powers any of the primary coils discussed herein for the inductive heating modules. Alternatively, the power source controls a duty cycle output to a resistive plate heater. Output signals 18*b* can also connect to solenoid valves or pinch clamps that can clamp or open a fluid line. The logic implementer of resistive circuit 24, like logic implementer 16, can for example receive an input from an air detection sensor that senses air in a disposable unit and can be programmed to send an output upon receiving the input to a pinch clamp solenoid, which closes one of the tubes connected to a port 714 of system 700.

Upper and lower heaters 702 and 704 form pneumatic plenums that allow a positive or negative pressure to be formed within and be redistributed accordingly through apertures 716 to the flexible fluid heating pathway 720. While three apertures 716 are shown, any number, pattern and size of apertures can be provided. For example, perforated metal having many small holes can be provided to distribute the positive or negative pressure evenly over the surface of flexible heating pathway 720.

Assembly 706 illustrates that fluid heating pathway 720 is sealed between assembly frames 722 and 724. Frames 722 and 724 in turn are sealed to heating plates 708 of upper and lower heaters 702 and 704 to form a sealed environment, which holds the positive or negative pressure of system 700.

Alternatively, the flexible sheets of pathway 720 are sealed together (i) to form fluid heating pathway 720 and (ii) around inlet tube 726 and outlet tube 728, which enables fluid to be pumped into and out of fluid heating pathway 720. Upper and lower heating plates 708 are then clamped together around the sealed fluid pathway 720 to provide a sealed environment. For example, heating plates 708 can have a soft gasketing material or O-ring 718, which provides a compression seal on either frame 722/724 or directly onto the sheeting of flexible fluid pathway 720. In a pneumatic system, a inflatable bladder (not illustrated) can be pressurized against one of the heaters 702 and 704 to compress the sections together and to compress seals 718 thereby opening or closing the sealed environment of system 700.

In one embodiment, heating surfaces 710 are resistive heating surfaces. Heating surfaces 710 can be heated by resistive heating elements (not illustrated) placed in thermal contact with the non-exposed sides of heating surfaces 710, between the surfaces and covers 712. Electrical insulation is provided between the AC mains powering the resistive heating elements (not illustrated) and the disposable fluid heating pathway 720.

In an alternative embodiment, a current is applied inductively to the surfaces 710 which heat due to the resistive material of the heater plates. The lack of direct contact between the inductive heated of surfaces 710 satisfies the requirement for electrical insulation between the AC mains and disposable fluid heating pathway 720.

The ability to apply a positive or negative pressure offers many benefits to fluid heating. For example, the application of positive or negative air pressure to the surface of fluid heating path 720 enables the amount of film or sheeting of pathway 720 that contacts heater plates 720 to vary relative to ambient air pressure and fluid pressure. One important pressure to monitor or control is a pressure differential across the sheets forming fluid heating pathway 720 (which can be considered as fluid pressure versus air pressure). In one case, negative air pressure applied between pathway 720 and surfaces 710 forces the disposable surfaces to conform to plates 710, maximizing the surface area contact between the film of pathway 720 and the plates 710. This allows for better heat transfer between the plates and the fluid.

The ability to apply negative pressure between plate 710 and pathway 720 also prevents a relative negative fluid pressure from collapsing the disposable, which could prevent or severely restrict the flow of dialysis fluid through the heater. Such a situation can occur when the source of a solution is elevationally below a fluid pump and the fluid pump is located downstream from heating system 700. In addition, when the fluid pathway 720 is located downstream from the pump and the fluid destination (such as the patient) is lower elevationally than the fluid pathway 720, the heating section of the disposable can also collapse or partially collapse. Although these conditions would still allow fluid to flow through the heater, such flow would occur with a loss of contact between the film and the heater plates, reducing heat transfer between the plates and the fluid.

As discussed above, system 700 also allows a positive pressure to be applied between plates 710 and fluid heating pathway 720. The application of the positive pressure allows dialysis system 700 to purge fluid from dialysis fluid pathway 720 and from potentially other areas of the disposable set connected to fluid pathway 720. In essence, the application of positive pressure causes fluid heating pathway 720 to act as a membrane pump to push fluid out of the fluid heating pathway, either upstream into inlet line 726, for example, or into a supply bag or through outlet line 728 to drain.

One reason system 700 applies positive pressure to heating pathway 720 is to prevent overheating when fluid flow stops for whatever reason. The positive pressure removes fluid from heating pathway 720 so that the section 700 does not become overheated. Another reason to apply positive pressure is to purge one type of dialysis fluid from fluid heating pathway 720, so that another type of dialysis fluid may be used. For example, different dialysis fluids can have different dextrose concentrations. Upon switching to a new concentration, system 700 can purge the dialysis solution of a first concentration from the fluid pathway, allowing the second solution to be used without a portion of it mixing with the solution of the first concentration that still remains in fluid pathway 720 or perhaps in other parts of the disposable set.

Fluid heating pathway 720 is defined by a heat sealed, ultrasonically sealed or adhesively bonded seal 730 that forms a seam spiraling inwardly from inlet 726 and then back outwardly to outlet 728. In one embodiment, apertures 716 are aligned with seam 730 to enable the vacuum or positive pressure to be initiated at a portion of seam 730, so that the vacuum or positive pressure can travel along the seam. This enable the vacuum on positive pressure to be readily disbursed about the entire surface area on both sides of fluid heating pathway 720.

One or both of the outer surfaces of fluid pathway 720 and the contacting surface of plate 710 can be textured so as to allow the positive pressure or vacuum to be applied through the interstices of the texture. The texture in this manner further aids in spreading the positive or negative pressure throughout the entire surface of fluid heating pathway 720. The texture also operates to prevent air pockets from forming between the film of pathway 720 and the heater plates 710.

In an embodiment, the inner surface of the sheets forming fluid heating pathways are also textured so that when system 700 applies a positive pressure to the outside of heating pathway 720, the textured surfaces help to evacuate all the fluid from inside heating pathway 720. The inner textured surfaces also help to prevent fluid from being trapped within pathway 720.

A more thermally conductive material, such as a stainless steel foil, may replace or be applied to one or both pieces of the film used to make fluid heating pathway 720. The stainless steel foil increases heat transfer between heater plate 710 and the fluid within pathway 720. Applying a vacuum between the surface of the foil and heater plate 710 allows a stiffer foil surface to conform better to the heater plate, further increasing heat transfer.

Figure 51A:
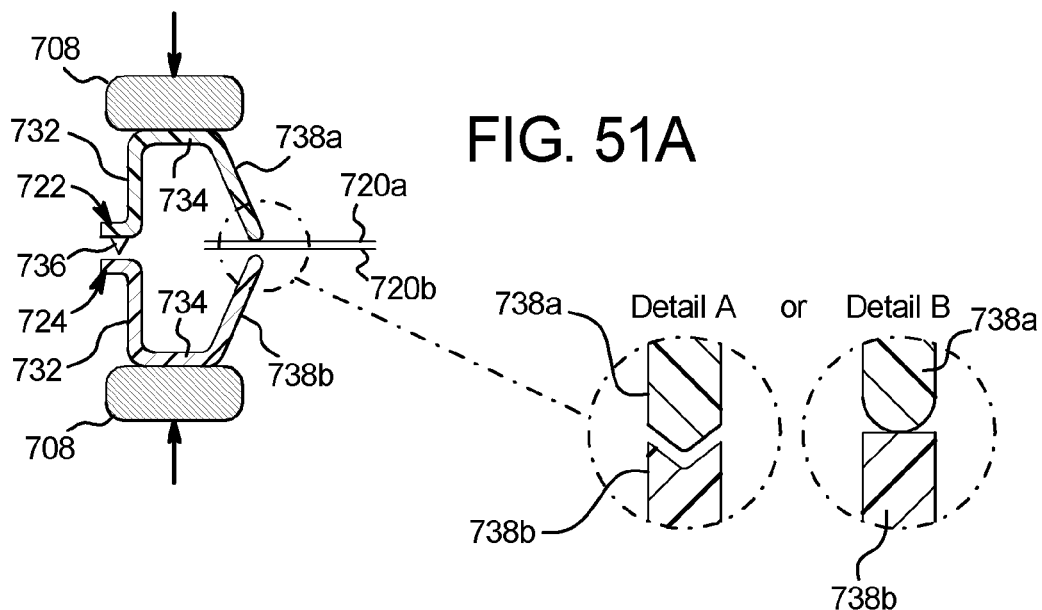
FIGS. 51A to 51I show multiple embodiments for sealing the disposable heating pathway to a frame and to an inlet or outlet tube to create a pressurized environment for the system of FIG. 50.

Referring now to FIG. 51A, one embodiment for sealing upper and lower heaters 702 and 704 to heating pathway 720 is illustrated. In this and following figures, individual sheets of fluid heating pathway 720 are marked as sheets 720a and 720b. Frames 722 and 724 in the illustrated embodiment provide a relatively wide area 734, which can accept a relatively large force, e.g., from heating plates 708 of upper and lower heaters 702 and 704. The force is imparted to clamping members 738a and 738b, which in turn impart a relatively sharp sealing force to sheets 720a and 720b.

FIG. 51A illustrates that frame member 732 of frame 722 includes an energy director 736, which directs ultrasonic energy and to help create an ultrasonic weld against frame member 732 of frame 724 and around the perimeter of the frames and sheets 720a and 720b.

Detail A of FIG. 51A shows that in one embodiment the edges of clamping members 738a and 738b are configured to have a mating relationship, such as outwardly and inwardly mating projecting triangles. Alternatively, detail B of FIG. 51A shows that clamping members 738a and 738b have an abbutting, e.g., rounded versus square interface.

Figure 51B:
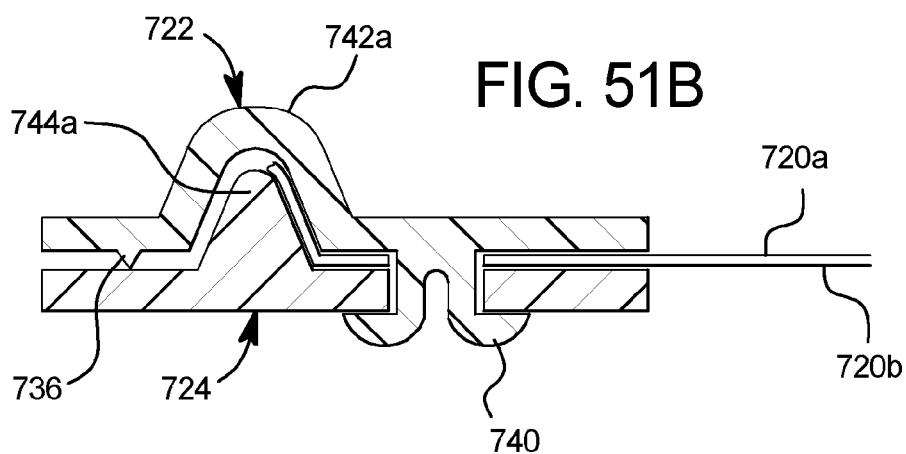

FIG. 51B illustrates one embodiment for applying frames 722 and 724 to sheets 720a and 720b. Here, a locking mechanism 740 of frame 722 locks to frame 724 and pulls a U-shaped undulation 742a formed in frame 722 against a mating hump 744a of frame 724, so as to seal sheet 720a to sheet 720b. Locking mechanism 740 is a heat stake that locates and captures flexible sheets 720a and 720b within frames 722 and 724. FIG. 51B also includes energy director 736 described above in connection with FIG. 51A.

Figure 51C:
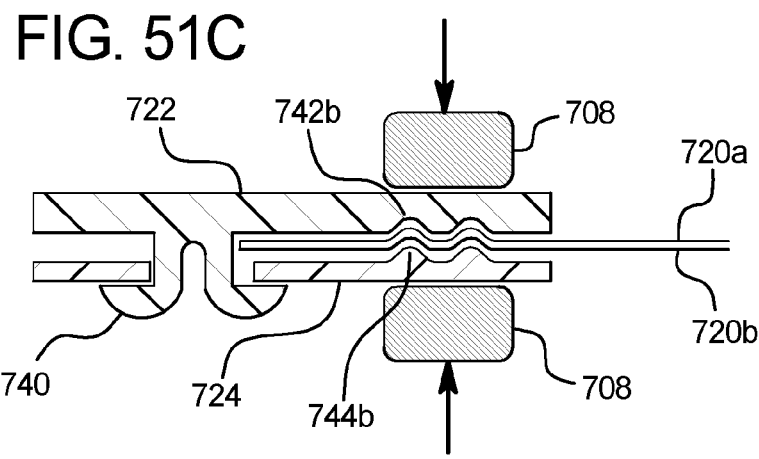

FIG. 51C illustrates another embodiment for frames 722 and 724 shown in FIG. 50. Here again, locking mechanism 740 locks frame 722 to frame 724 and serves as a heat stake that locates and captures flexible sheets 720a and 720b within frames 722 and 724. Frame 722 provides alternative undulations 742b and frame 724 provides alternative mating humps 744b. Heating plates 708 of upper and lower heaters 702 and 704, for example, are forced against heating path frames 722 and 724 at the interface where undulations 742b mate with bumps 744b.

Figure 51D:
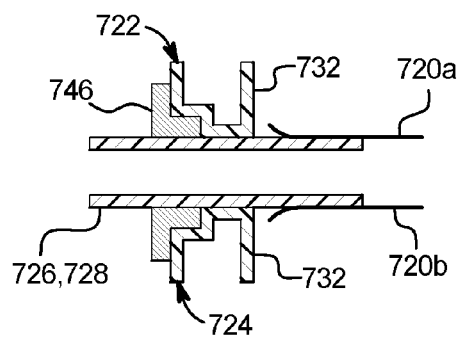

FIG. 51D illustrates an embodiment for sealing the interface of sheets 720a and 720b with inlet or outlet tube 726 or 728. Here, tubes 726 and 728 (or portions thereof) are rigid pieces of tubing. Sheets 720a and 720b are bonded, heat sealed or welded to tubing 726 or 728. Frame members 732 of frames 722 and 724 compress a gasket 746 against rigid tubing portion 726, 728.

Figure 51E:
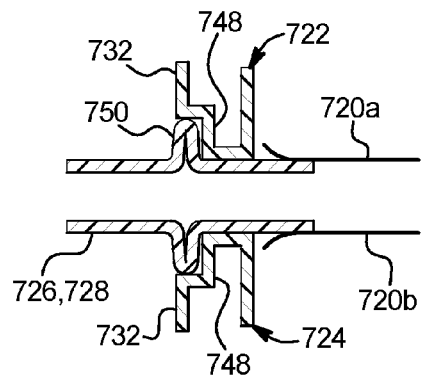

FIG. 51E illustrates an alternative embodiment, in which each frame member 732 includes a stepped portion 748 that compresses a swage portion 750 of tubing 726, 728. Swage portion 750 in the illustrated embodiment is a bunched or crimped section of tubing 726, 728, which aids in making a compression seal between the tubing and stepped portions 748 of frame members 732.

Figure 51F:
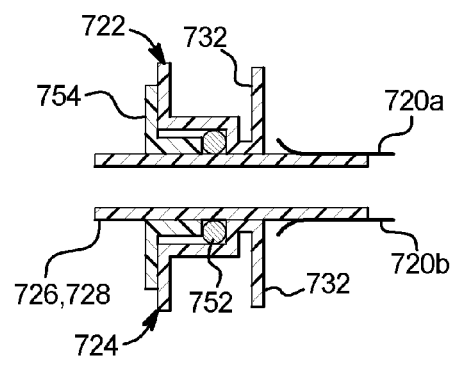

Referring now to FIG. 51F, a further alternative embodiment for the interface between the sheeting and on inlet and outlet tubing is illustrated. Here, frame members 732 of frames 722 and 724 are bent to compress an O-ring 752 around tube 726/728. Frame members 732 also enclose a bushing 754, which aids in making a compression seal between the tubing and O-ring 752.

Figure 51G:
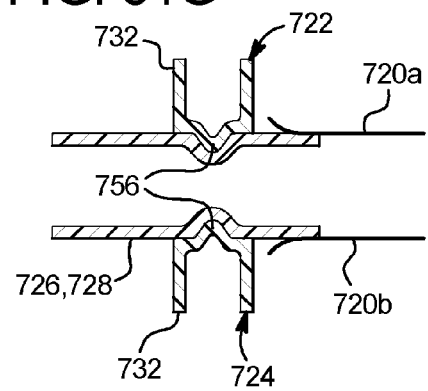

Referring now to FIG. 51G, in a further alternative embodiment tubing 726, 728 is compressible. Here, frame members 732 of frames 722 and 724 are spaced apart, such that rounded tips 756 of frame members 732 compress tubing 726 and 728 slightly inwardly to make a seal, but so that the tubing remains open for fluid flow.

Figure 51H:
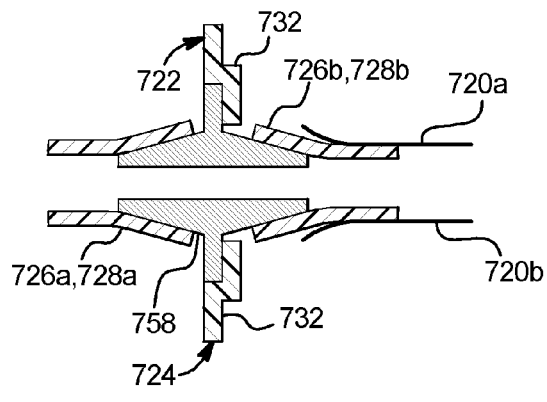

Referring now to FIG. 51H, in a further alternative embodiment tubes 726 and 728 are separated into tube sections 726a and 726b and tube sections 728a and 728b. The two sets of sections are mated to a bulkhead fitting 758, which in turn is sealed to stepped frame members 732 of upper and lower frames 722 and 724, respectively.

Figure 51I:
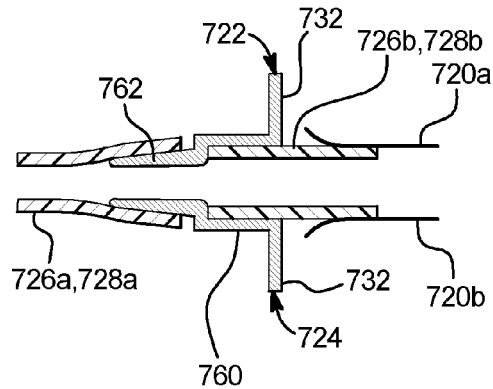

In FIG. 51I, frame members 732 of frames 722 and 724 form a female connector portion 760 for sealingly receiving tube section 726b or 728b and a male port 762 for sealingly receiving tubing section 726a or 728a.

Heating Control Architecture

The control of the fluid heating embodiments described herein, especially the inductive embodiments, can involve separate control regimes, one to control fluid temperature (FIG. 52) and one to control safety, that is, to prevent the module from overheating due, for example, to air passing through the heater. The safety control is configured to override the regular control of fluid temperature whenever air is detected in the system. The regular fluid heating algorithm is discussed next followed by the additional safety control.

Fluid Heating Control

Figure 52:
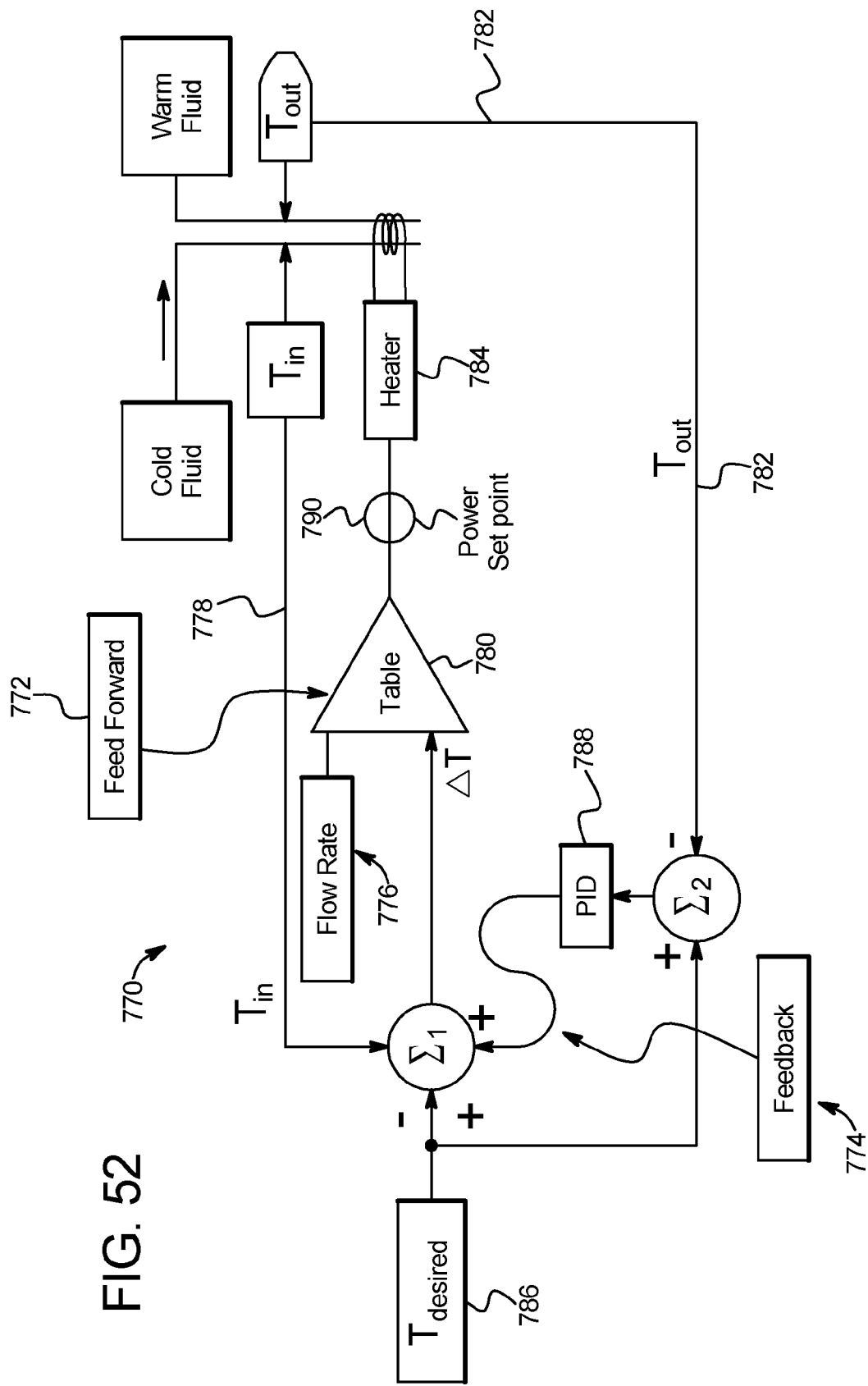
FIG. 52 is a schematic diagram illustrating one embodiment for a control scheme that can control the heating systems discussed herein.

Referring now to FIG. 52, control scheme 770 illustrates one embodiment for a control algorithm that can control fluid heating for any of the fluid heating embodiments described herein, including all inductive and resistive embodiments (even though a conductive coil is shown with cold fluid input and warm fluid output in FIG. 52). Control scheme 770 is operated on or by a logic implementer, such as logic implementer 16 described above and shown in FIG. 1. Circuit 24 operating with logic implementer 16 in FIG. 1 would be modified from that as shown to operate with a resistive rather than the illustrated inductive fluid heating embodiment. Control scheme 770 includes a feedforward portion 772 and a feedback portion 774 described in detail below.

In one embodiment, the heating system uses control scheme 770 to control the power inputted to the heater. Control scheme 770 includes a feedforward portion 772, which uses a table 780 that relates dialysis fluid flowrate 776 (e.g., instantaneous measured or calculated flowrate described herein) and delta T ($\Delta T$) to generate a power setpoint 790 of a heater power supply and heater 784. Power supply and heater 784 heat cold fluid at an inlet temperature 778 to a warm fluid having an outlet fluid temperature 782.

Control scheme 770 also includes a feedback loop 774 having feedback control 788 discussed below, which outputs to a summing portion ($\Sigma_1$) of control scheme 770. Summing portion ($\Sigma_1$) of control scheme 770 outputs delta T ($\Delta T$) to table 780. The other factors inputting to the summing portion ($\Sigma_1$) of control scheme 770 include a desired outlet fluid temperature 786, which is a constant value in one embodiment, and dialysis fluid inlet temperature 778 (e.g., measured as described below). Delta T ($\Delta T$) is accordingly:

$$\Delta T = T_{desired}\,786 + \text{feedback output } 788 - \text{measured } T_{in}\,778$$

Table 780 in one embodiment includes values derived from a correlation of power setpoint 790 with fluid flowrate 776 and delta fluid temperature. The correlation is tabulated in a table as shown below:

|  | Power Supply Setpoint | | | |
| --- | --- | --- | --- | --- |
|  | $\Delta T1$ | $\Delta T2$ | $\Delta T3$ | $\Delta T4$ |
| Flowrate 1 | Setpoint 1, 1 | Setpoint 2, 1 | Setpoint 3, 1 | Setpoint 4, 1 |
| Flowrate 2 | Setpoint 1, 2 | Setpoint 2, 2 | Setpoint 3, 2 | Setpoint 4, 2 |
| Flowrate 3 | Setpoint 1, 3 | Setpoint 2, 3 | Setpoint 3, 3 | Setpoint 4, 3 |
| Flowrate 4 | Setpoint 1, 4 | Setpoint 2, 4 | Setpoint 3, 4 | Setpoint 4, 4 |

The basis for the table comes from the specific heat calculation $Q=m*c*\Delta T$ in which Q is the energy required to heat a mass of fluid m having a specific heat c from one temperature to another temperature, $\Delta T$. Because the fluid is flowing, a similar equation can be written $P_f = Q/t = (m/t)*c*\Delta T$, in which $P_f$ is the power (energy Q per unit time t) required to heat a fluid flowing at a rate of m/t (mass per unit time) having a specific heat of c from one temperature to another temperature, $\Delta T$. The table accounts for the measured fluid flow rate and desired change in fluid temperature, $\Delta T$. Flowrate is known using a flow meter, assumed from a known pump speed setting, or from a calculation as discussed below. The $\Delta T$ is calculated as shown in FIG. 52. The constants, including the specific heat of the fluid being heated (which is a constant for water or dialysate and have nearly identical specific heat constants), are incorporated when the table is developed. The specific heat of the dialysis fluid is accordingly assumed to be a constant in formulating table 780 for a particular dialysis fluid.

Power into the fluid $P_f$ is a desired power input, which is independent of the heating module used. A power supply setpoint ($P_{setpoint}$) for a specific one of the heaters takes into account the efficiency of the heater and other relationships such as power supply non-linearities and heat transfer ratios between the susceptor and the fluid at various flow rates that relate the power setpoint to the power delivered to the fluid. So, for any desired flow rate and change in temperature, $\Delta T$, a power supply setpoint, $P_{setpoint}$, exists and is recorded in the table.

To generate table 780, the heating system in one embodiment is tested empirically at various flowrates, delta fluid temperatures and power supply setpoints. The collected data is used to complete the table. After the table has been developed, a specific combination of measured flowrate and desired delta temperature exists. Then, the corresponding power supply setpoint is applied to the power supply and the fluid is heated by nearly the same temperature delta as when the table was developed. In one embodiment, the power setpoint to the heater power supply is adjusted using an electronic control input. The setpoint input can be an analog setpoint (e.g., 4 to 20 mA or 0 to 5 VDC) or digital setpoint (e.g., pulse width modulated ("PWM") setpoint).

As an example, to generate the table, the system 770 is operated at the specific flowrate, Flowrate 1, as shown in the table above with an applied power supply setpoint, Setpoint 1,1 generating a delta temperature ΔT1. The corresponding points in the table are recorded. Each row and column in the table is completed in the same manner. In an example using the completed table, when the system 770 measures a flow rate 776, such as Flowrate 2, and measures an inlet fluid temperature of Tin 778, the system desires an outlet fluid temperature of Tout 782, yielding a ΔT calculation=$T_{out}-T_{in}$=of, for example, ΔT3. The power supply setpoint Setpoint 3,2 is found in the table. The setpoint is applied to the power supply, which should produce a heating system response according to when the table was generated, producing an outlet fluid temperature of $T_{out}$. If the measured flowrate or delta temperature, ΔT, does not exactly exist in the table, an algorithm can be applied to the data of the table to interpolate the required power setpoint. Or, the closest intersecting data point can be chosen.

In an alternative embodiment, logic implementer 16 calculates $P_{setpoint}$ as needed using equations developed from the empirical measurements used to develop the table and measured flowrate 776, measured inlet temperature 778 and desired temperature 786. In such case the table 780 is not needed. The table or algorithm yields or calculates a power setpoint for feedforward portion 772, which the heating system uses in attempting to make the outlet fluid temperature reach a desired temperature without the traditional overshoot or delay inherent in conventional feedback only PID temperature control systems.

For certain types of fluid pumping, such as turbine pumping, the flowrate is relatively continuous, making the flowrate portion of the above feedforward calculation relatively easy to implement. When the flowrate is discontinuous, such as with a diaphragm pump, the flowrate portion of the above feedforward calculation becomes more difficult.

For intermittent or pulsatile flow, one approach for implementing feedforward portion 772 of heating system 770 is to measure or calculate flowrate over small time periods (such as milliseconds) and to adjust the power setpoint at the same rate the flowrate is being measured. This approach attempts to produce a constant fluid temperature at the outlet of the heater by adjusting the power input throughout the pump stroke. If for example two diaphragm pumps are used out of phase with one another (one pumps-out while the other fills), and a period of time exists at the end of the stroke for each pump in which neither pump is pumping to or from the heater, the flowrate at the heater is zero for that period of time. In this approach, the power input to the heater will also be zero for that period of time. This system helps to prevent overheating of the heating module, e.g., and a no flow condition, which is more of a concern for the inductive heating systems.

Copending Patent Application entitled, "Medical Fluid Pumping System Having Real Time Volume Determination", filed Jul. 5, 2007, patent application Ser. No. 11/773,773, the pertinent portions of which are incorporated herein expressly by reference, discloses a real time method for determining instantaneous flowrate, and which is one way to provide the flowrate information to the feedforward portion 772 of system 770. The incorporated flowrate teachings are operable with a pneumatically controlled pumping system as described in that application.

Another approach for delivering flowrate data for the feedforward portion 772 of system 770 involves measuring flowrate over several pump strokes of the diaphragm pump, calculating the average flowrate over the period of time from the measured flowrates, and finding the power setpoint 790 from table 780 based on the average flowrate. The average flowrate measurement and calculation could be re-performed after a certain time interval, e.g., every couple of seconds. In this second approach, fluid pumped through the heater during peak flowrates is heated to a slighter lower temperature than average, while fluid pumped through the fluid heated in the heater during lower flowrate periods is heated to a slightly warmer temperature than average. When the over- and underheated fluids are mixed (for example via contact with portions of the disposable leading to the patient) the average fluid temperature equilibrates to a desired temperature. This flowrate method approach may require a larger heater surface mass and may be more applicable to resistive heating systems.

Feedback portion 774 of system 770 attempts to eliminate any error that the feedforward setpoint 790 causes in actual fluid outlet temperature 782. Feedback portion 774 uses a second summation $\Sigma_2$ that subtracts measured outlet fluid temperature 782 from desired outlet fluid temperature 786. The output of second summation $\Sigma_2$ is inputted to a feedback equation or algorithm 788. In one embodiment, before initiating the feedback control 774, system 770 waits for measured outlet temperature 782 to reach a steady state. Here, the output of feedback control 788 can be set to zero for $\Sigma_1$ until outlet temperature 782 reaches a steady state.

In one embodiment, feedback portion 774 is updated each time feedforward portion 772 is updated. That is, each time the feedforward setpoint 790 of feedforward portion 772 is updated, whether or not the update period is on the order of milliseconds or seconds, the setting potentially takes into account one or more updated gain (described below) of the feedback portion 774. Alternatively, for example when feedforward setpoints are updated frequently, the one or more gain of the feedback portion 774 can be updated instead, once for every certain number of updates of feedforward setpoint 790, e.g., once every ten or one-hundred updates of feedforward power setpoint 790.

It is believed that the heating modules and corresponding heating systems described herein may vary from system to system, which can cause table 780 to produce different results (albeit minor) in different systems using the same type of heating module. That is, in one embodiment, a table 780 is generated once for each type of module and heater (e.g., averaging results for different ones of the module) and that table is used in each instrument having the particular heater and operating that particular module. The common table may produce different results for different ones of the same module. Feedback portion 774 compensates for this potential variation.

It should be appreciated that the instrument can store multiple tables for different modules operable with the instrument. It is also possible that the instrument can store multiple tables for different types of fluid, e.g., different viscosities or specific heats for the same module or for different temperature ranges of the same module and same fluid.

Feedback loop 774 generates an output to summation $\Sigma_1$, which outputs ΔT to table 780. Feedback portion 774 uses the measured temperature 782 (made, e.g., via downstream conductive contact 630 illustrated above) from $T_{desired}$ 786 at summation $\Sigma_2$ and any one or more of a proportional gain, integral gain and a derivative gain ("PID") at feedback algorithm 788, which is (are) applied to the output of summation $\Sigma_2$ to determine an updated output to summation $\Sigma_1$.

The proportional gain is influenced by how far away from the desired temperature that the measured outlet temperature is. The derivative gain is influenced by how quickly the measured temperature is moving towards (or away from) the desired outlet temperature. The integral gain is influenced by historical data, such as differences in the desired temperature from the measured outlet fluid temperature integrated over a recent time period such as several seconds.

System 770 uses a temperature sensor that inputs a signal indicative of outlet temperature 778 (e.g., measured at outlet contact 630) to logic implementer 16. Due to a fast response of heaters described herein, especially the thin walled inductive heaters, the temperature sensor in one preferred embodiment is a fast responding temperature sensor.

One suitable temperature sensor is an infrared sensor, commercially available from Exergen as the IRt/c Heat Balance series infrared thermocouple (e.g., part number IRt/c.01HB). This sensor has a fast response to changing fluid temperatures. The following system and method, however, improves response time of other, slower responding, types of temperature sensors.

The system and method use the fact that a temperature reading is changing to predict what the actual fluid temperature might be at a given point in time. The system and method then use an adjusted measured fluid outlet temperature 786' instead of the fluid outlet temperature 786 actually measured. The logic implementer 16 uses a mathematical derivative of the measured outlet temperature 786 at a past time versus an actual measured outlet temperature 786 at a current time to predict a current temperature of the fluid 786'.

It has been found that the inlet and outlet temperature sensors start to respond almost immediately to changes in fluid temperature, but that the actual response is too slow, that is, the sensor responds at the right time but not by enough, such that the output of the sensor lags behind the actual fluid temperature. The system and method accordingly assumes that if the measured fluid temperature has changed dramatically, e.g., increased, the actual fluid temperature has changed even more than the temperature derived from the sensor output, e.g., is actually higher than the derived temperature.

As an example, in one test the outlet temperature 786 of the fluid is sampled at constant intervals of 0.250 second. The present measured temperature sample $786_n$ is set to be $T_n$ and the previous temperature sample $786_{n-1}$ is set to be $T_{n-1}$ for the equation below. To correct for the rapidly changing measured temperature, the present fluid temperature $T_{fluid}$ (786') is adjusted as follows:

$$T_{fluid} = T_n + K*(T_n - T_{n-1}),$$

in which K is effected by physical constants in the system. K can be determined empirically and is a constant in the system determined to make the above equation accurate. Alternatively, K is determined via a differential equation, which takes into account a thermal resistance and capacitance of the system. The thermal system could for example be modeled as an electrical system having a resistance R and a capacitance C in a corresponding electrical circuit $V(t) = VI*e^{(-t/RC)}$. Here, t is time and VI is analogous to measured staring temperature. V(t) is analogous to measured temperature at time t.

According to the above equation, small temperature variations between temperature samples result in $T_{fluid}$ (786') being essentially equal to $T_n$ (786). When a large variation between temperature samples is measured, the factor K modifies the presently measured temperature $T_n$ (786) accordingly (adjusts the measured fluid temperature by the amount of the temperature change during the last two samples multiplied by K) to produce a different adjusted temperature $T_{fluid}$ (786') used in heating system 770.

It may be determined that if the change in temperature $\Delta T$ between the times of n and n−1 falls below a certain threshold value, then a resulting K factor may be unreliable due to noise in heating system 770. Here, $(T_n - T_{n-1})$ is set to zero and $T_{fluid}$ (786') is left to be $T_n$ (786).

It should be appreciated that actual time samples may be taken at time intervals different than 0.250 second. The method could further alternatively take many samples very quickly during a small time interval, average the samples together, and assign the average value to $T_n$ to decrease noise or increase resolution.

Figure 53:
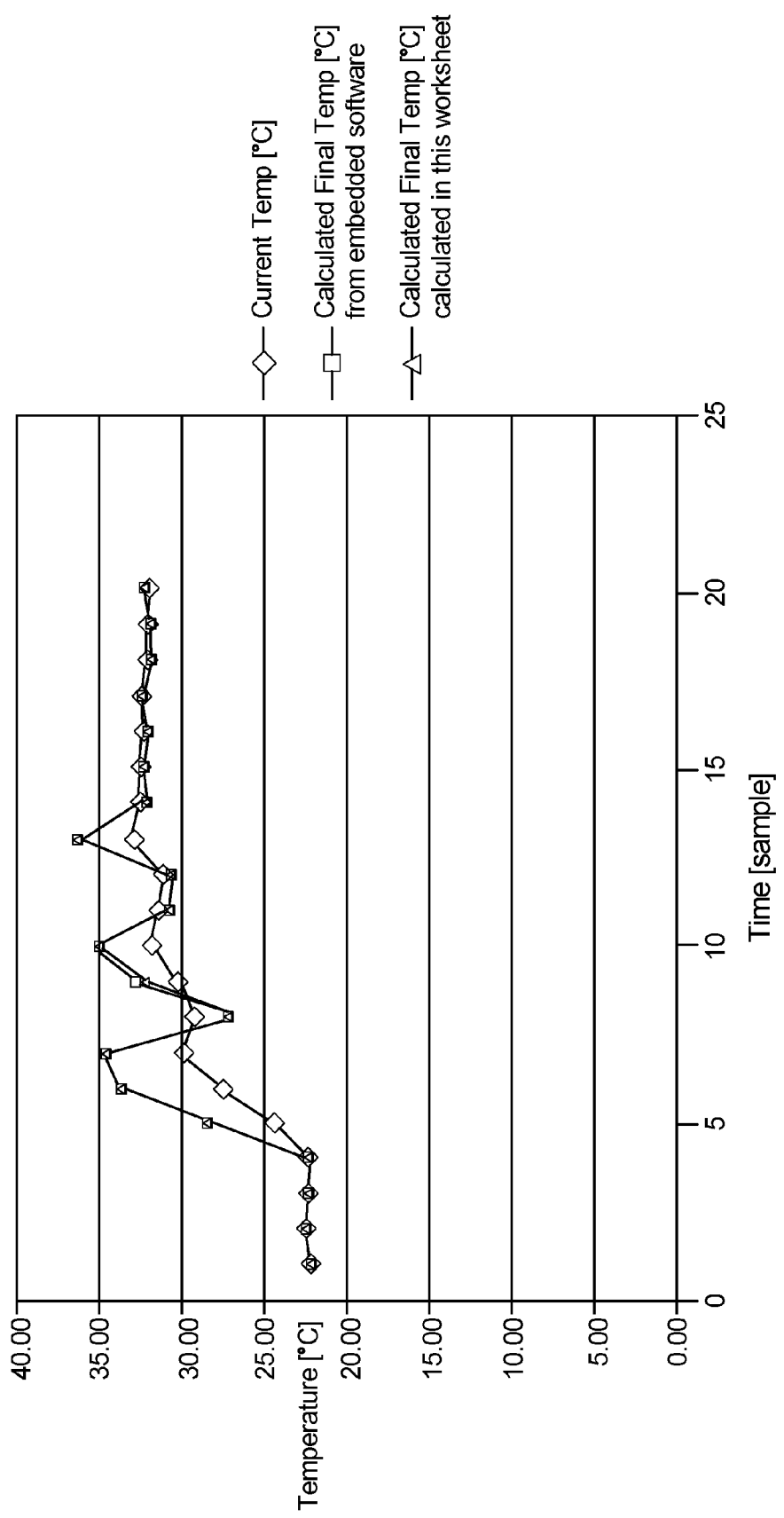
FIG. 53 is a plot showing data from a temperature sensor response time improvement method and algorithm.

FIG. 53 illustrates test data for the above method and algorithm. The line connecting the diamond data points represents actual fluid temperature. The line connecting the square data points represents the predicted fluid temperature based on the equation above as executed by the microcontroller reading and reporting the measured fluid temperature. The line connecting the triangular data points represents the results of the same equation with different constants on the reported data.

Heating Safety Control

As discussed herein, one primary heating system of the present disclosure is an inductive heating system using a primary coil and a susceptor. The systems use a relatively small amount of metal to heat the fluid, which means the systems do not store much energy and can dissipate energy quickly when needed. However, the susceptors can also increase in temperature rather rapidly due for example to the stoppage of dialysis fluid flow within the heater or the presence of an air bubble. The heating control architecture adds a heating safety control to the fluid heating control to combat the potential overheating problem. The heating safety control overrides the fluid heating control in situations in which the fluid heating control may not be adequate to avert a fluid overtemperature and a potential overheating of the heating module.

System 770 provides one measure to combat overheating due to stagnant or stopped fluid flow. As discussed above, system 770 inputs a power setting based on dialysis fluid flowrate. In one embodiment, system 770 knows the instantaneous flowrate and if a period of no flow is calculated or known, system 770 sets the power setting to zero for that period.

The safety control provides another measure to combat overheating due to stagnant or stopped fluid flow. Here, susceptor temperature is measured. If susceptor temperature increases too dramatically or for too long a time period, a flow stoppage or air problem is assumed. Here, safety control overrides system 770 and takes an evasive measure, e.g., setting the power setting to zero.

The susceptors can be in direct thermal contact with (i) fluid, (ii) a mixture of fluid and air, or (iii) pure air, such as before the disposable set is primed or if a large air bubble is drawn into the heater disposable. Dialysis fluid pulls more heat from the susceptors than does a fluid and air combination, which pulls more heat from the susceptors than does pure air. Air or partial air can therefore also cause an overheating of the heating module, especially in the inductive heating modules discussed herein.

The safety control employs a number of measures to combat overheating due to air. One measure is to look for air upstream of the fluid heating module. If air is detected or enough air is detected upstream of the heating module, the safety control can be configured to determine that an overheating problem is going to take place and perform a preventative override procedure. Here, using one or more known historical flowrate, the safety control can predict when and for how long the air bubble or slug will be present in the heating module and can lower or zero the power setpoint at the appropriate time and for the appropriate length of time. The goal here is to prevent the susceptor temperature from rising due to air in the module.

One suitable air sensor for the preventative control is believed to be a LifeGuard™ Air Bubble Detector provided by Zevex® Inc. of Salt Lake City, Utah. Model Numbers ZLG130 or ZLG200 are believed to be the pertinent ones at this time because it appears that they are specified to detect bubbles of a size that could cause overheating of the susceptors. It should be appreciated that the detection of air in the dialysis system, and thus the output of the air detectors, is useful for purposes other than fluid heating.

Another measure that the safety control provides to combat overheating due to air is again to measure the susceptor temperature. Here, if susceptor temperature increases too dramatically or for too long a time period, a flow stoppage or air problem is assumed, and the safety control overrides system 770 taking evasive action, e.g., setting the power setting to zero.

One advantage of using susceptor temperature in the safety control is that it is believed that susceptor temperature can be determined, at least accurately enough for safety control, electrically without additional sensors. The susceptors described herein have an electrical resistance that varies as a function of the temperature of the susceptor discussed herein. As discussed above, in one embodiment the susceptors are made from stainless steel. The resistance of stainless steel is a function of the temperature of the stainless steel. The present system and method contemplate the use of a resistance measurement of the susceptor to determine an average temperature of the susceptor.

By measuring the susceptor resistance, and knowing the relationship between the resistance and temperature of the susceptor, and at least one calibration point, which takes into account variations due to susceptor mass, the average temperature of the susceptor may be determined.

In one embodiment, the calibration point is determined after loading a heating module into the dialysis instrument. The calibration points can vary from module to module, e.g., due to small variations in susceptor length, width, wall thickness, etc., that is, variations due to susceptor mass. The safety control takes a resistance measurement when the susceptor is at a known temperature, such as when the susceptor is not being actively heated. The temperature of the susceptor can be assumed to be the temperature of one or an average of both conductive contacts 630 when no heating is taking place as the fluid is pumped past the susceptor and the temperature sensors. Or, a temperature sensor (e.g., an infrared temperature sensor, diode, thermistor, integrated circuit sensor, or resistance temperature device ("RTD")) can be used at the start of treatment to measure one or more temperatures of the susceptor at one or more measured resistances.

The safety control knows the temperature coefficient (ohm/° C.) or the relationship between resistance change and temperature change ($\Delta R/\Delta T$) for the particular type of metal used for the susceptor. In knowing the one or more calibration point resistance Rc, susceptor temperature Tc, and temperature coefficient of the susceptor metal, the safety system can measure resistance $R_t$ at a given time t during treatment and solve for the average susceptor temperature $T_t$. If the average susceptor temperature $T_t$ is too high or is increasing too quickly, the safety control takes evasive action as discussed above.

The safety control can measure resistance in at least the following ways:

(i) direct contact between heating elements (e.g., leads 14a and 14b of FIG. 1) and an electric circuit, which applies a current from a source through the leads to the resistance of the susceptor 14 and metal part 20a, measures a corresponding voltage and calculates the resistance from the applied current and measured voltage;

(ii) direct contact between heating elements (e.g., leads 14a and 14b of FIG. 1) and an electric circuit, which applies a voltage from a source through the leads to the resistance of the susceptor 14 and metal part 20a, measures a corresponding current and calculates the resistance from the applied voltage and measured current;

(iii) using circuit 24 and a known turns ratio of any of the susceptors described herein and known measured voltage and current to measure the voltage and current applied to the primary coil and calculating the resistance of the susceptor; and (iv) using circuit 24 to apply a resonant or decaying signal, which decays as a function of the resistance of the susceptor, measuring the decay of the oscillations, and correlating the measured decay to a resistance of the susceptor, which in turn is correlated to a temperature of the susceptor. As discussed above, in certain fluid control schemes described herein, a power setpoint is set to zero when instantaneous flowrate is also zero. This provides an opportune moment to measure a decay in the signal. The quicker the signal decays, the higher the resistance and corresponding average susceptor temperature. In an embodiment, amplitude peaks are monitored to determine an envelope of decay. Different envelopes are correlated to different resistances. Detecting a particular envelope yields a certain resistance, leading to average temperature.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis fluid heating system comprising:
a dialysis fluid heater;
a dialysis fluid carrying element in operable communication with the dialysis fluid heater to heat a dialysis fluid; and
a logic implementer configured to control the heater using
(i) a first heater input determined using a first feedforward determination at a first time from a first dialysis fluid temperature delta and a first dialysis fluid flowrate,
(ii) a feedback adjustment of a second dialysis fluid temperature delta using a measured dialysis fluid outlet temperature and at least two of a proportional gain, integral gain and derivative gain; and (iii) a second heater input determined using a second feedforward determination at a second time from the second dialysis fluid temperature delta and a second dialysis fluid flowrate.

2. The dialysis fluid heating system of claim 1, wherein the dialysis fluid heater is a resistance heater or an induction heater.

3. The dialysis fluid heating system of claim 1, wherein the dialysis fluid carrying element is one of: (i) a disposable heating pathway disposed separately from a disposable pumping cassette; (ii) a dialysis fluid heating pathway provided as part of the disposable pumping cassette; and (iii) a warmer bag.

4. The dialysis fluid heating system of claim 1, which includes at least one temperature sensor configured to measure the dialysis fluid outlet temperature and output an indicative signal to the logic implementer.

5. The dialysis fluid heating system of claim 4, wherein the temperature sensor is of a type selected from the group consisting of: (i) an infrared temperature sensor, (ii) a thermistor, and (iii) a resistance temperature device ("RTD"), (iv) diode and (v) integrated circuit.

6. The dialysis fluid heating system of claim 1, which includes a table relating heater inputs to temperature deltas and dialysis fluid flowrates, the logic implementer finding an appropriate heater input from the table.

7. The dialysis fluid heating system of claim 6, wherein the table is formed empirically.

8. The dialysis fluid heating system of claim 1, wherein the first heater input is at least one of (i) a power input and (ii) a power supply input, which powers the heater accordingly.

9. The dialysis fluid heating system of claim 1, wherein the first heater input is determined using an algorithm relating the first dialysis fluid temperature delta and the first dialysis fluid flowrate.

10. The dialysis fluid heating system of claim 1, wherein the logic implementer is configured to adjust the second dialysis fluid temperature delta by applying each of the proportional gain, integral gain and derivative gain.

11. The dialysis fluid heating system of claim 1, wherein the first dialysis fluid temperature delta is based on at least one of: (i) a desired dialysis fluid outlet temperature and a measured dialysis fluid inlet temperature; and (ii) the desired dialysis fluid outlet temperature, the measured dialysis fluid inlet temperature and the measured dialysis fluid outlet temperature.

12. The dialysis fluid heating system of claim 1, wherein the adjustment using the measured dialysis fluid outlet temperature includes a feedback algorithm applied to a summation of a desired dialysis fluid outlet temperature and the measured dialysis fluid outlet temperature.

13. The dialysis fluid heating system of claim 1, wherein the logic implementer is configured to adjust at least one of: (i) the measured dialysis fluid outlet temperature based on a rate of change of a temperature sensor output; and (ii) the dialysis fluid flowrate based on a real time determination of a flowrate.

14. A dialysis fluid heating system comprising:
a dialysis fluid heater;
a dialysis fluid carrying element in operable communication with the dialysis fluid heater to heat a dialysis fluid; and
a logic implementer configured to control the heater using
(i) a first heater input determined using a first feedforward determination at a first time from (a) a first dialysis fluid temperature delta relating a desired dialysis fluid outlet temperature and a measured dialysis fluid inlet temperature and (b) a dialysis fluid flowrate, and
(ii) a feedback adjustment using a feedback algorithm applied to a second dialysis fluid temperature delta relating the desired dialysis fluid outlet temperature and a measured dialysis fluid outlet temperature, wherein the feedback adjusted second dialysis fluid temperature delta is used to determine using a second feedforward determination at a second time a second heater input.

15. The dialysis fluid heating system of claim 14, which includes a power supply operable to power the dialysis fluid heater, the first and second heater inputs directed to the power supply, which powers the heater accordingly.

16. The dialysis fluid heating system of claim 14, the logic implementer configured to make the first and second feedforward determinations using a table or an algorithm.

17. The dialysis fluid heating system of claim 14, further comprising:
a primary inductor coil;
a susceptor induced by the primary coil to heat a dialysis fluid;
a sensor positioned to measure an electrical property of one of the susceptor and the primary inductive coil, wherein the logic implementer configured to determine a resistance of the susceptor from the measured electrical property, and relate the determined resistance to a temperature of the susceptor.

18. The dialysis fluid heating system of claim 17, wherein the logic implementer is configured to determine the resistance of the susceptor via (i) contact between the susceptor and an electrical circuit that applies one of a voltage and a current to the susceptor, the other of the voltage and the current being the measured electrical property; (ii) measuring a voltage and current applied to the primary inductive coil; and (iii) measuring a decay in oscillations of the property in a resonant mode due to the resistance of the susceptor.

19. The dialysis fluid heating system of claim 17, the logic implementer configured to relate the determined resistance to the temperature of the susceptor using (i) a calibration of a resistance determined when the temperature of the susceptor is known;
and (ii) a known temperature delta to a resistance delta relationship for the susceptor.

20. The dialysis fluid heating system of claim 19, the logic implementer further configured to use the temperature of the susceptor for at least one of (i) control of power to the primary inductive coil; (ii) detection of air in a fluid carrying element operable with the susceptor, and (iii) detection of fluid flow changes or stops.

* * * * *